(12) United States Patent
Houser

(10) Patent No.: US 8,961,541 B2
(45) Date of Patent: Feb. 24, 2015

(54) VASCULAR CLOSURE DEVICES, SYSTEMS, AND METHODS OF USE

(75) Inventor: Russell A. Houser, Livermore, CA (US)

(73) Assignee: Cardio Vascular Technologies Inc., Livermore, CA (US)

( * ) Notice: Subject to any disclaimer, the term of this patent is extended or adjusted under 35 U.S.C. 154(b) by 575 days.

(21) Appl. No.: 12/263,322

(22) Filed: Oct. 31, 2008

(65) Prior Publication Data

US 2009/0143789 A1    Jun. 4, 2009

Related U.S. Application Data

(60) Provisional application No. 61/005,435, filed on Dec. 3, 2007.

(51) Int. Cl.
*A61B 17/08*    (2006.01)

(52) U.S. Cl.
USPC ............................................ 606/142; 606/213

(58) Field of Classification Search
CPC .................. A61B 17/0057; A61B 2017/00615; A61B 2017/00898; A61B 2017/1205
USPC ............. 606/213, 139, 144–148, 142, 73, 95, 606/194
See application file for complete search history.

(56) References Cited

U.S. PATENT DOCUMENTS

| | | |
|---|---|---|
| 3,270,745 A | 9/1966 | Charle |
| 3,459,189 A | 8/1969 | Alley et al. |
| 3,675,639 A | 7/1972 | Climber |
| 3,702,611 A | 11/1972 | Fishbein |
| 3,859,998 A | 1/1975 | Thomas et al. |
| 3,874,388 A | 4/1975 | King et al. |
| 3,937,733 A | 2/1976 | Ulbrich et al. |
| 4,007,743 A | 2/1977 | Blake |
| 4,008,720 A | 2/1977 | Brinckmann et al. |
| 4,052,989 A | 10/1977 | Kline |
| 4,108,175 A | 8/1978 | Orton |
| 4,154,226 A | 5/1979 | Hennig et al. |
| 4,207,870 A | 6/1980 | Eldridge |
| 4,314,555 A | 2/1982 | Sagae |

(Continued)

FOREIGN PATENT DOCUMENTS

| | | |
|---|---|---|
| EP | 0047618 A1 | 3/1982 |
| EP | 0139 091 A1 | 5/1985 |

(Continued)

OTHER PUBLICATIONS

International search report and written opinion dated Mar. 8, 2011 for PCT Application No. US2010/030531.

(Continued)

*Primary Examiner* — Vy Q Bui
(74) *Attorney, Agent, or Firm* — Wilson, Sonsini, Goodrich & Rosati; Darby Chan

(57) ABSTRACT

A tissue closure system can include a deployment instrument and a sealing element. The deployment instrument can be slidably mounted to and guided by a tubular medical device. The deployment instrument can be advanced over the tubular medical device to the desired location. The sealing element can then be advanced off of the end of the tool. The sealing element can include tissue engaging elements that are configured to automatically close upon deployment to bring together tissue. A slidably attached guided skin (or other tissue) cutter can also be used if desired to facilitate entry of the deployment instrument.

46 Claims, 67 Drawing Sheets

(56) References Cited

U.S. PATENT DOCUMENTS

| | | |
|---|---|---|
| 4,317,445 A | 3/1982 | Robinson |
| 4,357,846 A | 11/1982 | Primo |
| 4,394,373 A | 7/1983 | Malette et al. |
| 4,447,915 A | 5/1984 | Weber |
| 4,468,224 A | 8/1984 | Enzmann et al. |
| 4,487,605 A | 12/1984 | McGaughey et al. |
| 4,525,157 A | 6/1985 | Vaillancourt |
| 4,543,086 A | 9/1985 | Johnson |
| 4,598,711 A | 7/1986 | Deniega |
| 4,610,659 A | 9/1986 | Friese |
| 4,610,671 A | 9/1986 | Luther |
| 4,645,492 A | 2/1987 | Weeks |
| 4,650,488 A | 3/1987 | Bays et al. |
| 4,652,256 A | 3/1987 | Vaillancourt |
| 4,654,031 A | 3/1987 | Lentz |
| 4,655,750 A | 4/1987 | Vaillancourt |
| 4,669,473 A | 6/1987 | Richards et al. |
| 4,710,173 A | 12/1987 | McFarlane |
| 4,738,658 A | 4/1988 | Magro et al. |
| 4,744,364 A | 5/1988 | Kensey |
| 4,770,183 A | 9/1988 | Groman et al. |
| 4,772,264 A | 9/1988 | Cragg |
| 4,774,091 A | 9/1988 | Yamahira et al. |
| 4,787,391 A | 11/1988 | Elefteriades |
| 4,792,326 A | 12/1988 | Tews |
| 4,832,045 A | 5/1989 | Goldberger |
| 4,836,204 A | 6/1989 | Landymore et al. |
| 4,852,568 A | 8/1989 | Kensey |
| 4,863,431 A | 9/1989 | Vailancourt |
| 4,890,612 A | 1/1990 | Kensey |
| 4,894,052 A | 1/1990 | Crawford |
| 4,904,240 A | 2/1990 | Hoover |
| 4,955,890 A | 9/1990 | Yamamoto et al. |
| 4,957,105 A | 9/1990 | Kurth |
| 4,959,048 A | 9/1990 | Seder et al. |
| 4,961,729 A | 10/1990 | Vailancourt |
| 5,021,059 A | 6/1991 | Kensey et al. |
| 5,030,207 A | 7/1991 | Mersch et al. |
| 5,035,701 A | 7/1991 | Kabbara |
| 5,053,008 A | 10/1991 | Bajaj |
| 5,053,046 A | 10/1991 | Janese |
| 5,059,210 A | 10/1991 | Clark et al. |
| 5,061,274 A | 10/1991 | Kensey |
| 5,074,840 A | 12/1991 | Yoon |
| 5,092,841 A | 3/1992 | Spears |
| 5,100,416 A | 3/1992 | Oh et al. |
| 5,108,420 A | 4/1992 | Marks |
| 5,108,421 A | 4/1992 | Fowler |
| 5,116,357 A | 5/1992 | Eberbach |
| 5,120,319 A | 6/1992 | Van Heugten et al. |
| 5,120,527 A | 6/1992 | Li et al. |
| 5,127,626 A | 7/1992 | Hilal et al. |
| 5,128,121 A | 7/1992 | Berg et al. |
| 5,160,339 A | 11/1992 | Chen et al. |
| 5,163,959 A | 11/1992 | Herrick |
| 5,171,270 A | 12/1992 | Herrick |
| 5,176,653 A | 1/1993 | Metals |
| 5,192,301 A | 3/1993 | Kamiya et al. |
| 5,201,900 A | 4/1993 | Nardella |
| 5,207,691 A | 5/1993 | Nardella |
| 5,209,776 A | 5/1993 | Bass et al. |
| 5,219,353 A | 6/1993 | Garvey et al. |
| 5,222,974 A | 6/1993 | Kensey et al. |
| 5,254,133 A | 10/1993 | Seid |
| 5,269,809 A | 12/1993 | Hayhurst et al. |
| 5,275,616 A | 1/1994 | Fowler |
| 5,283,063 A | 2/1994 | Freeman |
| 5,290,310 A | 3/1994 | Makower et al. |
| 5,292,332 A | 3/1994 | Lee |
| 5,292,362 A | 3/1994 | Bass et al. |
| 5,306,234 A | 4/1994 | Johnson |
| 5,314,410 A | 5/1994 | Marks |
| 5,324,306 A | 6/1994 | Makower et al. |
| 5,330,445 A | 7/1994 | Haaga |
| 5,333,624 A | 8/1994 | Tovey |
| 5,334,137 A | 8/1994 | Freeman |
| 5,334,216 A | 8/1994 | Vidal et al. |
| 5,342,393 A | 8/1994 | Stack |
| 5,350,399 A | 9/1994 | Erlebacher et al. |
| 5,350,404 A | 9/1994 | Adams et al. |
| 5,366,459 A | 11/1994 | Yoon |
| 5,370,650 A | 12/1994 | Tovey et al. |
| 5,376,376 A | 12/1994 | Li |
| 5,382,899 A | 1/1995 | Funatsu et al. |
| 5,383,896 A | 1/1995 | Gershony et al. |
| 5,383,899 A | 1/1995 | Hammerslag |
| RE34,866 E | 2/1995 | Kensey et al. |
| 5,391,183 A | 2/1995 | Janzen et al. |
| 5,405,360 A | 4/1995 | Tovey |
| 5,409,499 A | 4/1995 | Yi |
| 5,417,651 A | 5/1995 | Guena et al. |
| 5,419,760 A | 5/1995 | Narciso |
| 5,419,765 A | 5/1995 | Weldon et al. |
| 5,425,757 A | 6/1995 | Tiefenbrun et al. |
| 5,431,639 A | 7/1995 | Shaw |
| 5,433,729 A | 7/1995 | Adams et al. |
| 5,443,463 A | 8/1995 | Stern et al. |
| 5,443,481 A | 8/1995 | Lee |
| 5,443,500 A | 8/1995 | Sigwart |
| 5,447,502 A | 9/1995 | Haaga |
| 5,449,375 A | 9/1995 | Vidal et al. |
| 5,454,834 A | 10/1995 | Boebel et al. |
| 5,480,388 A | 1/1996 | Zadini et al. |
| 5,486,195 A | 1/1996 | Myers et al. |
| 5,529,577 A | 6/1996 | Hammerslag |
| 5,531,759 A | 7/1996 | Kensey et al. |
| 5,536,251 A | 7/1996 | Evard et al. |
| 5,556,385 A | 9/1996 | Andersen |
| 5,562,617 A | 10/1996 | Finch, Jr. et al. |
| 5,571,181 A | 11/1996 | Li |
| 5,573,518 A | 11/1996 | Haaga |
| 5,584,801 A | 12/1996 | Kuroyanagi et al. |
| 5,591,189 A | 1/1997 | Yoon |
| 5,591,204 A | 1/1997 | Janzen et al. |
| 5,593,422 A | 1/1997 | Muijs Van de Moer et al. |
| 5,601,602 A | 2/1997 | Fowler |
| 5,609,604 A | 3/1997 | Schwemberger et al. |
| 5,613,974 A | 3/1997 | Andreas et al. |
| 5,618,297 A | 4/1997 | Hart et al. |
| 5,620,456 A | 4/1997 | Sauer et al. |
| 5,620,461 A | 4/1997 | Muijs Van De Moer et al. |
| 5,624,454 A | 4/1997 | Palti et al. |
| 5,626,601 A | 5/1997 | Gershony et al. |
| 5,630,833 A | 5/1997 | Katsaros et al. |
| 5,634,936 A | 6/1997 | Linden et al. |
| 5,643,318 A | 7/1997 | Tsukernik et al. |
| 5,643,596 A | 7/1997 | Pruss et al. |
| 5,645,553 A | 7/1997 | Kolesa et al. |
| 5,645,566 A | 7/1997 | Brenneman et al. |
| 5,645,568 A | 7/1997 | Chervitz et al. |
| 5,645,849 A | 7/1997 | Pruss et al. |
| 5,649,959 A | 7/1997 | Hannam et al. |
| 5,653,730 A | 8/1997 | Hammerslag |
| 5,665,106 A | 9/1997 | Hammerslag |
| 5,665,107 A | 9/1997 | Hammerslag |
| 5,690,674 A | 11/1997 | Diaz |
| 5,697,942 A | 12/1997 | Palti et al. |
| 5,702,421 A | 12/1997 | Schneidt |
| 5,713,859 A | 2/1998 | Finch, Jr. et al. |
| 5,716,375 A | 2/1998 | Fowler |
| 5,718,725 A | 2/1998 | Sterman et al. |
| 5,723,005 A | 3/1998 | Herrick |
| 5,725,498 A | 3/1998 | Janzen et al. |
| 5,725,551 A | 3/1998 | Myers et al. |
| 5,733,294 A | 3/1998 | Forber et al. |
| 5,741,223 A | 4/1998 | Janzen et al. |
| 5,759,194 A | 6/1998 | Hammerslag |
| 5,766,183 A | 6/1998 | Sauer |
| 5,782,860 A | 7/1998 | Epstein et al. |
| 5,782,861 A | 7/1998 | Cragg et al. |
| 5,792,173 A | 8/1998 | Breen et al. |
| 5,797,944 A | 8/1998 | Nobles et al. |
| 5,797,960 A | 8/1998 | Stevens et al. |
| 5,810,810 A | 9/1998 | Tay et al. |

(56) References Cited

U.S. PATENT DOCUMENTS

| | | |
|---|---|---|
| 5,810,884 A | 9/1998 | Kim |
| 5,814,066 A | 9/1998 | Spotnitz |
| 5,814,097 A | 9/1998 | Sterman et al. |
| 5,830,130 A | 11/1998 | Janzen et al. |
| 5,830,171 A | 11/1998 | Wallace |
| 5,830,222 A | 11/1998 | Makower |
| 5,843,108 A | 12/1998 | Samuels |
| 5,843,124 A | 12/1998 | Hammerslag |
| 5,861,003 A | 1/1999 | Latson et al. |
| 5,861,004 A | 1/1999 | Kensey et al. |
| 5,865,791 A | 2/1999 | Whayne et al. |
| 5,868,773 A | 2/1999 | Danks et al. |
| 5,868,778 A | 2/1999 | Gershony et al. |
| 5,879,403 A | 3/1999 | Ostiguy et al. |
| 5,885,258 A | 3/1999 | Sachdeva et al. |
| 5,904,703 A | 5/1999 | Gilson |
| 5,906,631 A | 5/1999 | Imran |
| 5,941,897 A | 8/1999 | Myers |
| 5,948,425 A | 9/1999 | Janzen et al. |
| 5,957,952 A | 9/1999 | Gershony et al. |
| 5,964,782 A | 10/1999 | Lafontaine et al. |
| 5,972,034 A | 10/1999 | Hofmann et al. |
| 5,976,174 A | 11/1999 | Ruiz |
| 5,978,704 A | 11/1999 | Ideker et al. |
| 5,978,705 A | 11/1999 | KenKnight et al. |
| 5,979,446 A | 11/1999 | Loy |
| 5,984,917 A | 11/1999 | Fleischman et al. |
| 5,984,950 A | 11/1999 | Cragg et al. |
| 5,997,580 A | 12/1999 | Mastrorio et al. |
| 6,001,110 A | 12/1999 | Adams |
| 6,004,347 A | 12/1999 | McNamara et al. |
| 6,017,359 A | 1/2000 | Gershony et al. |
| 6,024,755 A | 2/2000 | Addis |
| 6,027,470 A | 2/2000 | Mendius |
| 6,042,592 A | 3/2000 | Schmitt |
| 6,042,601 A | 3/2000 | Smith |
| 6,045,569 A | 4/2000 | Kensey et al. |
| 6,045,570 A | 4/2000 | Epstein et al. |
| 6,056,769 A | 5/2000 | Epstein et al. |
| 6,056,770 A | 5/2000 | Epstein et al. |
| 6,063,099 A | 5/2000 | Danks et al. |
| 6,071,281 A | 6/2000 | Burnside et al. |
| 6,071,300 A | 6/2000 | Brenneman et al. |
| 6,079,414 A | 6/2000 | Roth et al. |
| 6,085,119 A | 7/2000 | Scheiner et al. |
| 6,090,130 A | 7/2000 | Nash et al. |
| 6,090,135 A | 7/2000 | Plaia et al. |
| 6,099,506 A | 8/2000 | Macoviak et al. |
| 6,110,184 A | 8/2000 | Weadock |
| 6,113,608 A | 9/2000 | Monroe et al. |
| 6,126,675 A | 10/2000 | Shchervinsky et al. |
| 6,132,438 A | 10/2000 | Fleischman et al. |
| 6,149,684 A | 11/2000 | Herrick |
| 6,152,144 A | 11/2000 | Lesh et al. |
| 6,156,016 A | 12/2000 | Maginot |
| 6,183,496 B1 | 2/2001 | Urbanski |
| 6,193,733 B1 | 2/2001 | Adams |
| 6,197,042 B1 | 3/2001 | Ginn et al. |
| 6,206,893 B1 | 3/2001 | Klein et al. |
| 6,206,907 B1 | 3/2001 | Marino et al. |
| 6,210,366 B1 | 4/2001 | Sanfilippo |
| 6,224,618 B1 | 5/2001 | Gordon |
| 6,224,630 B1 * | 5/2001 | Bao et al. ............ 623/17.16 |
| 6,231,561 B1 | 5/2001 | Frazier et al. |
| 6,237,605 B1 | 5/2001 | Vaska et al. |
| 6,238,363 B1 | 5/2001 | Kurihashi |
| 6,241,728 B1 | 6/2001 | Gaiser et al. |
| 6,254,562 B1 | 7/2001 | Fouere |
| 6,258,113 B1 | 7/2001 | Adams et al. |
| 6,261,309 B1 | 7/2001 | Urbanski |
| 6,264,673 B1 | 7/2001 | Egnelov et al. |
| 6,277,140 B2 | 8/2001 | Ginn et al. |
| 6,280,477 B1 | 8/2001 | Mastrorio et al. |
| 6,287,323 B1 | 9/2001 | Hammerslag et al. |
| 6,296,657 B1 | 10/2001 | Brucker |
| 6,306,114 B1 | 10/2001 | Freeman et al. |
| 6,337,995 B1 | 1/2002 | Mower |
| 6,357,443 B1 | 3/2002 | Loy |
| 6,375,662 B1 | 4/2002 | Schmitt |
| 6,375,671 B1 | 4/2002 | Kobayashi et al. |
| 6,379,366 B1 | 4/2002 | Fleischman et al. |
| 6,383,204 B1 | 5/2002 | Ferrera et al. |
| 6,391,048 B1 | 5/2002 | Ginn et al. |
| 6,402,770 B1 | 6/2002 | Jessen |
| 6,423,051 B1 | 7/2002 | Kaplan et al. |
| 6,425,911 B1 | 7/2002 | Akerfeldt et al. |
| 6,436,088 B2 | 8/2002 | Frazier et al. |
| 6,436,119 B1 | 8/2002 | Erb et al. |
| 6,461,364 B1 | 10/2002 | Ginn et al. |
| 6,463,317 B1 | 10/2002 | Kucharczyk et al. |
| 6,464,712 B1 | 10/2002 | Epstein et al. |
| 6,474,340 B1 | 11/2002 | Vaska et al. |
| 6,482,175 B1 | 11/2002 | Walker |
| 6,485,407 B2 | 11/2002 | Alferness et al. |
| 6,488,689 B1 | 12/2002 | Kaplan et al. |
| 6,494,848 B1 | 12/2002 | Sommercorn et al. |
| 6,497,651 B1 | 12/2002 | Kan et al. |
| 6,502,575 B1 | 1/2003 | Jacobs et al. |
| 6,508,828 B1 | 1/2003 | Akerfeldt et al. |
| 6,511,508 B1 | 1/2003 | Shahinpoor et al. |
| 6,517,575 B1 | 2/2003 | Yang et al. |
| 6,537,299 B1 | 3/2003 | Hogendijk et al. |
| 6,546,270 B1 | 4/2003 | Goldin et al. |
| 6,547,806 B1 | 4/2003 | Ding |
| 6,549,812 B1 | 4/2003 | Smits |
| 6,551,303 B1 | 4/2003 | Van Tassel et al. |
| 6,561,969 B2 | 5/2003 | Frazier et al. |
| 6,589,269 B2 | 7/2003 | Zhu et al. |
| 6,596,012 B2 | 7/2003 | Akerfeldt et al. |
| 6,610,026 B2 | 8/2003 | Cragg et al. |
| 6,612,069 B2 | 9/2003 | Locke et al. |
| 6,613,059 B2 | 9/2003 | Schatler et al. |
| 6,623,509 B2 * | 9/2003 | Ginn ................ 606/213 |
| 6,623,510 B2 | 9/2003 | Carley et al. |
| 6,626,918 B1 | 9/2003 | Ginn et al. |
| 6,629,533 B1 | 10/2003 | Webb et al. |
| 6,632,238 B2 | 10/2003 | Ginn et al. |
| 6,632,239 B2 | 10/2003 | Snyder et al. |
| 6,645,205 B2 | 11/2003 | Ginn |
| 6,645,225 B1 * | 11/2003 | Atkinson ............ 606/213 |
| 6,652,555 B1 | 11/2003 | Van Tassel et al. |
| 6,652,556 B1 | 11/2003 | VanTassel et al. |
| 6,656,207 B2 | 12/2003 | Epstein et al. |
| 6,663,655 B2 | 12/2003 | Ginn et al. |
| 6,666,861 B1 | 12/2003 | Grabek |
| 6,669,687 B1 | 12/2003 | Saadat |
| 6,669,714 B2 | 12/2003 | Coleman et al. |
| 6,679,904 B2 | 1/2004 | Gleeson et al. |
| 6,681,773 B2 | 1/2004 | Murphy et al. |
| 6,682,489 B2 | 1/2004 | Tenerz et al. |
| 6,689,150 B1 | 2/2004 | VanTassel et al. |
| 6,699,240 B2 | 3/2004 | Francischelli |
| 6,702,763 B2 | 3/2004 | Murphy et al. |
| 6,702,835 B2 | 3/2004 | Ginn |
| 6,712,837 B2 | 3/2004 | Akerfeldt et al. |
| 6,716,234 B2 | 4/2004 | Grafton et al. |
| 6,719,777 B2 | 4/2004 | Ginn et al. |
| 6,726,696 B1 | 4/2004 | Houser et al. |
| 6,730,020 B2 | 5/2004 | Peng et al. |
| 6,730,108 B2 | 5/2004 | Van Tassel et al. |
| 6,732,739 B2 | 5/2004 | Cosgrove |
| 6,736,815 B2 | 5/2004 | Ginn |
| 6,743,259 B2 | 6/2004 | Ginn |
| 6,746,461 B2 | 6/2004 | Fry |
| 6,770,026 B2 | 8/2004 | Kan et al. |
| 6,776,784 B2 | 8/2004 | Ginn |
| 6,780,197 B2 | 8/2004 | Roe et al. |
| 6,786,905 B2 | 9/2004 | Swanson et al. |
| 6,786,915 B2 | 9/2004 | Akerfeldt et al. |
| 6,790,218 B2 | 9/2004 | Jayaraman |
| 6,793,664 B2 | 9/2004 | Mazzocchi et al. |
| 6,830,576 B2 | 12/2004 | Fleischman et al. |
| 6,846,319 B2 | 1/2005 | Ginn et al. |
| 6,860,895 B1 | 3/2005 | Akerfeldt et al. |

(56) References Cited

U.S. PATENT DOCUMENTS

| | | |
|---|---|---|
| 6,890,343 B2 | 5/2005 | Ginn et al. |
| 6,896,692 B2 | 5/2005 | Ginn et al. |
| 6,941,169 B2 | 9/2005 | Pappu |
| 6,949,113 B2 | 9/2005 | Van Tassel et al. |
| 6,959,711 B2 | 11/2005 | Murphy et al. |
| 6,969,397 B2 | 11/2005 | Ginn |
| 6,970,742 B2 | 11/2005 | Mann et al. |
| 6,994,092 B2 | 2/2006 | van der Burg et al. |
| 6,994,093 B2 | 2/2006 | Murphy et al. |
| 7,001,398 B2 | 2/2006 | Carley et al. |
| 7,008,439 B1 | 3/2006 | Janzen et al. |
| 7,011,671 B2 | 3/2006 | Welch |
| 7,025,773 B2 | 4/2006 | Gittings et al. |
| 7,025,776 B1* | 4/2006 | Houser et al. .................. 606/213 |
| 7,029,838 B2 | 4/2006 | Williams et al. |
| 7,044,134 B2 | 5/2006 | Khairkhahan et al. |
| 7,052,492 B2 | 5/2006 | Swanson et al. |
| 7,052,829 B2 | 5/2006 | Williams et al. |
| 7,056,294 B2 | 6/2006 | Khairkhahan et al. |
| 7,083,614 B2 | 8/2006 | Fjield et al. |
| 7,083,635 B2 | 8/2006 | Ginn |
| 7,112,219 B2 | 9/2006 | Vidlund et al. |
| 7,115,095 B2 | 10/2006 | Eigler et al. |
| 7,128,073 B1 | 10/2006 | van der Burg et al. |
| 7,128,740 B2 | 10/2006 | Jacobs et al. |
| 7,137,953 B2 | 11/2006 | Eigler et al. |
| 7,144,411 B2 | 12/2006 | Ginn et al. |
| 7,152,605 B2 | 12/2006 | Khairkhahan et al. |
| 7,169,164 B2 | 1/2007 | Borillo et al. |
| 7,182,771 B1 | 2/2007 | Houser et al. |
| 7,189,199 B2 | 3/2007 | McCarthy et al. |
| 7,192,439 B2 | 3/2007 | Khairkhahan et al. |
| 7,211,048 B1 | 5/2007 | Najafi et |
| 7,217,284 B2 | 5/2007 | Houser et al. |
| 7,226,458 B2 | 6/2007 | Kaplan et al. |
| 7,250,057 B2 | 7/2007 | Forsberg |
| 7,288,090 B2 | 10/2007 | Swanson |
| 7,293,562 B2 | 11/2007 | Malecki et al. |
| 7,297,144 B2 | 11/2007 | Fleischman et al. |
| 7,318,829 B2 | 1/2008 | Kaplan et al. |
| 7,326,201 B2 | 2/2008 | Fjield et al. |
| 7,327,862 B2 | 2/2008 | Murphy et al. |
| 7,335,219 B1 | 2/2008 | Ashby et al. |
| 7,335,220 B2 | 2/2008 | Khosravi et al. |
| 7,344,543 B2 | 3/2008 | Sra |
| 7,344,553 B2 | 3/2008 | Opolski et al. |
| 7,361,183 B2 | 4/2008 | Ginn |
| 7,427,279 B2 | 9/2008 | Frazier et al. |
| 7,429,264 B2 | 9/2008 | Melkent et al. |
| 7,455,669 B2 | 11/2008 | Swanson |
| 7,483,743 B2 | 1/2009 | Mann et al. |
| 7,575,586 B2 | 8/2009 | Berg et al. |
| 7,931,671 B2 | 4/2011 | Tenerz |
| 8,105,352 B2 | 1/2012 | Egnelöv |
| 8,118,831 B2 | 2/2012 | Egnelöv et al. |
| 8,157,836 B2 | 4/2012 | Adams |
| 2001/0003158 A1 | 6/2001 | Kensey et al. |
| 2001/0003986 A1 | 6/2001 | Cosgrove |
| 2001/0007077 A1 | 7/2001 | Ginn et al. |
| 2001/0034509 A1 | 10/2001 | Cragg et al. |
| 2002/0019648 A1 | 2/2002 | Akerfeldt et al. |
| 2002/0022860 A1 | 2/2002 | Borillo et al. |
| 2002/0026208 A1 | 2/2002 | Roe et al. |
| 2002/0032454 A1 | 3/2002 | Durgin et al. |
| 2002/0049457 A1 | 4/2002 | Kaplan et al. |
| 2002/0058925 A1 | 5/2002 | Kaplan et al. |
| 2002/0065512 A1 | 5/2002 | Fjield et al. |
| 2002/0072768 A1 | 6/2002 | Ginn |
| 2002/0077656 A1 | 6/2002 | Ginn et al. |
| 2002/0077657 A1 | 6/2002 | Ginn et al. |
| 2002/0077658 A1 | 6/2002 | Ginn |
| 2002/0082641 A1 | 6/2002 | Ginn et al. |
| 2002/0087151 A1 | 7/2002 | Mody et al. |
| 2002/0099390 A1 | 7/2002 | Kaplan et al. |
| 2002/0103492 A1 | 8/2002 | Kaplan et al. |
| 2002/0111636 A1 | 8/2002 | Fleischman et al. |
| 2002/0111637 A1 | 8/2002 | Kaplan et al. |
| 2002/0111647 A1 | 8/2002 | Khairkhahan et al. |
| 2002/0128640 A1 | 9/2002 | Swanson |
| 2002/0133193 A1 | 9/2002 | Ginn et al. |
| 2002/0133227 A1 | 9/2002 | Murphy et al. |
| 2002/0147456 A1 | 10/2002 | Diduch et al. |
| 2002/0147461 A1 | 10/2002 | Aldrich et al. |
| 2002/0183823 A1 | 12/2002 | Pappu |
| 2002/0188318 A1 | 12/2002 | Carley et al. |
| 2003/0023141 A1 | 1/2003 | Stelzer et al. |
| 2003/0023262 A1 | 1/2003 | Welch |
| 2003/0023266 A1 | 1/2003 | Borillo et al. |
| 2003/0023267 A1 | 1/2003 | Ginn |
| 2003/0032858 A1 | 2/2003 | Ginn et al. |
| 2003/0045896 A1 | 3/2003 | Murphy et al. |
| 2003/0050630 A1 | 3/2003 | Mody et al. |
| 2003/0050632 A1 | 3/2003 | Fjield et al. |
| 2003/0050659 A1 | 3/2003 | Murphy et al. |
| 2003/0057156 A1 | 3/2003 | Peterson et al. |
| 2003/0065339 A1 | 4/2003 | Snyder et al. |
| 2003/0078598 A1 | 4/2003 | Ginn et al. |
| 2003/0078616 A1 | 4/2003 | Ginn et al. |
| 2003/0079753 A1 | 5/2003 | Vaska et al. |
| 2003/0083542 A1 | 5/2003 | Alferness et al. |
| 2003/0120337 A1 | 6/2003 | Van Tassel et al. |
| 2003/0125604 A1 | 7/2003 | Kochamba et al. |
| 2003/0158464 A1 | 8/2003 | Bertolero |
| 2003/0163143 A1* | 8/2003 | Wakabayashi ................ 606/148 |
| 2003/0163146 A1 | 8/2003 | Epstein et al. |
| 2003/0178033 A1 | 9/2003 | Cosgrove |
| 2003/0181901 A1 | 9/2003 | Maguire et al. |
| 2003/0181940 A1 | 9/2003 | Murphy et al. |
| 2003/0181942 A1 | 9/2003 | Sutton et al. |
| 2003/0181945 A1 | 9/2003 | Opolski et al. |
| 2003/0187362 A1 | 10/2003 | Murphy et al. |
| 2003/0191462 A1 | 10/2003 | Jacobs et al. |
| 2003/0191526 A1 | 10/2003 | Van Tassel et al. |
| 2003/0195560 A1 | 10/2003 | Ginn |
| 2003/0195561 A1 | 10/2003 | Carley et al. |
| 2003/0220667 A1 | 11/2003 | van der Burg et al. |
| 2003/0225443 A1 | 12/2003 | Kiran et al. |
| 2004/0009289 A1 | 1/2004 | Carley et al. |
| 2004/0010273 A1 | 1/2004 | Diduch et al. |
| 2004/0010285 A1 | 1/2004 | Carley et al. |
| 2004/0030335 A1 | 2/2004 | Zenati et al. |
| 2004/0034366 A1 | 2/2004 | van der Burg et al. |
| 2004/0039414 A1 | 2/2004 | Carley et al. |
| 2004/0044361 A1 | 3/2004 | Frazier et al. |
| 2004/0049210 A1 | 3/2004 | Van Tassel et al. |
| 2004/0064014 A1 | 4/2004 | Melvin et al. |
| 2004/0064138 A1 | 4/2004 | Grabek |
| 2004/0073241 A1 | 4/2004 | Barry et al. |
| 2004/0093025 A1 | 5/2004 | Egnelöv |
| 2004/0098031 A1 | 5/2004 | van der Burg et al. |
| 2004/0098042 A1 | 5/2004 | Devellian et al. |
| 2004/0122467 A1 | 6/2004 | VanTassel et al. |
| 2004/0127935 A1 | 7/2004 | VanTassel et al. |
| 2004/0127940 A1 | 7/2004 | Ginn et al. |
| 2004/0147969 A1 | 7/2004 | Mann et al. |
| 2004/0148019 A1 | 7/2004 | Vidlund et al. |
| 2004/0158287 A1* | 8/2004 | Cragg et al. .................. 606/213 |
| 2004/0167580 A1 | 8/2004 | Mann et al. |
| 2004/0175522 A1 | 9/2004 | Tajima |
| 2004/0186486 A1 | 9/2004 | Roue et al. |
| 2004/0215230 A1 | 10/2004 | Frazier et al. |
| 2004/0220560 A1 | 11/2004 | Briscoe |
| 2004/0225212 A1 | 11/2004 | Okerlund et al. |
| 2004/0232597 A1 | 11/2004 | Sjostedt et al. |
| 2004/0249342 A1 | 12/2004 | Khosravi et al. |
| 2004/0249412 A1 | 12/2004 | Snow et al. |
| 2004/0267193 A1 | 12/2004 | Bagaoisan et al. |
| 2004/0267307 A1 | 12/2004 | Bagaoisan et al. |
| 2004/0267308 A1 | 12/2004 | Bagaoisan et al. |
| 2005/0004641 A1 | 1/2005 | Pappu |
| 2005/0004652 A1 | 1/2005 | van der Burg et al. |
| 2005/0010252 A1 | 1/2005 | Ideker |
| 2005/0021016 A1 | 1/2005 | Malecki et al. |
| 2005/0033285 A1 | 2/2005 | Swanson et al. |

(56) References Cited

U.S. PATENT DOCUMENTS

| | | |
|---|---|---|
| 2005/0033287 A1 | 2/2005 | Sra |
| 2005/0033321 A1 | 2/2005 | Fleischman et al. |
| 2005/0038470 A1 | 2/2005 | van der Burg et al. |
| 2005/0049573 A1 | 3/2005 | VanTassel et al. |
| 2005/0049681 A1 | 3/2005 | Greenhalgh et al. |
| 2005/0070952 A1 | 3/2005 | Devellian |
| 2005/0085805 A1 | 4/2005 | Swanson |
| 2005/0085854 A1 | 4/2005 | Ginn |
| 2005/0085856 A1 | 4/2005 | Ginn |
| 2005/0113861 A1 | 5/2005 | Corcoran et al. |
| 2005/0113868 A1 | 5/2005 | Devellian et al. |
| 2005/0119695 A1 | 6/2005 | Carley et al. |
| 2005/0131503 A1 | 6/2005 | Solem |
| 2005/0149068 A1 | 7/2005 | Williams et al. |
| 2005/0149069 A1 | 7/2005 | Bertolero et al. |
| 2005/0149115 A1 | 7/2005 | Roue et al. |
| 2005/0149117 A1 | 7/2005 | Khosravi et al. |
| 2005/0154404 A1 | 7/2005 | Liddicoat et al. |
| 2005/0169974 A1 | 8/2005 | Tenerz et al. |
| 2005/0177180 A1 | 8/2005 | Kaganov et al. |
| 2005/0177182 A1 | 8/2005 | van der Berg et al. |
| 2005/0177183 A1 | 8/2005 | Thorne et al. |
| 2005/0177189 A1 | 8/2005 | Ginn et al. |
| 2005/0197716 A1 | 9/2005 | Sharkey et al. |
| 2005/0203410 A1 | 9/2005 | Jenkins |
| 2005/0203568 A1 | 9/2005 | van der Burg et al. |
| 2005/0222533 A1 | 10/2005 | Chanduszko et al. |
| 2005/0222614 A1 | 10/2005 | Ginn et al. |
| 2005/0234540 A1 | 10/2005 | Peavey et al. |
| 2005/0234543 A1 | 10/2005 | Glaser et al. |
| 2005/0245876 A1 | 11/2005 | Khosravi et al. |
| 2005/0245963 A1 | 11/2005 | Kida et al. |
| 2005/0267521 A1 | 12/2005 | Forsberg |
| 2005/0267528 A1 | 12/2005 | Ginn et al. |
| 2005/0273129 A1 | 12/2005 | Michels et al. |
| 2005/0273137 A1 | 12/2005 | Ginn |
| 2005/0277959 A1 | 12/2005 | Cosgrove et al. |
| 2005/0283187 A1 | 12/2005 | Longson |
| 2006/0004352 A1 | 1/2006 | Vaska et al. |
| 2006/0004388 A1 | 1/2006 | Whayne et al. |
| 2006/0009715 A1 | 1/2006 | Khairkhahan et al. |
| 2006/0009753 A1 | 1/2006 | Fjield et al. |
| 2006/0020162 A1 | 1/2006 | Whayne et al. |
| 2006/0020271 A1 | 1/2006 | Stewart et al. |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0074397 A1 | 4/2006 | Shimada |
| 2006/0074410 A1 | 4/2006 | Malecki et al. |
| 2006/0099238 A1* | 5/2006 | Khosravi et al. ............ 424/423 |
| 2006/0100664 A1 | 5/2006 | Pai et al. |
| 2006/0106442 A1 | 5/2006 | Richardson et al. |
| 2006/0135989 A1 | 6/2006 | Carley et al. |
| 2006/0136051 A1* | 6/2006 | Furst et al. ................. 623/1.42 |
| 2006/0149314 A1 | 7/2006 | Borillo et al. |
| 2006/0167484 A1 | 7/2006 | Carley et al. |
| 2006/0178694 A1 | 8/2006 | Greenhalgh et al. |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206109 A1 | 9/2006 | Swanson |
| 2006/0206121 A1 | 9/2006 | Chin et al. |
| 2006/0206148 A1 | 9/2006 | Khairkhahan et al. |
| 2006/0229672 A1 | 10/2006 | Forsberg |
| 2006/0229674 A1 | 10/2006 | Forsberg |
| 2006/0247672 A1 | 11/2006 | Vidlund et al. |
| 2006/0247680 A1 | 11/2006 | Amplatz et al. |
| 2006/0253037 A1 | 11/2006 | Ginn et al. |
| 2006/0253072 A1 | 11/2006 | Pai et al. |
| 2006/0253129 A1 | 11/2006 | Liddicoat et al. |
| 2006/0263418 A1 | 11/2006 | White |
| 2006/0265007 A1 | 11/2006 | White et al. |
| 2006/0271032 A1 | 11/2006 | Chin et al. |
| 2006/0271089 A1 | 11/2006 | Alejandro et al. |
| 2006/0287661 A1 | 12/2006 | Bolduc et al. |
| 2006/0287674 A1 | 12/2006 | Ginn et al. |
| 2007/0004984 A1 | 1/2007 | Crum et al. |
| 2007/0016228 A1 | 1/2007 | Salas |
| 2007/0032734 A1 | 2/2007 | Najafi et al. |
| 2007/0032823 A1 | 2/2007 | Tegg |
| 2007/0032824 A1 | 2/2007 | Terwey |
| 2007/0043344 A1 | 2/2007 | Mcauley |
| 2007/0060950 A1 | 3/2007 | Khosravi et al. |
| 2007/0060951 A1 | 3/2007 | Shannon |
| 2007/0066993 A1 | 3/2007 | Kreidler |
| 2007/0073313 A1 | 3/2007 | Liddicoat et al. |
| 2007/0073345 A1 | 3/2007 | Pipenhagen et al. |
| 2007/0083227 A1 | 4/2007 | van der Burg et al. |
| 2007/0083230 A1 | 4/2007 | Javois |
| 2007/0123817 A1 | 5/2007 | Khosravi et al. |
| 2007/0129758 A1 | 6/2007 | Saadat |
| 2007/0149988 A1 | 6/2007 | Michler et al. |
| 2007/0156010 A1 | 7/2007 | Aboul-hosn |
| 2007/0156084 A1 | 7/2007 | Belhe et al. |
| 2007/0156123 A1 | 7/2007 | Moll et al. |
| 2007/0162048 A1 | 7/2007 | Quinn et al. |
| 2007/0179345 A1 | 8/2007 | Santilli |
| 2007/0185530 A1 | 8/2007 | Chin-chen et al. |
| 2007/0198060 A1 | 8/2007 | Devellian et al. |
| 2007/0208329 A1 | 9/2007 | Ward et al. |
| 2007/0219546 A1 | 9/2007 | Mody et al. |
| 2007/0233226 A1 | 10/2007 | Kochamba et al. |
| 2007/0244476 A1 | 10/2007 | Kochamba et al. |
| 2007/0255314 A1 | 11/2007 | Forsberg |
| 2007/0260278 A1 | 11/2007 | Wheeler et al. |
| 2007/0265641 A1 | 11/2007 | Roue et al. |
| 2007/0270891 A1 | 11/2007 | Mcguckin |
| 2007/0276433 A1 | 11/2007 | Huss |
| 2007/0287999 A1 | 12/2007 | Malecki et al. |
| 2008/0004658 A1 | 1/2008 | Malecki et al. |
| 2008/0009843 A1 | 1/2008 | De La |
| 2008/0015569 A1 | 1/2008 | Saadat et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0045946 A1 | 2/2008 | Vaska |
| 2008/0058862 A1 | 3/2008 | Khosravi et al. |
| 2008/0058864 A1 | 3/2008 | Bagaoisan et al. |
| 2008/0071311 A1 | 3/2008 | White et al. |
| 2008/0082122 A1 | 4/2008 | Khosravi et al. |
| 2008/0097488 A1 | 4/2008 | Fleischman et al. |
| 2008/0097521 A1 | 4/2008 | Khosravi et al. |
| 2008/0109030 A1 | 5/2008 | Houser et al. |
| 2008/0114394 A1 | 5/2008 | Houser et al. |
| 2008/0125795 A1 | 5/2008 | Kaplan et al. |
| 2008/0125848 A1 | 5/2008 | Kusleika et al. |
| 2008/0132602 A1 | 6/2008 | Rizk et al. |
| 2008/0147097 A1 | 6/2008 | Liddicoat et al. |
| 2008/0167713 A1 | 7/2008 | Bolling |
| 2008/0167750 A1 | 7/2008 | Stahler et al. |
| 2008/0221593 A1 | 9/2008 | Liddicoat et al. |
| 2008/0243111 A1 | 10/2008 | Gammie et al. |
| 2008/0243183 A1 | 10/2008 | Miller et al. |
| 2008/0249397 A1 | 10/2008 | Kapadia |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0294088 A1 | 11/2008 | Solem et al. |
| 2008/0294175 A1 | 11/2008 | Bardsley et al. |
| 2008/0312664 A1 | 12/2008 | Bardsley et al. |
| 2008/0312676 A1 | 12/2008 | Solem |
| 2009/0005674 A1 | 1/2009 | Saadat et al. |
| 2009/0005777 A1 | 1/2009 | Houser et al. |
| 2009/0012354 A1 | 1/2009 | Wood |
| 2009/0012545 A1 | 1/2009 | Williamson, IV et al. |
| 2009/0088793 A1 | 4/2009 | Bagaoisan et al. |
| 2009/0112257 A1 | 4/2009 | Preinitz et al. |
| 2009/0143808 A1 | 6/2009 | Houser et al. |
| 2009/0254121 A1 | 10/2009 | Newth et al. |
| 2010/0312259 A1 | 12/2010 | Houser et al. |
| 2011/0144661 A1 | 6/2011 | Houser et al. |

(56) References Cited

U.S. PATENT DOCUMENTS

FOREIGN PATENT DOCUMENTS

| EP | 0401525 A1 | 12/1990 |
| JP | 2007-516731 A | 6/2007 |
| SU | 782814 | 11/1980 |
| SU | 1088709 | 4/1984 |
| WO | WO 90/01497 A1 | 2/1990 |
| WO | WO 91/15155 A1 | 10/1991 |
| WO | WO 01/97696 A1 | 12/2001 |
| WO | WO 03/096881 A2 | 11/2003 |
| WO | WO 03/096881 A3 | 4/2004 |

OTHER PUBLICATIONS

International search report and written opinion dated Jul. 27, 2011 for PCT Application No. US2010/056059.
Office action dated Jan. 22, 2013 for U.S. Appl. No. 12/563,320.
Office action dated Jan. 24, 2012 for U.S. Appl. No. 12/563,297.
Office action dated Feb. 7, 2005 for U.S. Appl. No. 10/224,659.
Office action dated Mar. 15, 2012 for U.S. Appl. No. 12/561,104.
Office action dated Mar. 17, 2008 for U.S. Appl. No. 11/279,242.
Office action dated Apr. 6, 2009 for U.S. Appl. No. 11/279,242.
Office action dated Apr. 14, 2011 for U.S. Appl. No. 10/831,850.
Office action dated Apr. 19, 2012 for U.S. Appl. No. 12/563,371.
Office action dated May 2, 2007 for U.S. Appl. No. 11/279,242.
Office action dated May 15, 2007 for U.S. Appl. No. 10/785,486.
Office action dated Jun. 18, 2012 for U.S. Appl. No. 12/563,320.
Office action dated Jun. 19, 2012 for U.S. Appl. No. 11/930,111.
Office action dated Jul. 22, 2005 for U.S. Appl. No. 10/224,659.
Office action dated Jul. 26, 2012 for U.S. Appl. No. 12/167,212.
Office action dated Aug. 24, 2012 for U.S. Appl. No. 12/563,297.
Office action dated Sep. 13, 2006 for U.S. Appl. No. 10/785,486.
Office action dated Sep. 23, 2011 for U.S. Appl. No. 11/933,129.
Office action dated Oct. 15, 2008 for U.S. Appl. No. 10/785,486.
Office action dated Nov. 13, 2008 for U.S. Appl. No. 11/279,242.
Office action dated Nov. 29, 2011 for U.S. Appl. No. 12/327,655.
Office action dated Dec. 12, 2007 for U.S. Appl. No. 10/785,486.
U.S. Appl. No. 13/786,375, filed Mar. 5, 2013, Houser et al.
Office action dated Mar. 5, 2013 for U.S. Appl. No. 12/563,297.
Office action dated Mar. 28, 2013 for U.S. Appl. No. 12/757,275.
Office action dated Mar. 29, 2013 for U.S. Appl. No. 12/942,914.
Office action dated Jun. 24, 2013 for U.S. Appl. No. 12/757,275.
Office action dated Aug. 14, 2013 for U.S. Appl. No. 11/279,242.
Office action dated Oct. 7, 2013 for U.S. Appl. No. 12/563,297.
Office action dated Oct. 22, 2013 for U.S. Appl. No. 12/563,338.
Office action dated Nov. 19, 2013 for U.S. Appl. No. 12/942,914.
International Search Report dated Jul. 12, 2004 for PCT/US2004/040933.

* cited by examiner

VASCULAR CLOSURE DEVICES, SYSTEMS, AND METHODS OF USE

RELATED APPLICATIONS

This application is related to and claims the benefit of U.S. Provisional 61/005,435, filed on Dec. 3, 2007, the entirety of which is hereby incorporated by reference herein and made a part of the present specification.

BACKGROUND OF THE INVENTION

1. Field of the Invention

The invention generally relates to medical devices and techniques, and more particularly to cardiovascular tissue closure devices and techniques.

2. Description of the Related Art

In most cardiology and radiology procedures, a catheter is inserted into an artery, such as the femoral artery, through a vascular introducer. When the procedure is complete, the physician removes the catheter from the introducer and then removes the introducer from the arteriotomy in the vessel. The physician then must prevent or limit the amount of blood that leaks through the arteriotomy so that the patient can be discharged. Physicians currently use a number of methods to close the arteriotomy, such as localized compression, sutures, collagen plugs, and adhesives, gels, foams, clips, and similar materials.

In performing localized compression, the physician presses down against the vessel to allow the arteriotomy to naturally clot. This method, however, can take a significant amount of time, and requires the patient to remain immobilized and be kept in the hospital for observation. Clots at the puncture site may also be dislodged. Moreover, the amount of time necessary for the compression can significantly increase depending upon how much heparin, glycoprotein IIb/IIA antagonists, or other anti-clotting agents were used during the procedure. Sutures and collagen plugs can have procedure variability, can require time to close the vessel, and can necessitate a separate deployment device. Adhesives, gels, foams, and clips can have negative cost factors, can necessitate a complicated deployment process, and can have procedure variability.

SUMMARY OF THE INVENTION

A tissue closure system can include a deployment instrument and a sealing element. The deployment instrument can be slidably mounted to and guided by a tubular medical device. The deployment instrument can be advanced over the tubular medical device to the desired location. The sealing element can then be advanced off of the end of the tool. The sealing element can include tissue engaging elements that are configured to automatically close upon deployment to bring together tissue. A slidably attached guided skin (or other tissue) cutter can also be used if desired to facilitate entry of the deployment instrument.

DETAILED DESCRIPTION OF THE PREFERRED EMBODIMENT

The following description provides examples of certain embodiments for purposes of illustration. The inventions as claimed should not be limited to these examples. Moreover, although the examples are provided in the context of vessel closure, the invention also has broad application to other types of tissue closure. U.S. Pat. No. 7,025,776 to Houser et al., the entirety of which is incorporated herein by reference, discloses a variety of additional vessel closure devices and methods with features that can be used in combination with or instead of features of the embodiments disclosed herein.

Figure 1:
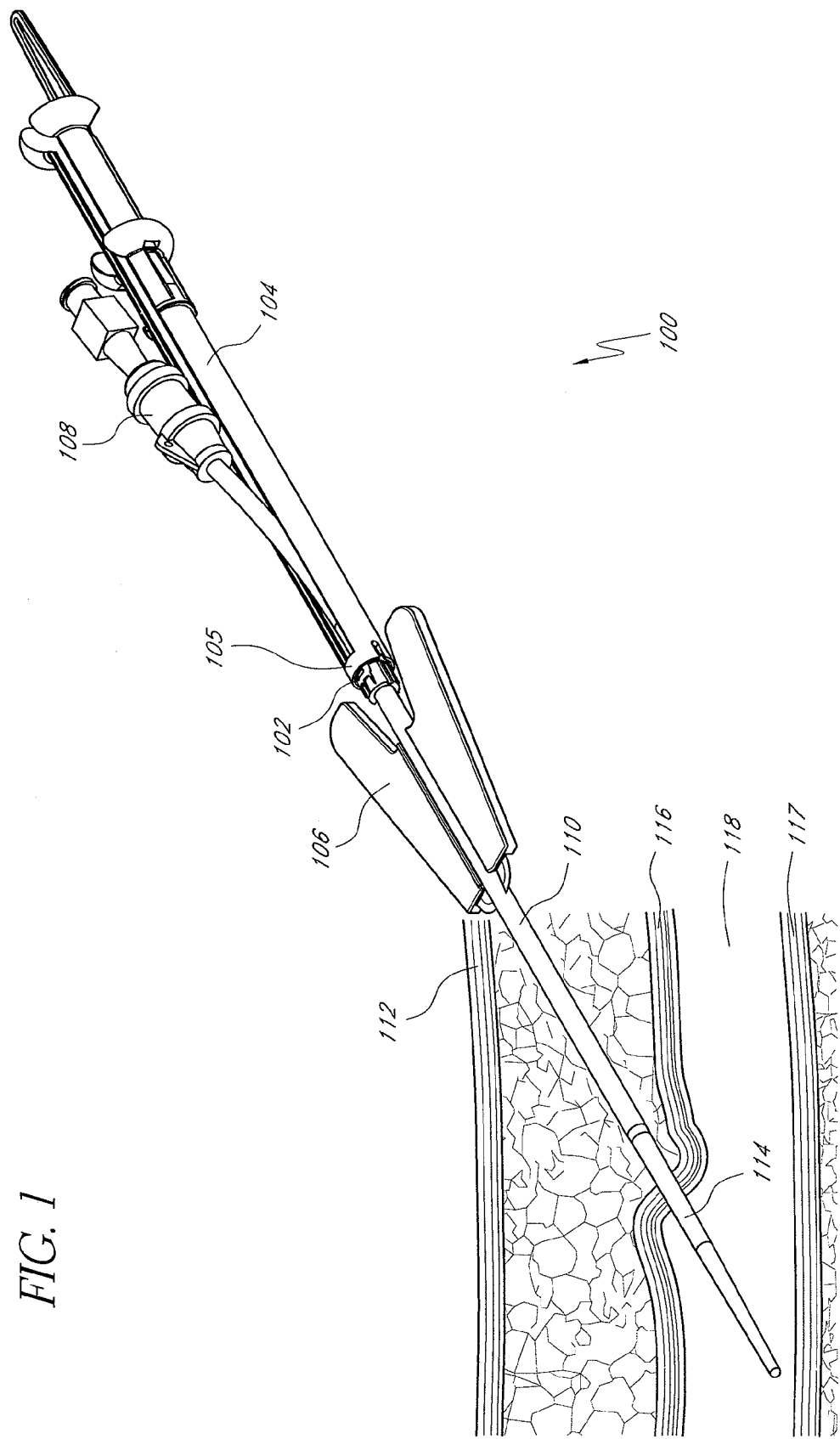
FIG. 1 is a perspective view of an embodiment of a vessel closure system.

Referring to FIG. 1, a vessel closure system 100 can include a vessel closure device such as clip 102 and a deployment or advancement instrument 104. Clip 102 is loaded onto a distal end 105 of deployment instrument 104. The deployment instrument 104 is slidably mounted to or advanced along and generally guided by a vascular introducer 108 or other tubular medical device such as a catheter which has been inserted into a blood vessel 118. In certain embodiments, a narrow opening in the skin initially created for the insertion of the vascular introducer 108 can be expanded or enlarged by a guided slidable tissue cutter 106 to form a percutaneous opening 112 sufficiently large to easily permit passage of the deployment instrument 104 into the body.

The deployment instrument 104 can be guided by a tube section 110 of vascular introducer 108 through the percutaneous opening 112 until it reaches arteriotomy site 114. The deployment instrument 104 is configured to deploy a vascular closure clip 102 to close the arteriotomy 114. The deployment instrument 104 can then be withdrawn.

Figure 2:
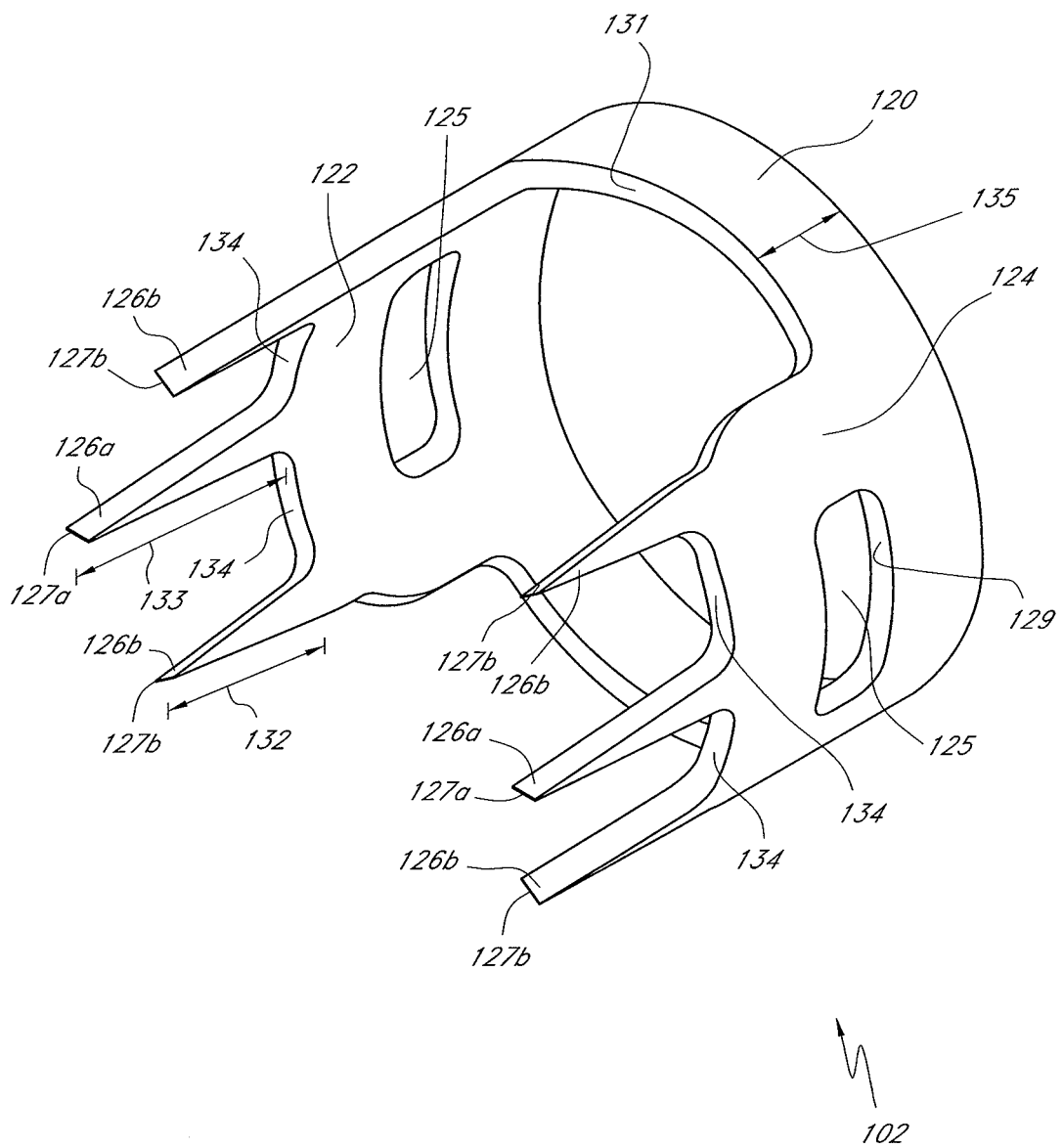
FIG. 2 is a perspective view of an embodiment of a vascular closure clip in an open or pre-deployed configuration.

FIG. 2 is a perspective view of an embodiment of a clip 102 in a pre-deployed or open configuration. Clip 102 can include a base portion 120. Base portion 120 can be generally or completely annular, forming a partial or complete circle. In some embodiments, a base portion 120 with a continuous or substantially continuous circle along its upper edge as illustrated can provide increased strength and resistance to contortion or bending in either or both of the open and closed configurations. A generally circular base portion 120 can allow the tines 126*a-b* to move or bend during the transition between the open and closed configurations while generally resisting a substantial change in shape or orientation of the base portion 120. The height 135 of the base portion 120 can be selected to achieve a desired amount of stiffness or flexibility.

Fingers 122 and 124 can extend from base portion 120 and support a plurality of tissue-engaging elements such as tines 126*a-b*. In some embodiments, as illustrated, the fingers 122 and 124 can be positioned in a substantially opposing arrangement, for example wherein finger 122 is positioned in a substantially diametrically opposite location on the generally circular base 120 from finger 124. As explained below, many other positions and configurations can also be used.

In the illustrated example of FIG. 2, each finger 122, 124 includes three tines: one central tine 126*a* and two outer tines 126*b*. The outer tines 126*b* can be substantially the same length 132 from the respective tips 127*b* to the respective junctures with the forward surface 134 of each finger 122, 124. In some embodiments, the forward surface 134 can be substantially perpendicular to the tines 126*a*, 126*b* and substantially parallel with the plane of the base 120 in the open configuration. Surfaces 134 can generally act as substantially blunt stops to prevent over-insertion of clip 102 into the vessel wall 116. In some embodiments, the length 133 of the central tines 126*a* can be slightly greater than the length 132 of the outer tines 126*b*. This length differential can assist in producing an increased leverage and an increased force along a central line generally bisecting the base 120 between the two opposing central tines 126*a* to help pull generally opposing sides of a tissue slit opening together.

In some embodiments, the lengths 132, 133 can be selected so that the tines 126*a*, 126*b* pierce but do not completely penetrate through a vessel wall 116 of average thickness into the interior region of the vessel 118. For example, the length 132 may be greater than or equal to about 1 mm, and/or the length 132 may be less than or equal to about 4 mm, and the length 133 may be greater than or equal to about 1 mm, and/or the length 133 may be less than or equal to about 5 mm. In some embodiments, the length 132 is about 3 mm, and the length 133 is about 3 mm. In other embodiments, the tines 126*a*, 126*b* can be configured to penetrate the vessel wall, but generally not long enough to contact or penetrate the vessel wall 117 on the opposite side of the vessel 118. The lengths of the tines 126*a*, 126*b* are generally greater than the height 135 of the base portion 120. In the illustrated embodiment, fingers 122 and 124 are generally symmetrical about a central axis. In other embodiments, the fingers 122, 124 can be asymmetrical or include a different number or configuration of tissue-engaging elements.

Fingers 122, 124 can include one or more bend-facilitating regions 125, such as narrowed regions, indentations, articulating joints, or window portions as illustrated. The size, shape, and placement of the bend-facilitating regions 125 can be adjusted to assist in achieving a desired amount of closure force for the clip 102. As illustrated, the contours of the bend-facilitating regions 125 can be generally smooth to avoid additional trauma to the vessel wall. In some embodiments, an upper edge 129 of a bend-facilitating region 125 can be positioned in general alignment with a lower edge 131 of the base portion 120 to maintain a desired height 135 of the base portion 120. As illustrated, the width of the bend-facilitating region can be smaller than the height 135 of the base portion 120.

Figure 3:
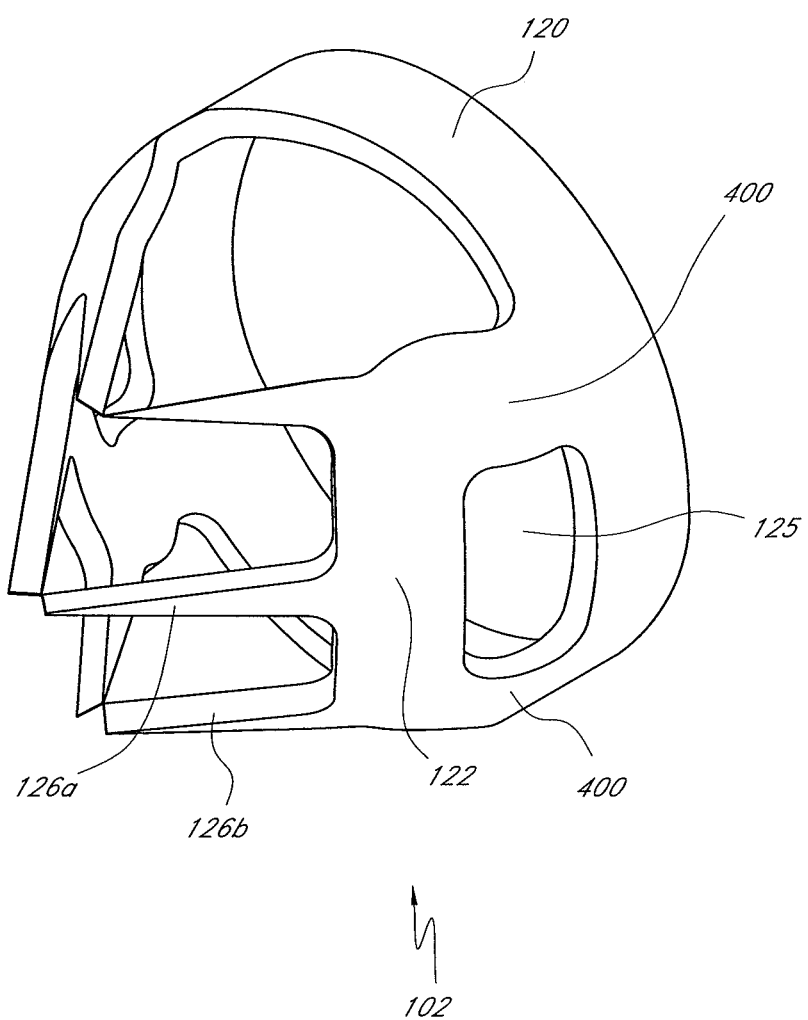
FIG. 3 is a perspective view of the clip of FIG. 2 in a closed or deployed configuration.

FIG. 3 shows a perspective view of clip 102 in a closed or deployed configuration. Clip 102 is preferably biased into a closed configuration. As shown in FIGS. 1 and 2, clip 102 can be temporarily maintained in an open or pre-deployed state by deployment instrument 104 until it is deployed and returns to substantially the same configuration illustrated in FIG. 3. Clip 102 can be configured to automatically close upon deployment to close the arteriotomy. In certain embodiments, the closing of clip 102 can be accomplished substantially via changes in flexion regions 400. In some embodiments, the dimensions, shape, and/or orientation of other portions of clip 102 can remain substantially unchanged between the pre-deployed and deployed states.

Figure 4:
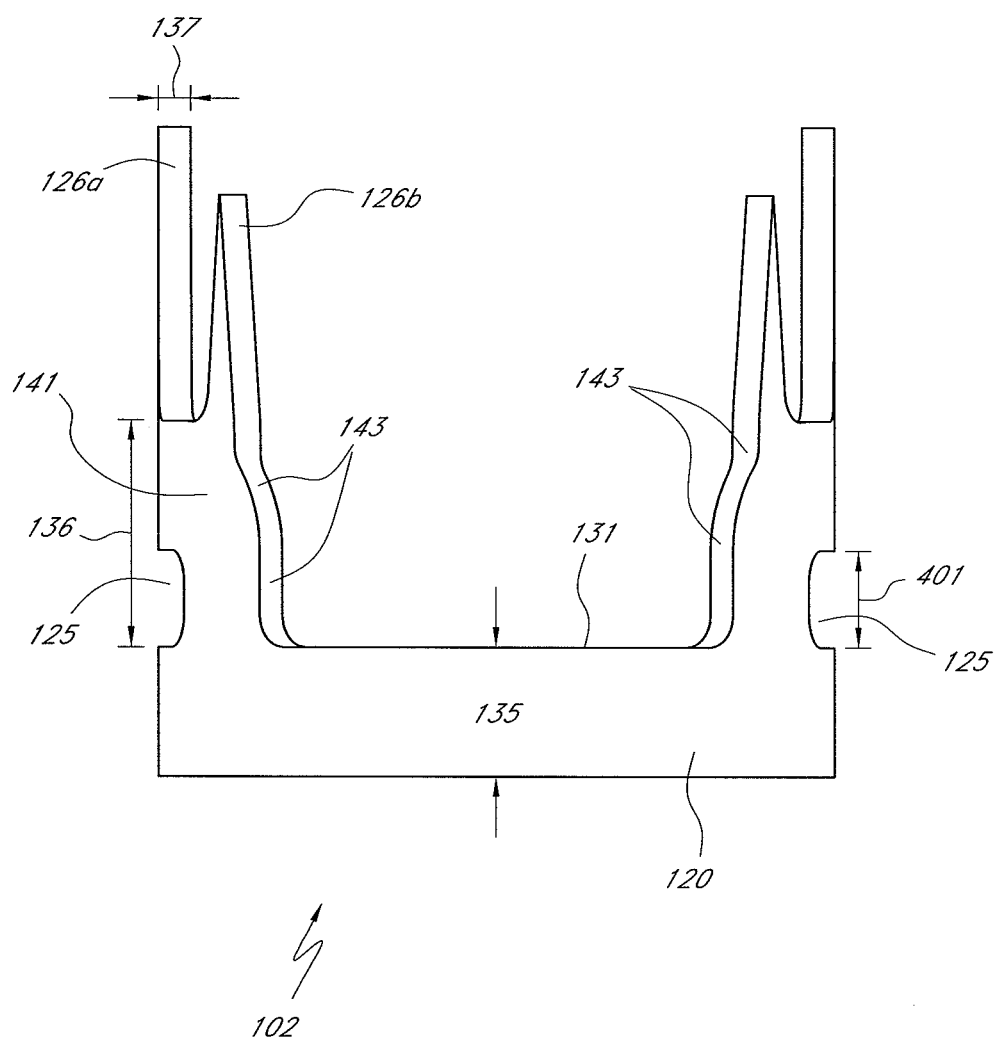
FIG. 4 is a side view of the clip of FIG. 2 in an open configuration.

FIG. 4 is a side view of clip 102 in an open configuration. The respective heights 135, 136, 401, of the base portion 120, the support portion 141, and the bend-facilitating region 125, can have many different values, depending on the particular application of the clip 102 and other design preferences. Moreover, these heights 135, 136, 401 can be constant or can vary in some embodiments. By way of example, the height 135 of the base portion 120 may be greater than or equal to about 0.5 mm and/or may be less than or equal to about 2 mm; the height 136 of the support portion 141 may be greater than or equal to about 0.5 mm and/or may be less than or equal to about 4 mm; and the height 401 of the bend-facilitating region 125 may be greater than or equal to about 0.2 mm and/or may be less than or equal to about 2 mm. In some embodiments, the height 135 is about 1 mm, the height 136 is about 2 mm, and the height 401 is about 0.8 mm.

As illustrated, the height 136 of the support portions 141 of fingers 122 and 124 can be less than the length 133 of central tines 126*a* (for example, less than about 80%). This may permit the base portion 120 of the clip 102 to be positioned relatively close to the outer surface of the vessel wall 116 when the clip 102 is attached. In some embodiments, the support portions 141 can have different sizes or may be eliminated (e.g., with the tines 126*a,b* attaching directly to the base portion 120). In other embodiments, height 136 can be approximately equal to or greater than the length 133 of central tines 126*a*. The support portions 141 can include smoothly contoured sides 143, as illustrated, to diminish the likelihood that the support portions 141 will pierce the vessel wall 116 and/or cause trauma to the vessel wall 116. In the illustrated embodiment, the outer surface of the support portions 141 is curved (e.g., similar in curvature to the outer surface of the base portion 120). In some embodiments, the outer surface of the support portions 141 can be flat or can be shaped in a way different from the outer surface of the base portion 120.

Figure 5:
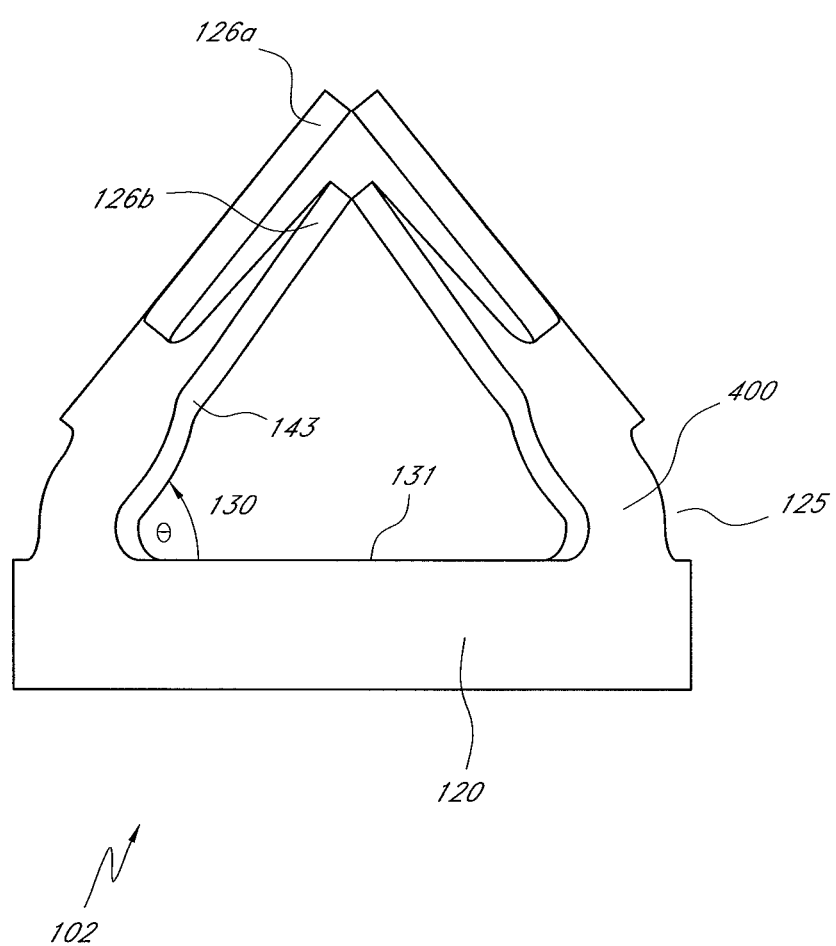
FIG. 5 is a side view of the clip of FIG. 2 in a closed configuration.

FIG. 5 is a side-view of clip 102 in a closed configuration. In a deployed state, clip 102 can define an angle θ 130 between a central axial line or an edge in fingers 122, 124 and a peripheral surface or an edge 131 of base 120. Angle θ 130 can be selected to assist in determining the applied closure force and to facilitate removal of clip 102 in embodiments utilizing temporary closure, as explained further below. Angle θ 130 also can be selected to assist in determining the overall depth of penetration by the tines 126*a*, 127*b* into the vessel wall 116. For example, a smaller angle will generally produce a more shallow penetration and a larger angle will generally produce a deeper penetration. In some embodiments, Angle θ 130 can be greater than or equal to about 30° and/or less than or equal to about 70°. In a particular example, Angle θ 130 can be about 50°. Other appropriate angles can also be used. In some embodiments, as illustrated, the flexion regions 400 can bend while other structures remain substantially unchanging or intact.

Figure 6:
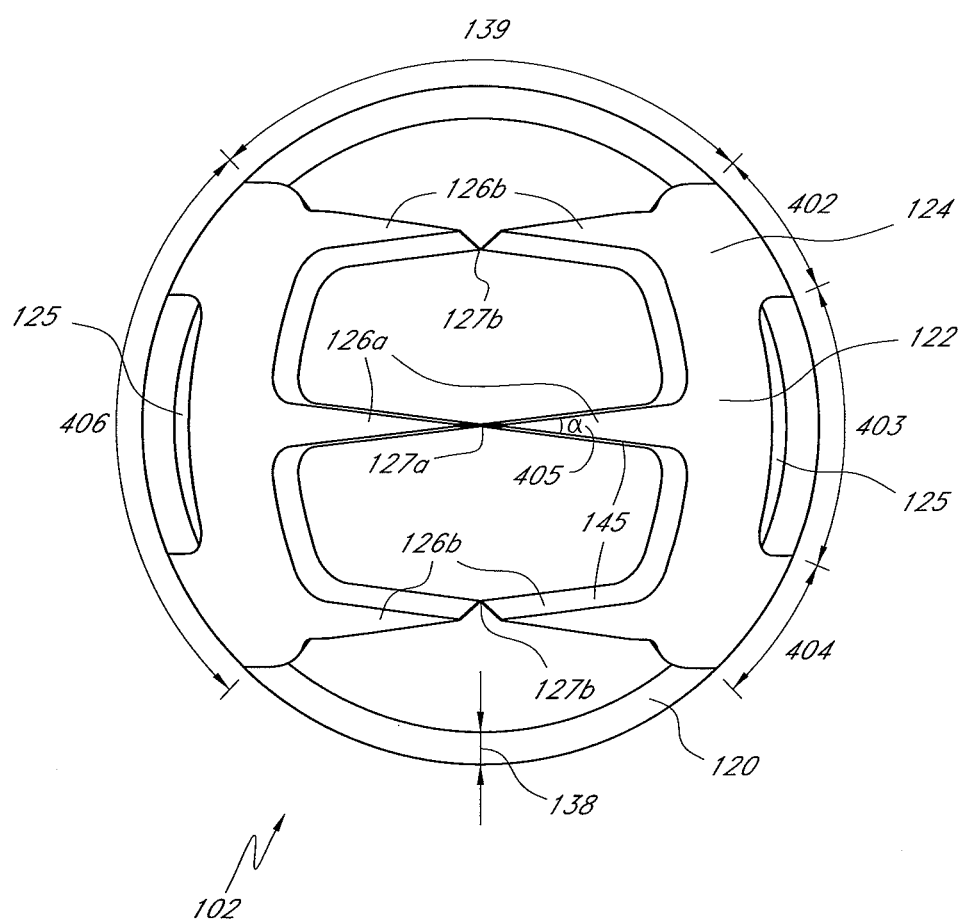
FIG. 6 is a bottom view of the clip of FIG. 2 in a closed configuration.

FIG. 6 is a bottom view of clip 102 in a closed configuration. As illustrated, opposed pairs of tines 126*a*, 126*b* can be configured to contact one another or to draw very close to each other (e.g., within a distance equivalent to about the thickness 137 of each tine 126a, 126b) in the closed configuration. In other embodiments, the tines 126a, 126 need not be configured to move very close to each other in the closed configuration. In some embodiments, base portion 120 has a side thickness 138 which can be greater than or equal to about 0.1 mm and/or less than or equal to about 0.5 mm, such as about 0.2 mm. As illustrated, in some embodiments, all portions of the clip 102 can share approximately the same thickness. The thickness can also vary between different portions of the clip 102 in appropriate circumstances. For example, referring to FIG. 4, tines 126a-b can have a thickness 137 which can be less than thickness 138 of the base portion 120 to facilitate penetration of the vessel wall 116.

Base portion 120 can define an outer diameter and an inner diameter. For example, the outer diameter can be greater than or equal to about 3 mm and/or less than or equal to about 7 mm, and the inner diameter can be greater than or equal to about 2.5 mm and/or less than or equal to about 6.5 mm. In some embodiments, the outer diameter is about 5.3 mm and the inner diameter is about 4.8 mm. Different size clips can be utilized depending on the specific tissue compression or closure application for which they are being used and to account for different anatomical sizes, such as differences in the thickness or diameter of the vessel wall 116. In some instances, a plurality of different-sized clips 102 can be provided to health care professionals to allow for variability and increased precision in diminishing trauma and increasing the appropriate closure force for a particular patient. Moreover, a clip size also can be selected to accommodate the tubular medical device over which the clip will be advanced. In embodiments effecting arteriotomy closure, the clip's inner diameter should be large enough to be advanced over a standard commercial introducer.

As illustrated in FIG. 6, the tines can have straight edges 145 and define an inner angle α 405. Angle α 405 can be selected to help adjust an insertion force required to cause penetration of the tines 126a, 126b into or withdrawal of the tines 126a, 126b from the vessel wall 116. In some embodiments, angle α 405 can be greater than or equal to about 3° and/or less than or equal to about 15°, such as 9°. The widths of the tips 127a, 127b of tines 126a, 126b can also be adjusted to determine a required insertion force. In certain embodiments, the width of tips 127a, 127b can be greater than or equal to about 0.03 mm, and/or less than or equal to about 0.09 mm, such as 0.06 mm. In certain embodiments, the edges of the tines 126a, 126b can be curved, segmented, or define different angles at different portions. In certain embodiments, the tines 126a, 126b can include barbs, protrusions, or other elements configured to resist withdrawal from the vessel wall 116. The barbs can be sized or configured to provide sufficient resistive force to prevent accidental removal of the clip 102 during partial deployment of the clip 102 as explained in more detail below. In certain embodiments, the resistive force provided by the barbs can also be sufficiently small to permit atraumatic removal of the clip 102.

For embodiments in which the base 120 is substantially circular, arc 406 corresponds to the circumferential width of fingers 122 and 124. In the illustrated embodiment, arc 406 subtends an approximately 90° angle. In some embodiments, arc 406 can subtend an angle greater than or equal to about 60° and/or less than or equal to about 90°. Other angles can also be used. Arc 403 corresponds to a circumferential width of window portions 125. In some embodiments, arc 403 can subtend an angle between greater than or equal to about 15° and less than or equal to about 30°. In certain embodiments, arc 403 can be less than or equal to about one-half the length of arc 406. Connecting portions of fingers 122 and 124 adjacent to the window portions 125 can have widths defined by arcs 402 and 404. Arc 139 corresponds to the separation distance between fingers 122 and 124. In the illustrated embodiment, arc 139 subtends an angle of approximately 90°. In some embodiments, arc 139 can subtend an angle greater than or equal to about 60° and/or less than or equal to about 90°. Other angles can also be used. In some embodiments, as illustrated, the shape and/or orientation of the base portion are substantially or entirely unchanged in the transition between an open or pre-deployed state and a closed or deployed state.

Figure 7:
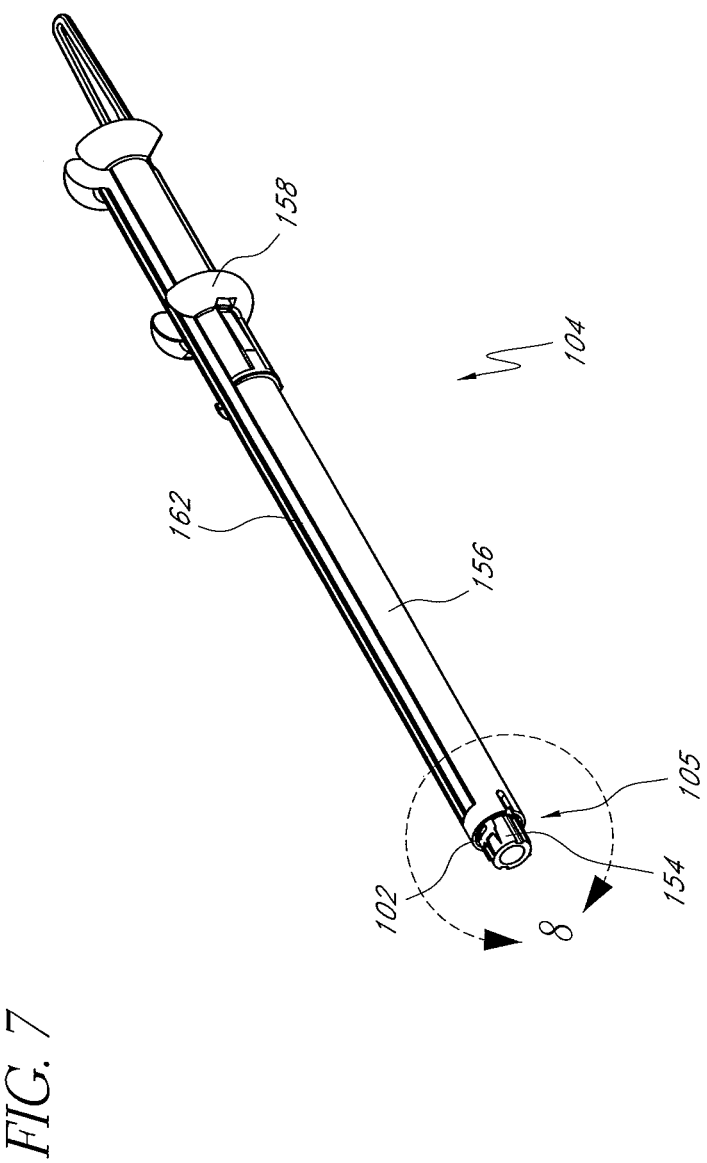
FIG. 7 is a perspective view of a deployment instrument preloaded with a vascular closure clip.

FIG. 7 is a perspective view of deployment instrument 104 with clip 102 in the open or pre-deployed position attached to a distal end thereof. The configuration illustrated in FIG. 7 is generally an initial or starting configuration before insertion of the deployment instrument 104 into a patient. The deployment instrument 104 with a pre-loaded clip 102 can be provided to the physician in a sterilized package in this general configuration. In certain embodiments, the deployment instrument 104 can be constructed with three basic components: inner tube 154, outer tube 156, and pressure element 158.

Figure 8:
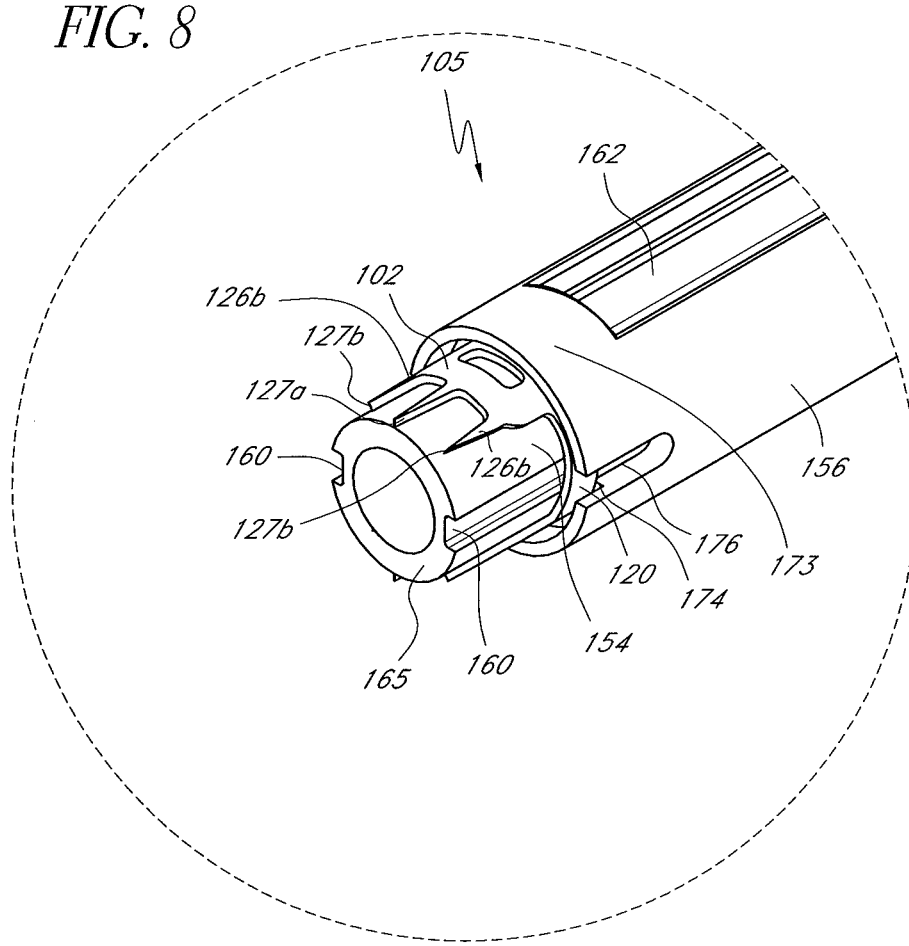
FIG. 8 is a close-up view of the distal end of the deployment instrument of FIG. 7.

FIG. 8 provides a more detailed view of the distal end 105 of the deployment instrument 104, which is configured to receive clip 102 and generally maintain it in an open configuration until deployed. In the illustrated embodiment, the tines 126a, 126b are substantially parallel with a central axis of the inner tube 154, and the distal ends 127a, 127b of the tines 126a, 126b are substantially aligned with the distal end 165 of the inner tube 154. In other embodiments, the distal ends 127a, 127b of the tines 126a, 126b can extend slightly beyond the distal end 165 of the inner tube 154. Alternatively, clip 102 can be located more proximally while the deployment instrument 104 is in its initial configuration with the distal ends 127a, 127b of the tines 126a, 126b being proximally spaced from the distal end 165 of the inner tube 154. As will be described in more detail below, the inner diameter of the base 120 of the clip 102 can be positioned close to or in contact with the outer diameter of the distal end 165 of the inner tube 154, and the outer diameter of the base 120 of the clip 102 can be positioned close to or in contact with the inner diameter of the distal end 173 of the outer tube 156. A radially inwardly directed restoring force exerted by the tines 126a, 126b in the open configuration increases the friction between the inner surfaces of the clip 102 and the outer surface of the inner tube 154, generally preventing the clip 102 from readily sliding away from its position between the inner and outer tubes 154, 156.

Distal end 173 of outer tube 156 can include an interior ledge or countersink 174 configured to receive and abut against the base 120 of clip 102. As will be explained in more detail below, when the assembled deployment instrument 104 is advanced to the tissue closure site and the inner tube 154 is axially withdrawn in the proximal direction from the outer tube 156, a distally directed reaction force is exerted by countersink 174 against the base 120 of the clip 102, preventing the clip 102 from also moving in the proximal direction. When the distal end 165 of the inner tube 154 is moved in the proximal direction past the base 120 of the clip 102, the contacting or adjacent relationship between the clip 102 and the inner and outer tubes 154, 156 is interrupted and the clip 102 is released from the deployment instrument 104. In certain embodiments, the use of countersink 174 can permit the outer tube 156 to avoid contact with or otherwise to protect all or a portion of clip 102 during advancement prior to deployment. In other embodiments, countersink 174 can be omitted and the distal-most surface of outer tube 156 can be configured to contact base 120 to force off or otherwise permit removal of the clip 102 from the deployment instrument 104.

Figure 9:
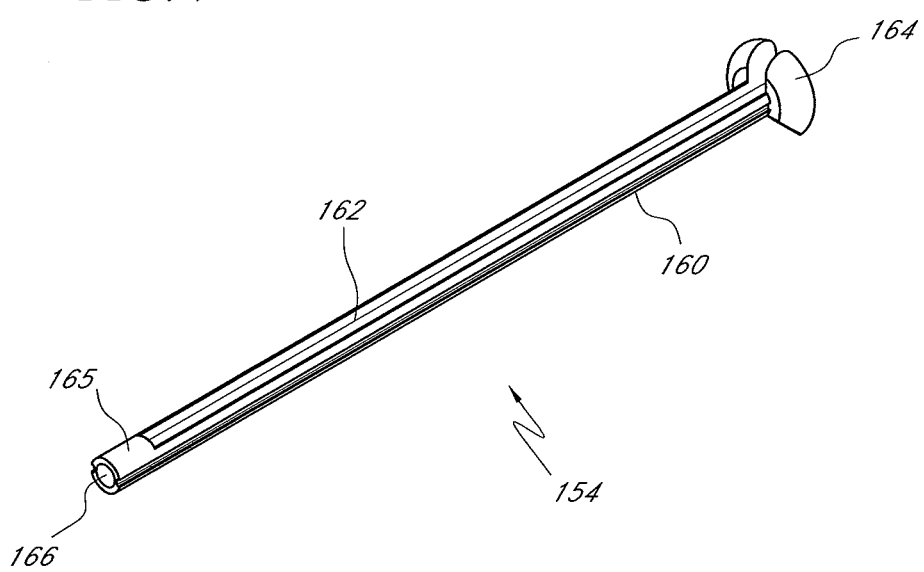
FIG. 9 is a perspective view of an inner tube portion of the deployment instrument of FIG. 7.
Figure 10:
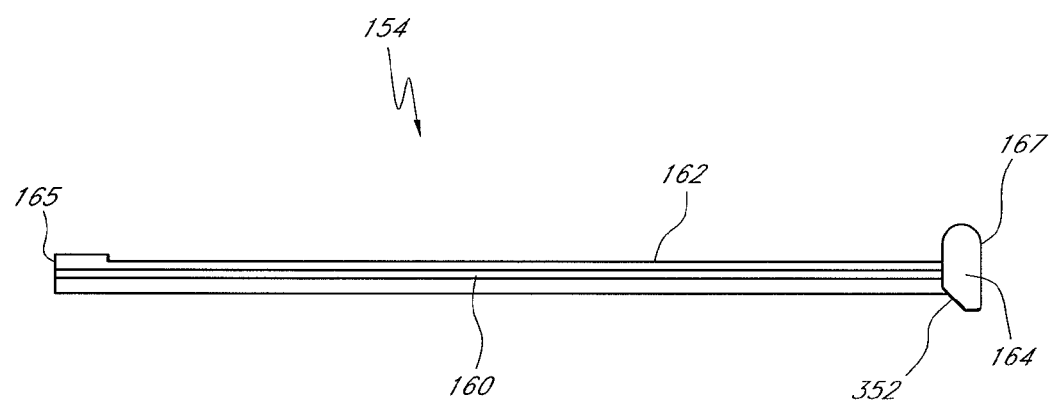
FIG. 10 is a side view of the inner tube of FIG. 9.
Figure 11:
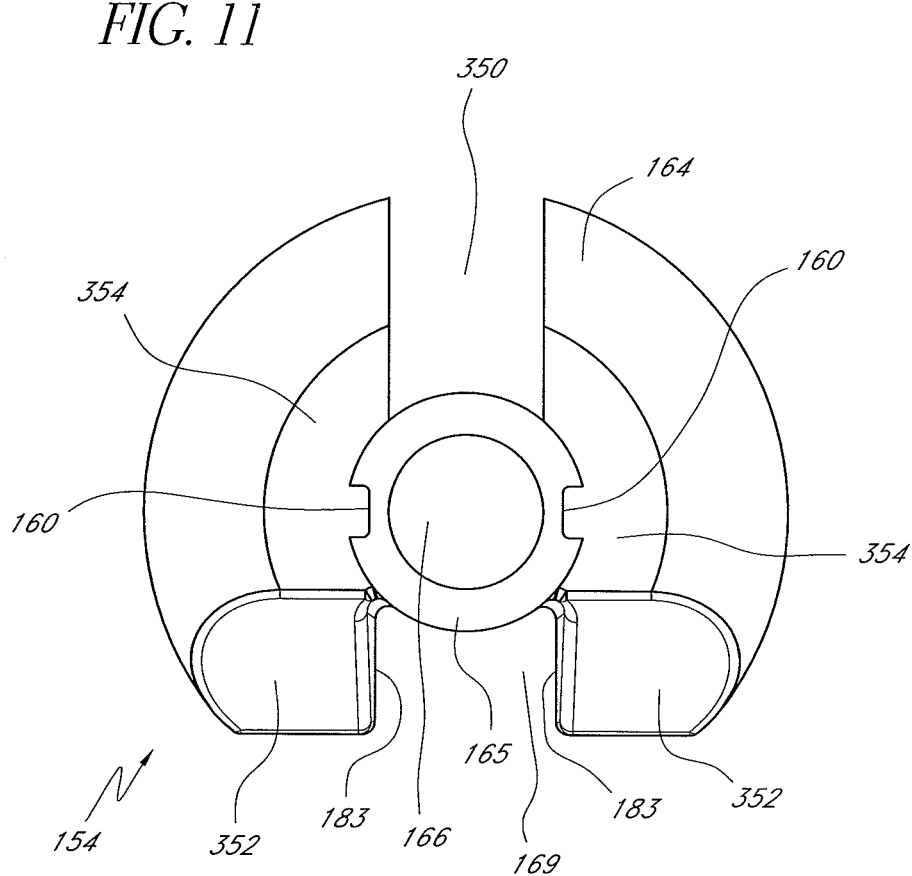
FIG. 11 is a distal end view of the inner tube of FIG. 9.
Figure 12:
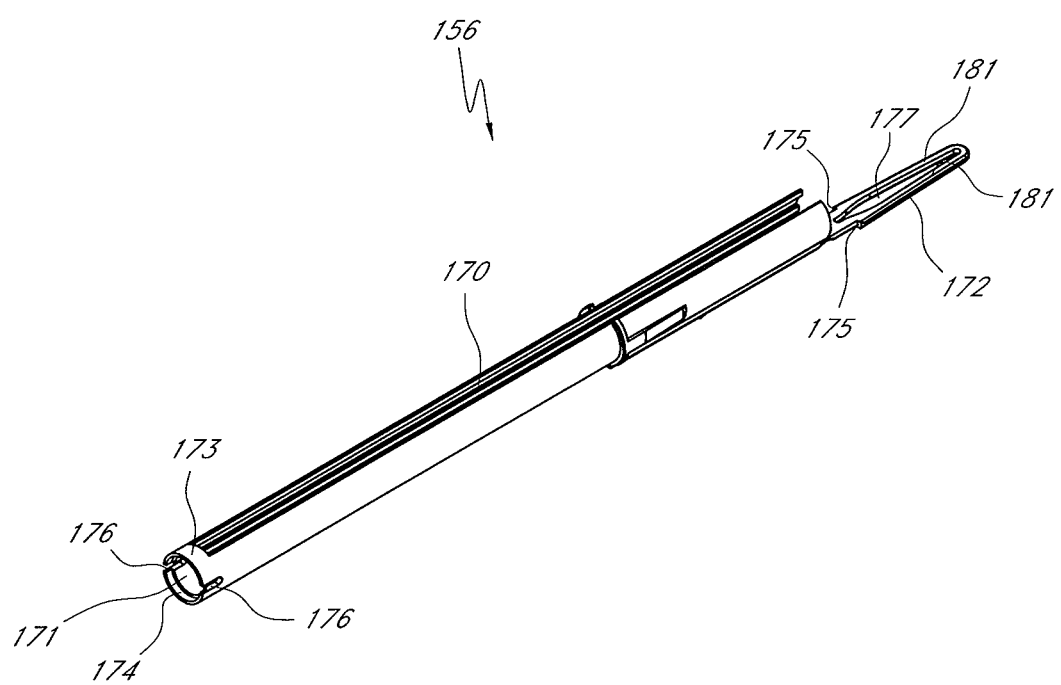
FIG. 12 is a perspective view of an outer tube portion of the deployment instrument of FIG. 7.
Figure 13:
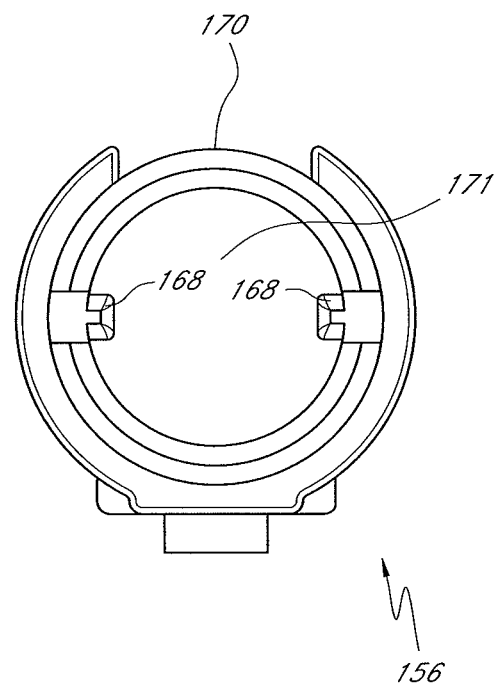
FIG. 13 is a distal end view of the outer tube of FIG. 12.
Figure 14:
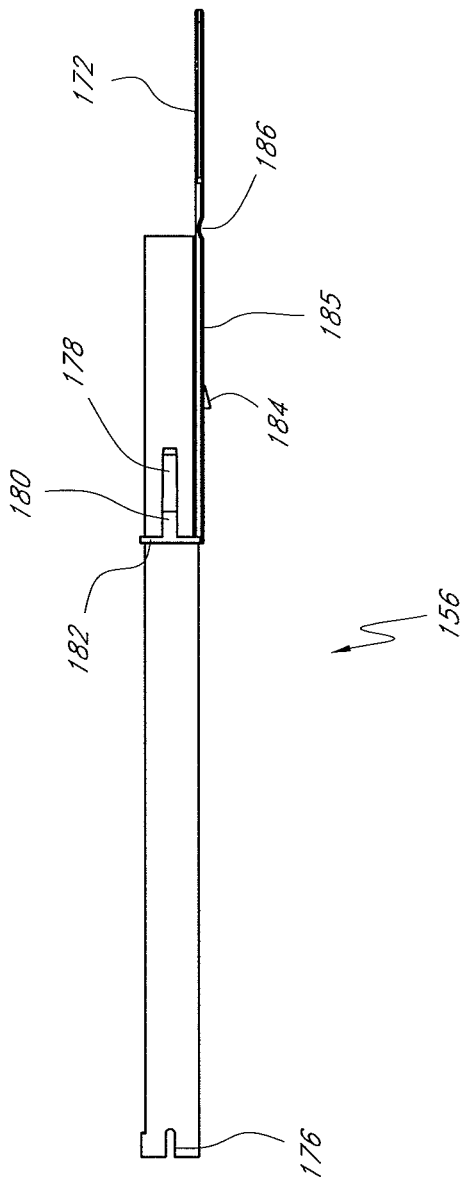
FIG. 14 is a side view of the outer tube of FIG. 12.
Figure 15:
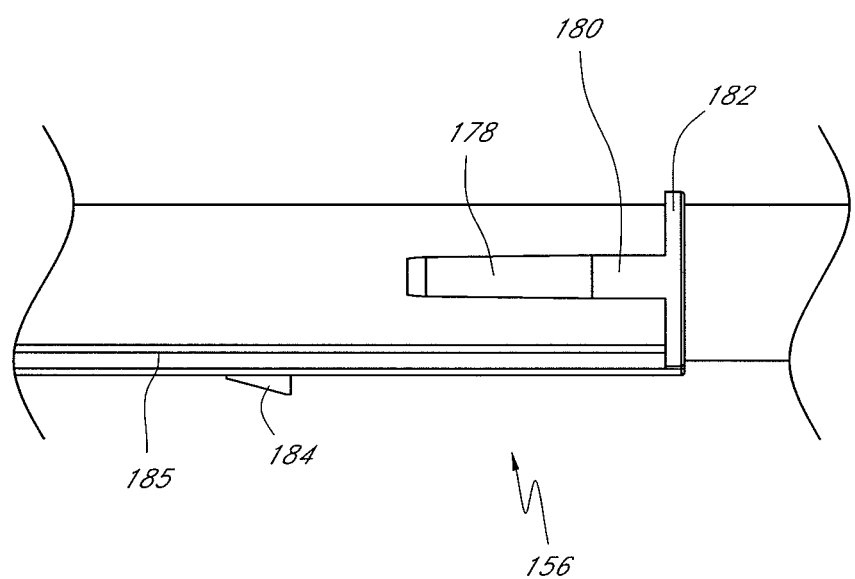
FIG. 15 is a close-up side view of an intermediate portion of the outer tube of FIG. 12.
Figure 16:
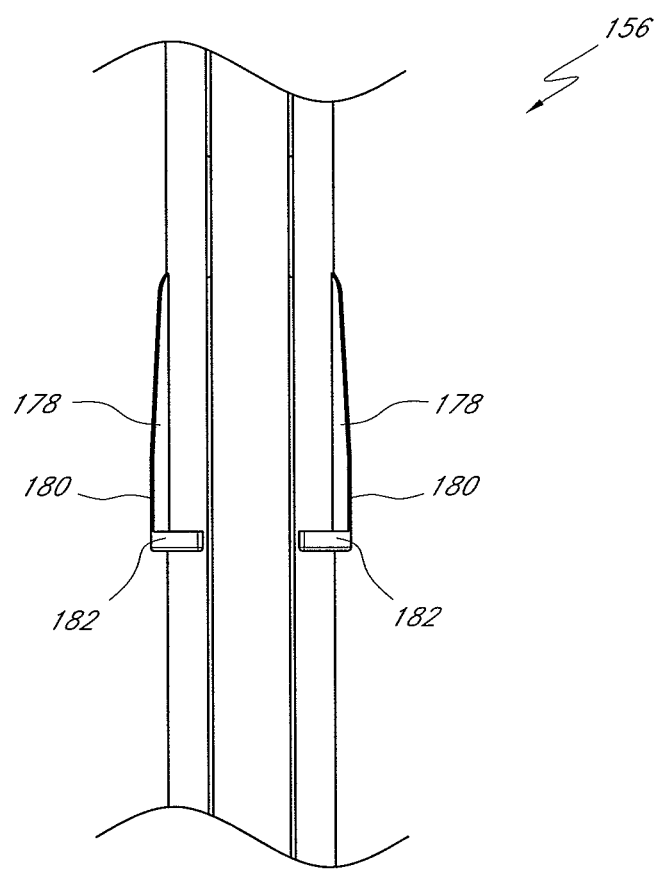
FIG. 16 is another close-up side view of an intermediate portion of the outer tube of FIG. 12.

FIGS. 9-11 are illustrations of an example of the inner tube 154 separated from the outer tube 156 before the configuration illustrated in FIGS. 7-8 is assembled. Inner tube 154 defines an inner lumen 166 which is configured to receive a tubular medical device such as a vascular introducer 108. Elongate slot 162 allows at least a portion of the deployment instrument 104 to be tilted away from and axially separated from the proximal portion of the vascular introducer 108 by a medical professional without detaching the instrument 104 entirely from the tube section 110. (See, e.g., FIG. 1.) This configuration permits the medical professional to position the deployment instrument 104 out of the way while the desired interventional or diagnostic procedure is performed. In the illustrated embodiment, axial grooves 160 run along the length of the outer surface of inner tube 154 and are configured to mate with axial protrusions 168 (see FIG. 13) formed on an inner surface of outer tube 156. This mating configuration can prevent inner tube 154 from rotating relative to outer tube 156 and can help to align elongate slot 162 of inner tube 154 and elongate slot 170 of outer tube 156.

The proximal end of inner tube 154 includes a handle 164 which may be gripped by the medical professional to withdraw inner tube 154 during deployment. As illustrated, handle 164 can be generally circular with a flattened lower end to facilitate delatching of the stop mechanism during complete deployment as explained below. Other shapes and configurations can also be used. The upper portion of handle 164 includes a cut-out portion 350 which is aligned with and merges with elongate slot 162. Lower portion of handle 164 includes a recess 169 to accommodate tab 172 of the outer tube 156. The distal end of handle 164 includes distal faces 354 which can be substantially flat. Faces 354 are configured to abut the proximal-most edge of the tube section of outer tube 156 to prevent over-insertion of inner tube 154 into outer tube 156. Proximal faces 167 of handle 164 can be substantially flat and are configured to abut stops 175 on tab 172 during partial deployment. Lower portion of the handle 164 can include angled surfaces 352.

FIGS. 12-16 are illustrations of an example of an outer tube 156 separated from the inner tube 154 before the configuration illustrated in FIGS. 7-8 is assembled. Outer tube 156 defines an inner lumen 171 configured to receive inner tube 154. An elongate slot 170 runs along a length of outer tube 156 and provides access to the interior of inner lumen 171. Elongate slot 170 of outer tube 156 is configured to align with elongate slot 162 of inner tube 154. Distal end 173 of outer tube 156 can include one or more slots 176 to provide side access to clip 102 while deployment instrument 104 is in its initial configuration.

A securing or movement-limiting structure such as tab 172 extends from a proximal end of outer tube 156. Tab 172 includes stop surfaces 175 configured to abut the proximal faces 167 on handle 164 during partial deployment as explained in more detail below. Tab 172 can include two tapered arms 181 surrounding a window portion 177 to facilitate assembly of the deployment instrument 104 as explained further below. Tab 172 can also include a recessed, weakened, or hinge portion 186 to facilitate bending. In certain embodiments, tab 172 can be relatively rigid with the exception of weakened portion 186. In certain embodiments, bending of tab 172 can be configured to occur substantially at weakened portion 186. In certain embodiments, tab 172 can be relatively long. For example, tab 172 can be at least about 20 mm. A long tab 172 can facilitate handling by the medical professional. A long tab 172 can also increase the leverage applied by the medical professional to effectuate bending.

The deployment instrument can include a pressure sensitive structure which can comprise, in one example, pressure tapers 178 formed on an outer surface of outer tube 56 and flexible tabs 188 of pressure element 158. Outer tube 156 can also include a pressure sensitive structure such as an axial protrusion 185 extending from a proximally-located outer surface. As illustrated, axial protrusion 185 can be located in a substantially diametrically opposite position from elongate slot 170, although other configurations are possible. A ramp or one-way tapered lock 184 extends from axial protrusion 185. A stop, 182 which can be generally annular in shape, extends from an outer surface of outer tube 156. The outer surface of outer tube 156 also includes pressure tapers 178. Pressure tapers 178 can terminate in substantially flat surfaces 180. Surfaces 180 can be adjacent to and in contact with annular stop 182. As illustrated, outer tube 156 can include two pressure tapers 178 located in a substantially diametrically opposite position from one another on the generally circular outer tube 156. Also as illustrated, pressure tapers 178 can be positioned at approximately equal circumferential distances from elongate slot 170 and axial protrusion 185. Other configurations are possible.

Figure 17:
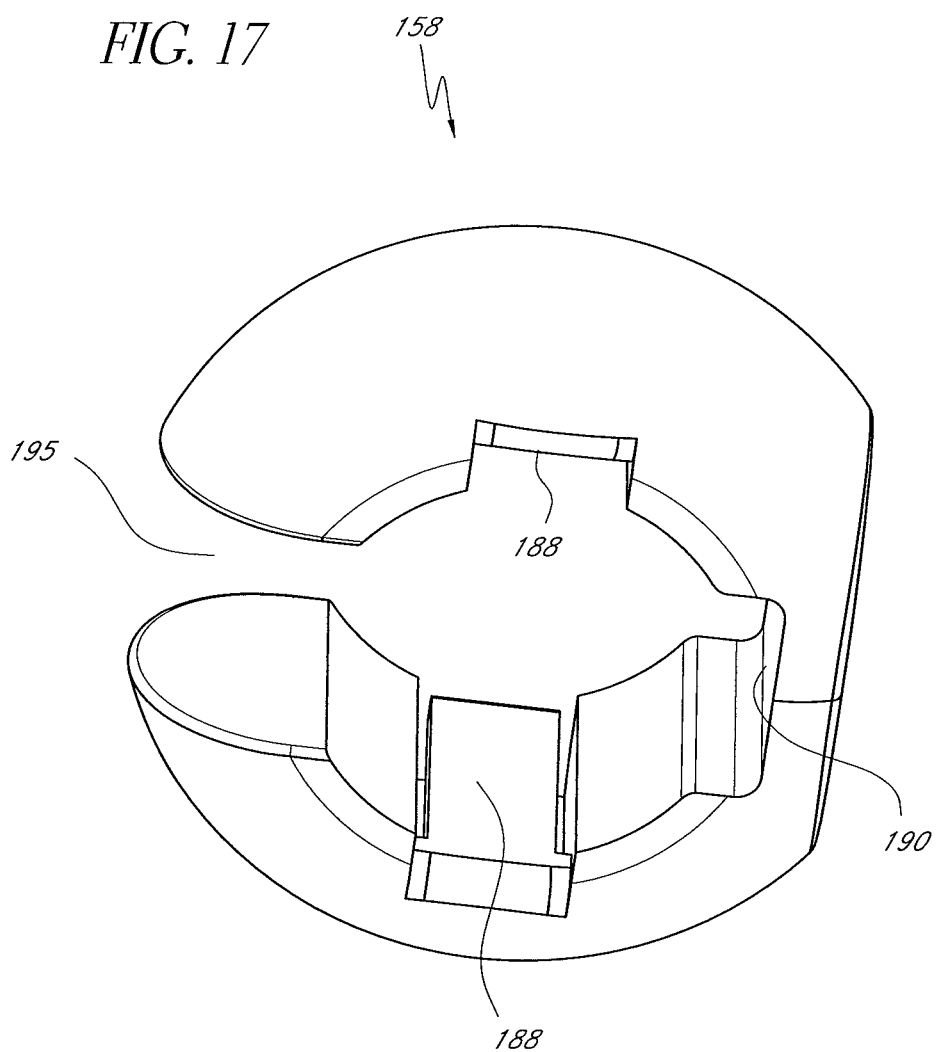
FIG. 17 is a perspective view of a pressure element of the deployment instrument of FIG. 7.

FIG. 17 provides a detailed illustration of a pressure element 158, which in some embodiments can be a generally ring-shaped element configured to be received on an outer surface of outer tube 156. In certain embodiments, as illustrated, pressure element 158 can be a separate element from outer tube 156. In other embodiments, pressure element 158 can be integrally formed with outer tube 156. As described in more detail below, pressure element 158 can be utilized to confirm that the medical professional is applying generally sufficient but not excessive pressure to safely begin deployment of the clip 102. Pressure element 158 can include a cut-out portion 105 aligned with elongate slots 162, 170 of the inner and outer tubes 156, 154. Recess 190 can be configured to mate with axial protrusion 185 of outer tube 156 to keep the pressure element 158 properly aligned. An inner surface of pressure element 158 includes one or more flexible tabs 188. Flexible tabs 188 are configured to align with, and be advanced over, pressure tapers 178 of outer tube 156.

During assembly of deployment instrument 104, pressure element 158 can be advanced over the proximal end of outer tube 156 and over one-way tapered lock 184. Recessed portion 190 and/or lock 184 can be configured to flex or temporarily deform sufficiently to accommodate this procedure. Alternatively, lock 184 or other locking means can be formed on, or secured to, outer tube 156 after positioning of pressure element 158. Tapered lock 184 prevents pressure element 158 from moving too far in a proximal direction with respect to outer tube 156. Inner tube 154 can then be inserted into the inner lumen 171 of outer tube 156 from the outer tube's proximal end. As the inner tube 154 is inserted into outer tube 156, inner surfaces 183 (see FIG. 11) of the lower portion of handle 164 adjacent to recess 169 begin to come into contact with tapered arms 181 of tab 172. The continued advancement of inner tube 154 distally causes surfaces 183 to apply an inwardly-directed force to arms 181. Window 177 permits arms 181 to resiliently flex inwardly until handle 164 has been advanced distally of stops 175. Inner tube 154 can then be advanced further until distal faces of handle 354 contact the proximal-most edge of the tube section of outer tube 156.

Figure 18:
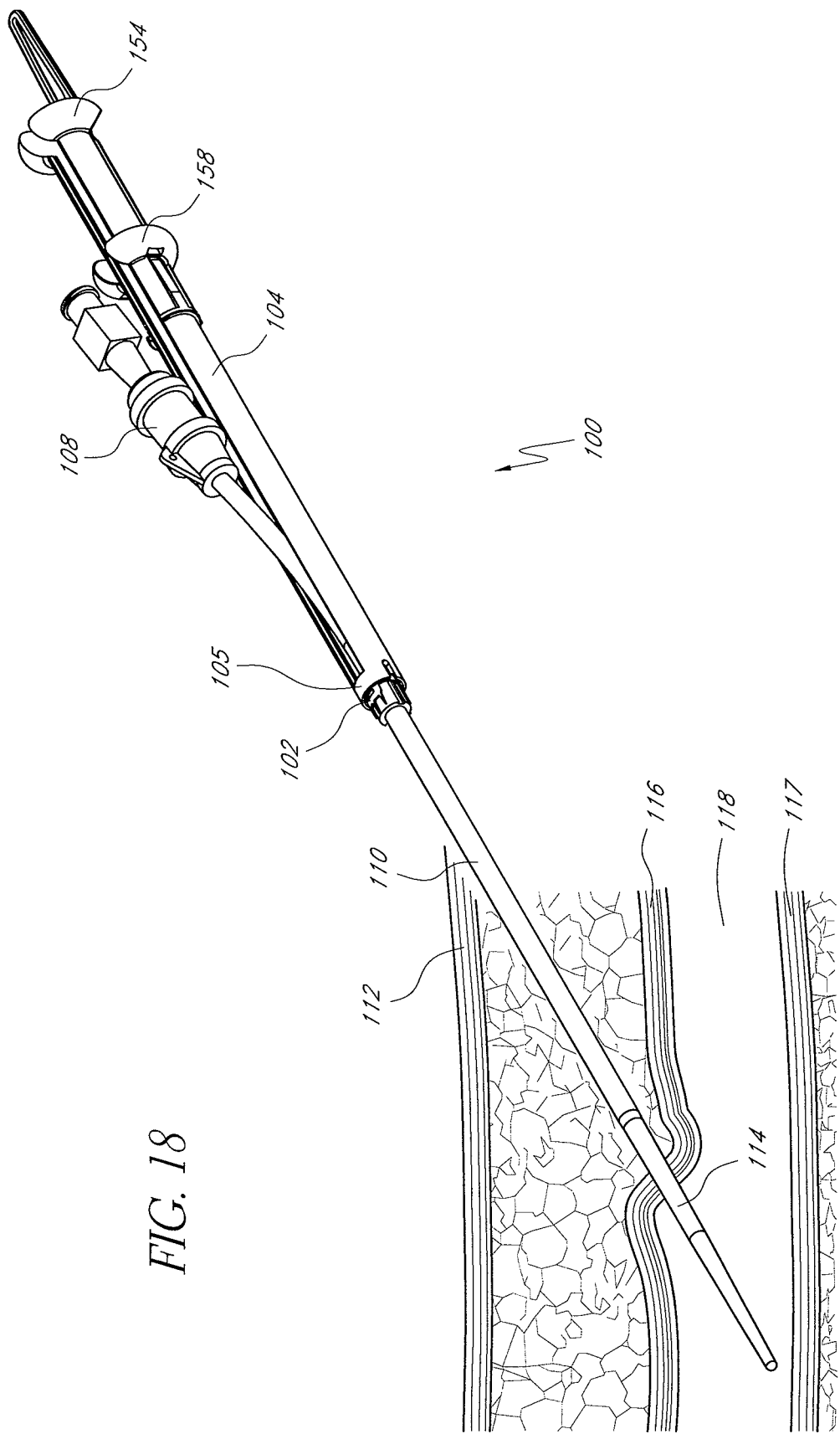
FIG. 18 is a perspective view of the deployment instrument of FIG. 7 loaded onto a vascular introducer that has been inserted into a patient's blood vessel.

An example of a method for using deployment instrument 104 and clip 102 will now be described. FIG. 18 illustrates a deployment instrument 104 in an initial configuration loaded onto a vascular introducer 108 that has been inserted into a patient's blood vessel 118. The deployment instrument 104 can also be configured for use with other medical devices such as, for example, tubular or elongate dilators, trocars, endoscopes, catheters, guide wires, needles, tubes, sheaths, combination or other. The tubular medical device 108 is first inserted through the inner diameter of the deployment instrument 104 which has been loaded with clip 102. The tubular medical device 108 can then be inserted through the skin and into the desired vessel 118 using any of a number of known methods, such as, for example, the Seldinger method. The desired interventional or diagnostic procedure is then performed. The deployment instrument 104 can be temporarily moved to the side as illustrated so as not to interfere with the medical procedure. For example, the deployment instrument 104 can be moved toward the back or proximal end of the introducer sheath 108 as shown in FIG. 18. Slots 162 and 170 (see FIGS. 7 and 12) facilitate this positioning.

Figure 19:
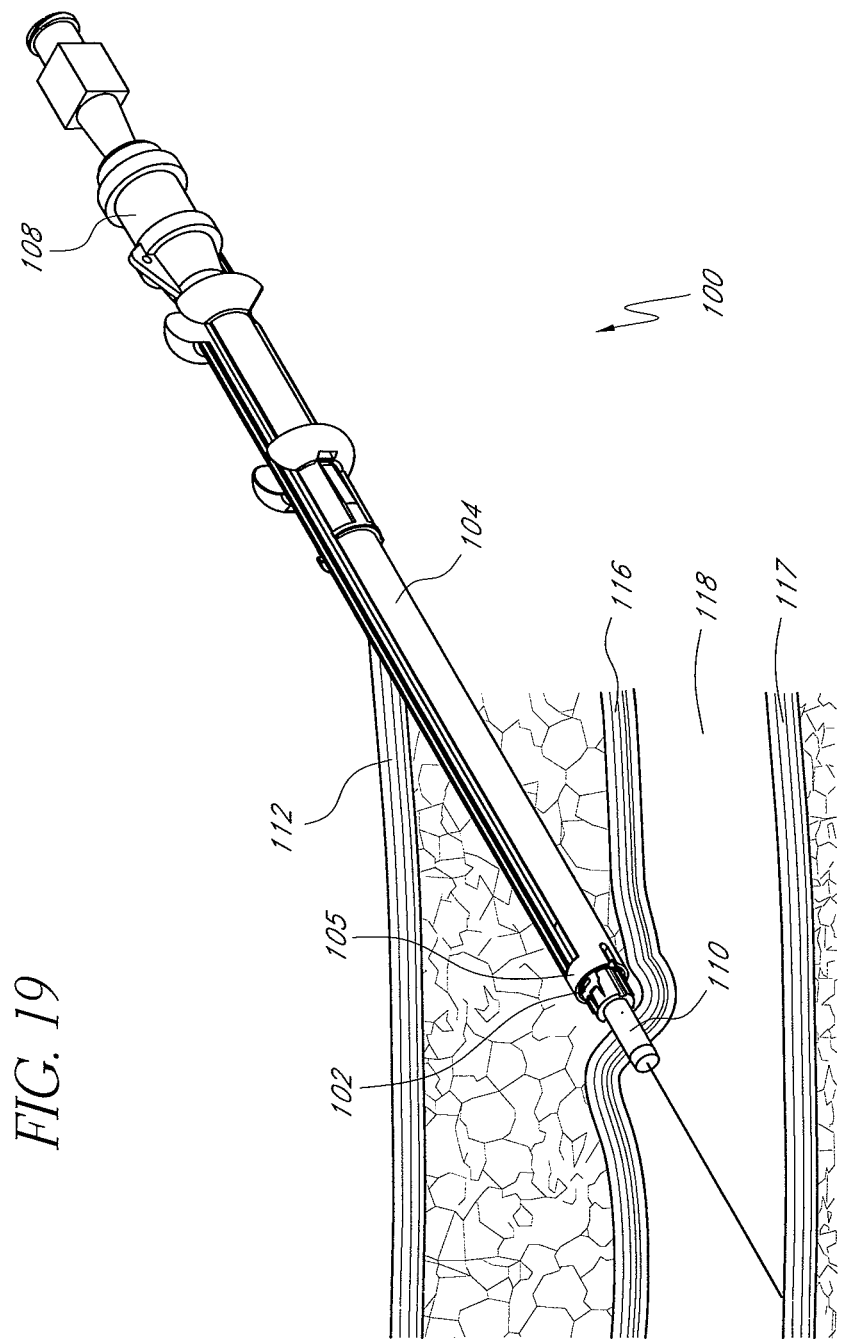
FIG. 19 is a perspective view of the deployment instrument of FIG. 7 which has been advanced over the vascular introducer until its distal end encounters the vessel wall.
Figure 20:
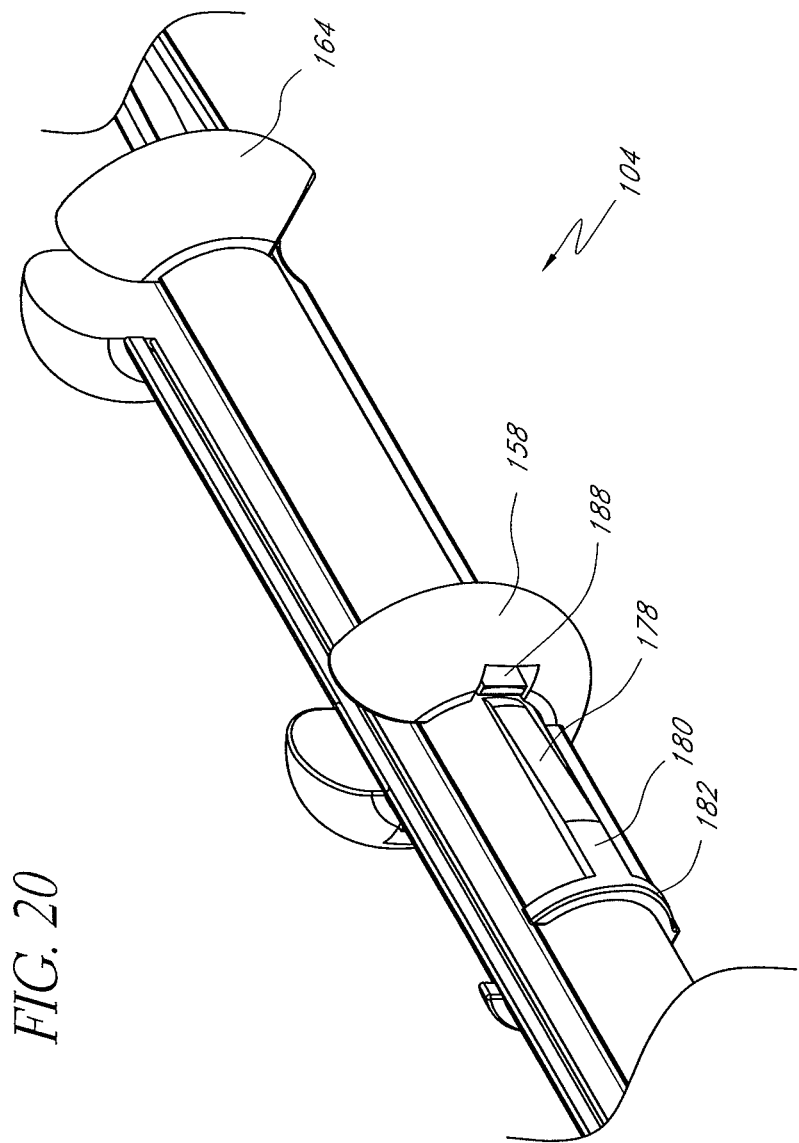
FIG. 20 is a close-up view of the deployment instrument of FIG. 19 showing the pressure element in an initial, relaxed position.

With reference to FIGS. 19-20, deployment instrument 104 is advanced forward along the introducer sheath through the percutaneous opening 112 until the distal end 105 of the deployment instrument 104 contacts the vessel wall 116. At this state along the pressure sensitive structure on the outside of outer tube 156, pressure element 158 is in its initial, non-advanced configuration as shown in FIG. 20. In certain embodiments, a dilator that was previously removed or a new dilator or other elongate member can be inserted into the inner lumen of the vascular introducer 108 to provide mechanical support and resistance to kinking of the introducer 108. Reinsertion of the dilator may thus facilitate the advancement of deployment instrument 104 over the introducer 108.

Figure 21:
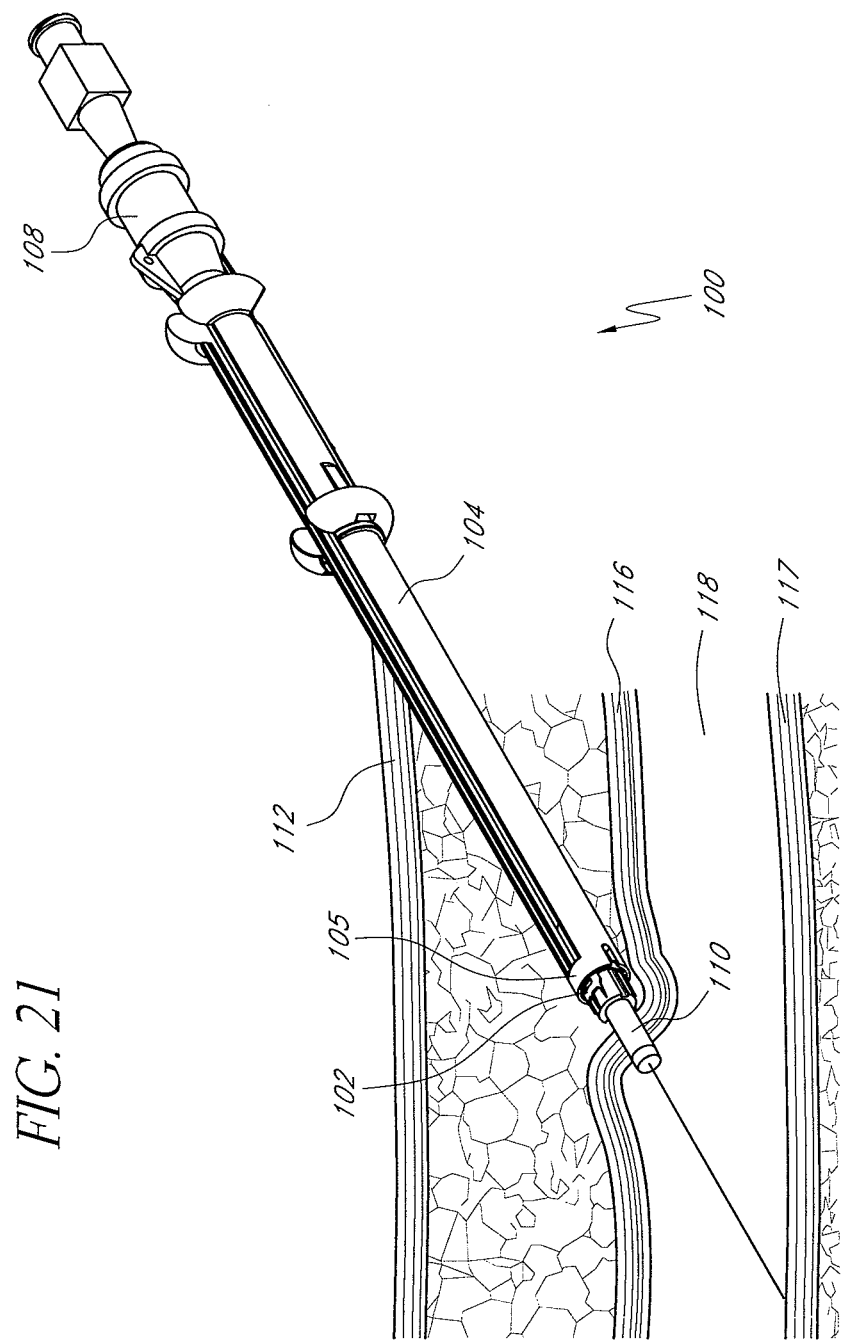
FIG. 21 is a perspective view of the deployment instrument of FIG. 7 with the pressure element fully advanced.
Figure 22:
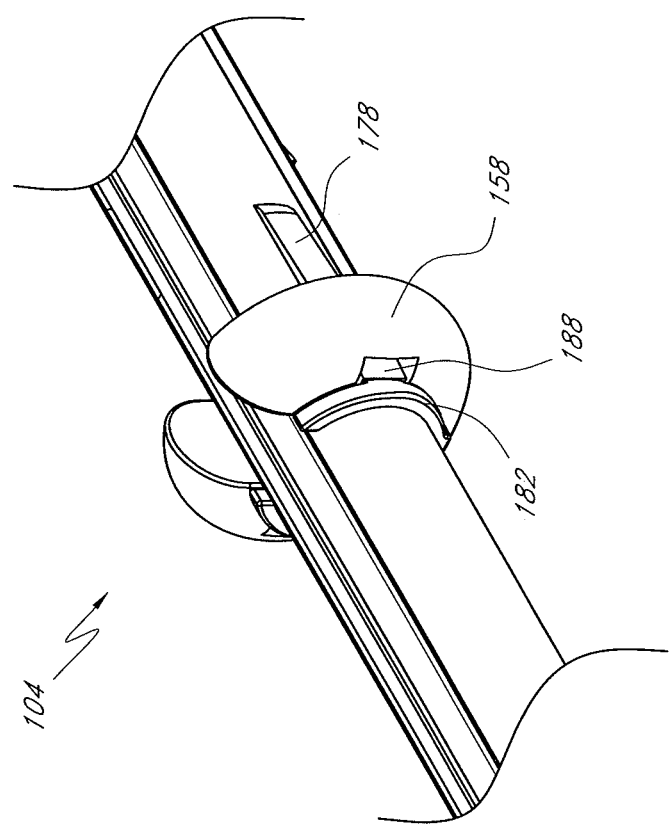
FIG. 22 is a close-up view of the deployment instrument of FIG. 21 showing the fully advanced pressure element.

With reference to FIGS. 21-22, pressure element 158 is then manually advanced distally until it reaches stop 182, indicating to the medical professional that appropriate force is being applied between the deployment instrument 104 and the vessel wall 116 to begin deployment. FIG. 22 is a close up view of the pressure element 158 in its fully advanced configuration. As the pressure element 158 is advanced distally, flexible tabs 188 are subjected to greater flexion as they advance up pressure tapers 178. Thus, advancing the pressure element 158 can require an increasing amount of applied force. Pressure tapers 178 generally flare outward until reaching flat surfaces 180. Stop 182 generally prevents pressure element 158 from advancing distally beyond this point. The amount of applied force required to fully advance the pressure element 158 can be adjusted by altering one or more of the number, size, width and rigidity of tabs 188, the angle of incline of pressure tapers 178 and the height of surfaces 180. In certain embodiments, the deployment instrument 104 can require at least about 10 ounces of force in order to safely begin deployment of the clip 102. Thus, in certain embodiments pressure element 158 can require at least about 10 ounces of force in order to be fully advanced. In certain embodiments, the deployment instrument can be configured to make an audible "click" or otherwise produce an audio, visual, or tactile signal when the pressure element 158 has been fully advanced.

In some embodiments, other pressure-sensitive structures such as a pressure or force gauge can be utilized to verify that adequate pressure is being applied. The deployment instrument can utilize a spring in place of, or in addition to, a taper element. A first end of the spring can be secured to a slidable element. A second end can be attached to a distal point on the outer tube. The slidable element can be used to compress the spring, thus applying force to the outer tube. A combination or other means to confirm sufficient contact and pressure between the deployment instrument and vessel can also be included. In certain embodiments, the deployment instrument can include a grasping tool configured to assist in securing the distal end of the deployment instrument to the vessel. In certain embodiments, the medical professional can observe a backflow of blood through a channel or window in the deployment instrument following removal of the tubular medical device to confirm proper placement on the vessel. Blood can be configured to flow through the central channel of the deployment instrument. In certain embodiments, a clear channel can be provided to receive blood flow. One or more sensors can be provided to verify proper placement and/or pressure.

Figure 23:
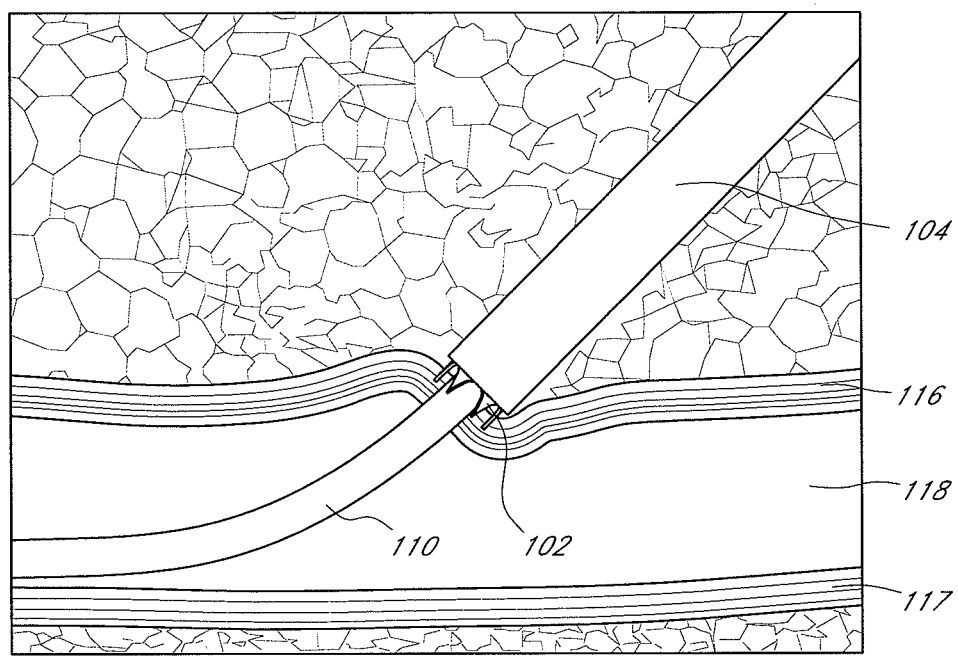
FIG. 23 is a close-up side view of the deployment instrument of FIG. 7 in a partially-deployed state showing the clip's tines penetrating the vessel wall.

FIG. 23 shows the deployment instrument 104 with clip 102 in a partially-deployed configuration. In a partially-deployed state, tines 126a, 126b can pierce the vessel wall 116 and the clip 102 remains attached to the deployment instrument 104 in a substantially open configuration. The medical professional partially deploys the clip 102 by beginning to withdraw inner tube 154. The medical professional can maintain adequate pressure on pressure element 158 (e.g. pressure sufficient to maintain pressure element 158 in its fully advanced configuration) while withdrawing inner tube 154. Handle 164 can be used to withdraw the inner tube 154. For example, the medical professional can apply distally-directed pressure to the pressure element 158 with one hand while partially withdrawing handle 164 with the remaining hand. The ledge or countersink 174 on outer tube 156 prevents clip 102 from being withdrawn along with the inner tube 154. Thus, as the inner tube 154 is withdrawn, the tines 126a,b begin to extend beyond the distal end 165 of inner tube 154. The continued application of pressure on pressure element 158 (and thus outer tube 156) generally forces the tines 126a,b to pierce the vessel wall 116. In certain embodiments, the pressure element 158 can include a means to prevent inner tube 154 from being withdrawn unless and until pressure element 158 is fully advanced.

Figure 24:
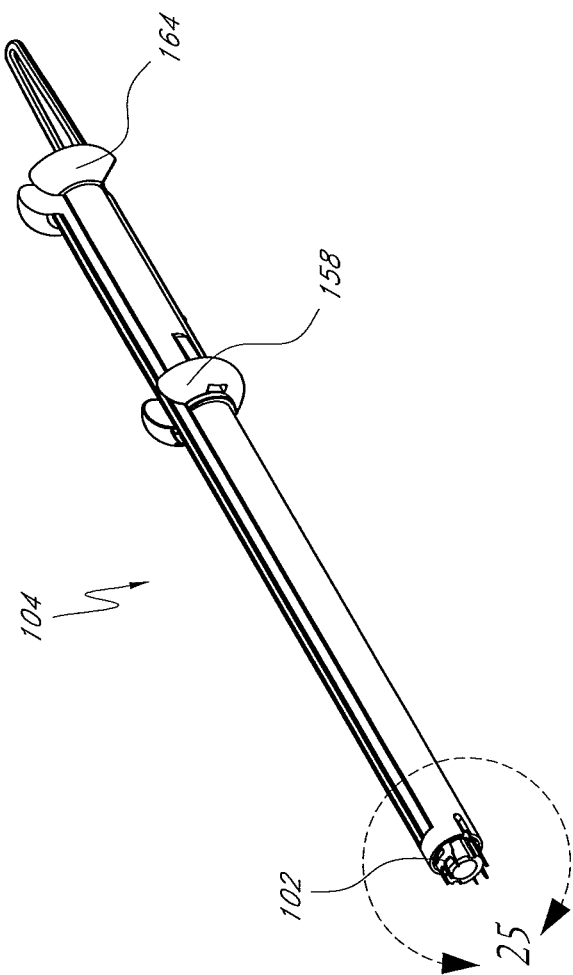
FIG. 24 is a perspective view of the deployment instrument of FIG. 7 in a partially-deployed state.
Figure 25:
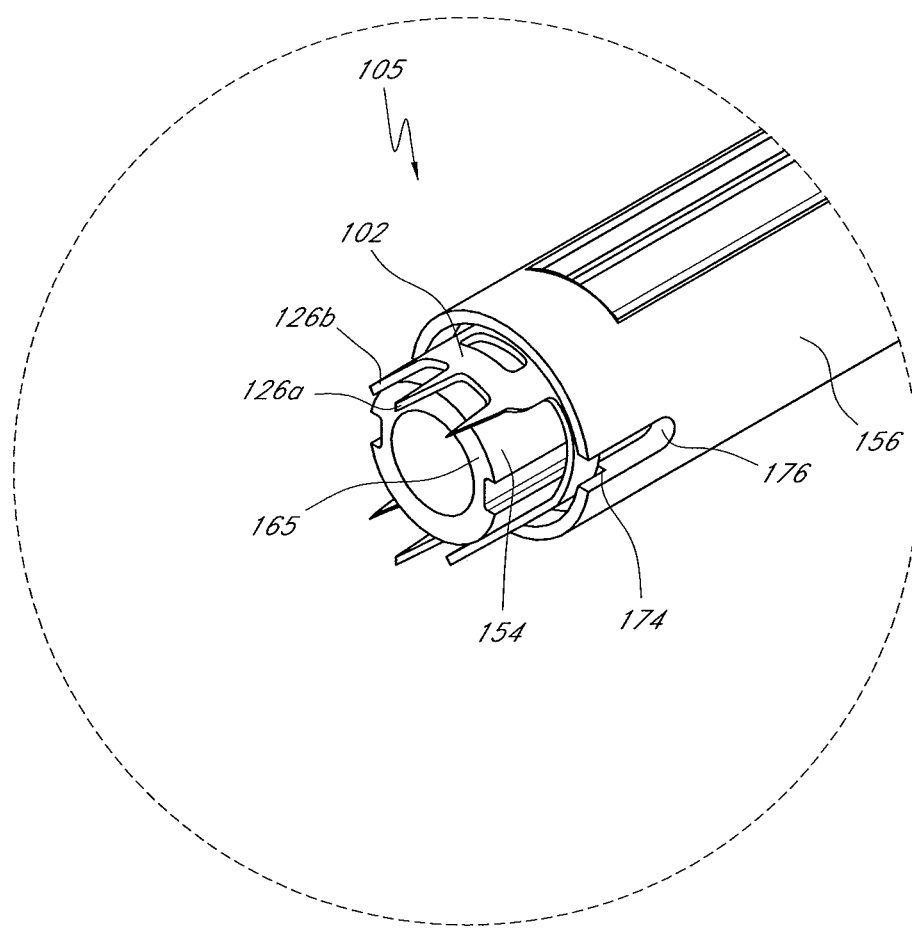
FIG. 25 is a close-up view of the distal end of the deployment instrument of FIG. 24.
Figure 26:
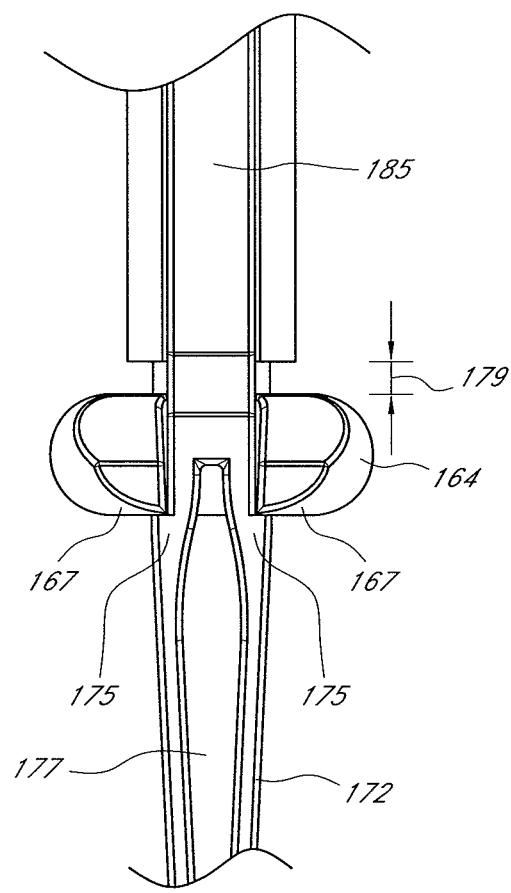
FIG. 26 is a close-up bottom view of the proximal end of the deployment instrument of FIG. 24 showing the handle engaging the stop element.
Figure 27:
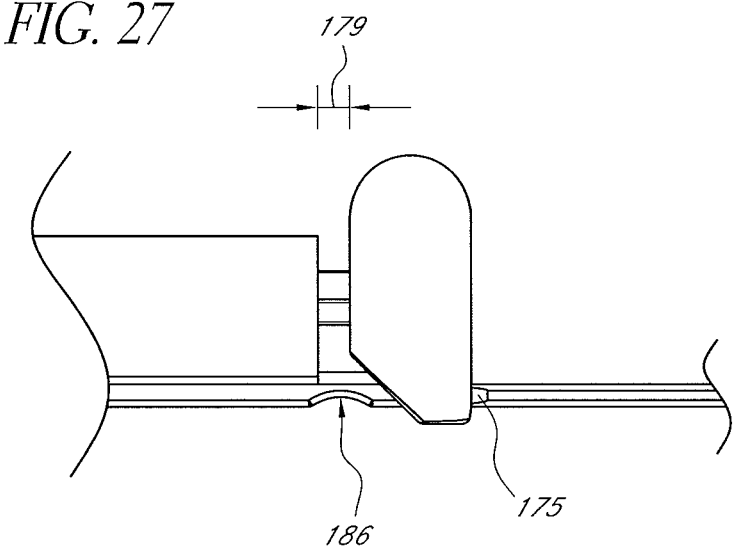
FIG. 27 is a side view of the proximal end of the deployment instrument of FIG. 24 showing the handle engaging the stop element

FIGS. 24-29 illustrate an example of a method of producing partial deployment. FIG. 24 shows a perspective view of the deployment instrument 104 in a partially-deployed state, and FIG. 25 shows a close-up view of the distal end 105 of the deployment instrument 104 in its partially-deployed state. Handle 164 can be withdrawn until the proximal face 167 of handle 164 contacts the stops 175, generally arresting further withdrawal as shown in FIGS. 26 and 27. Stops 175 generally prevent the medical professional from fully deploying the clip prematurely and ensure the clip 102 is partially deployed to an appropriate depth. Stop 175 is configured to allow the handle 164 to travel a known, limited distance 179. In embodiments where the tips 127a,b of tines 126a,b are initially aligned with distal end 165 of inner tube 154, distance 179 can also correspond to a depth of the tines' insertion into the vessel wall 116. In certain embodiments distance 179 can be greater than or equal to about 0.5 mm and/or less than or equal to about 4 mm, such as about 2 mm. Distance 179 can be different depending on the specific application or clip being utilized.

Figure 28:
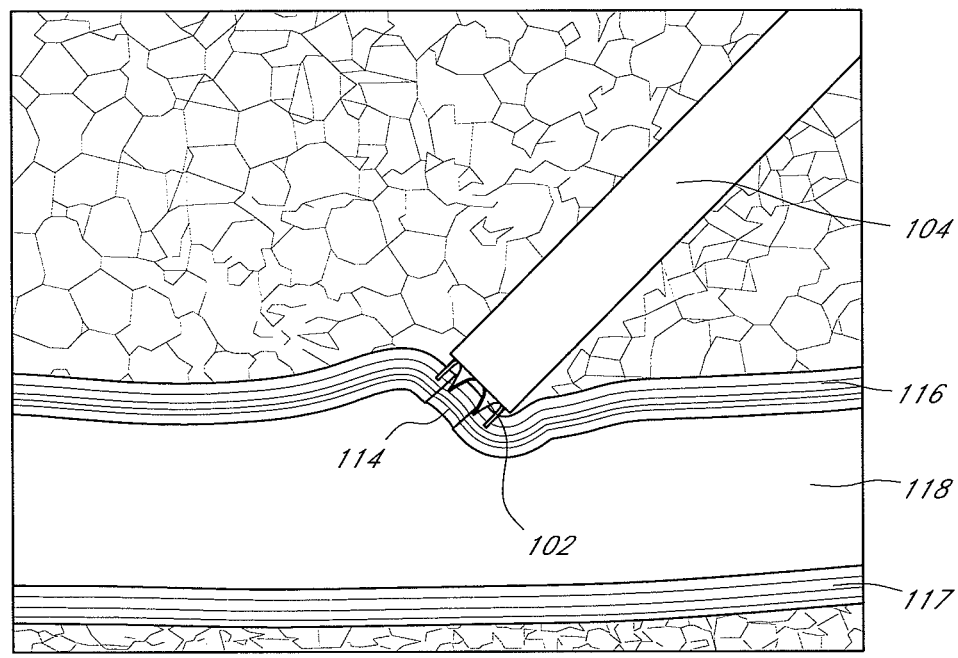
FIG. 28 is a side view of the deployment instrument of FIG. 24 in a partially deployed state after withdrawing the vascular introducer.

With the clip 102 partially deployed in the vessel wall 116, the tubular medical device 108 is no longer needed to guide the deployment instrument 104 to the arteriotomy and hence the tubular medical device 108 can then be removed from the vessel 118 as shown in FIG. 28. Removing the tubular medical device 108 prior to full deployment prevents the clip 102 from closing over the tubular medical device 108. Partially deploying the clip 102 helps to position the deployment instrument 104 more accurately and temporarily secure it in place while the tubular medical device 108 is removed.

Figure 29:
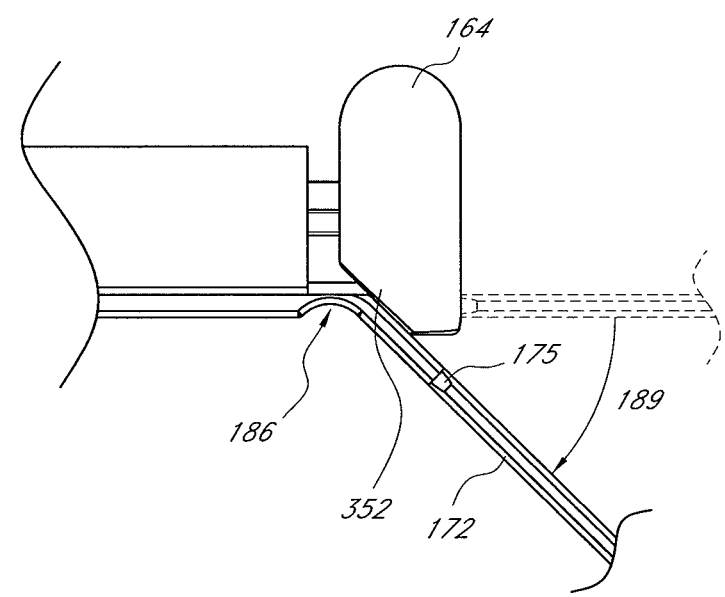
FIG. 29 is a side view of the proximal end of the deployment instrument of FIG. 27 showing how the stop element can be overcome.

Once the tubular medical device 108 is removed from the vessel, the stops 175 can be overcome by bending tab 172 in the direction of the arrow 189 shown in FIG. 29 to allow full linear movement of the inner tube 154. Tab 172 can thus operate as a releasing element, permitting the stops 175 to be overcome. Recessed or weakened portion 186 of tab 172 may facilitate bending. The flattened bottom portion and angled faces 352 of handle 164 can reduce the amount that tab 172 is required to bend in order to overcome stops 175. In some embodiments where deployment instrument 104 is disposable and configured for one-time use, tab 175 may be configured to snap off. Other appropriate stop means and methods for overcoming the stop means can also be used.

Figure 31:
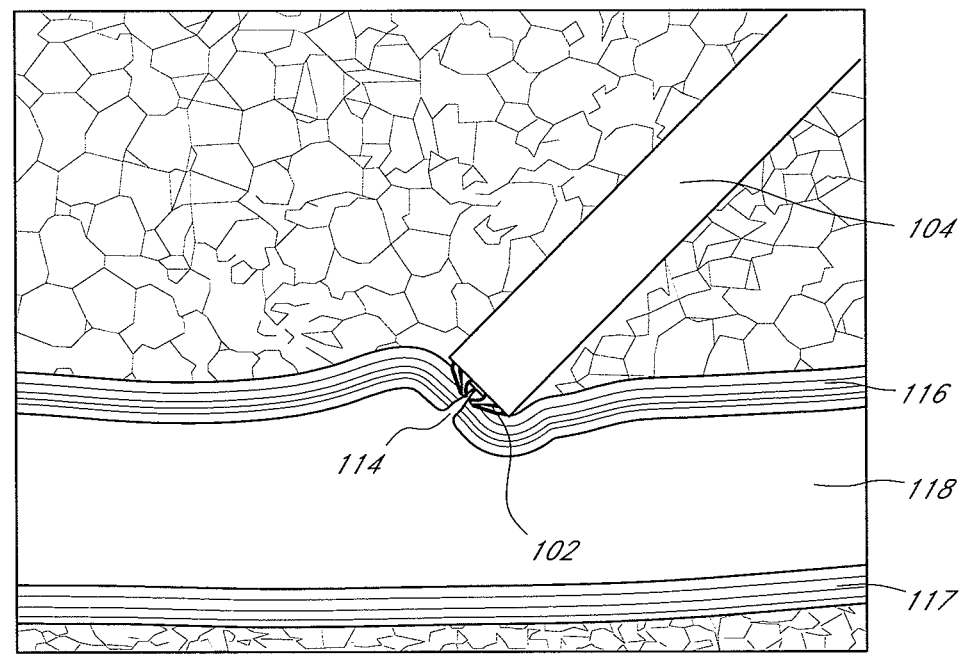
FIG. 31 is a side view of the deployment instrument of FIG. 7 in a fully deployed configuration which shows the vascular closure clip closing the arteriotomy.
Figure 30:
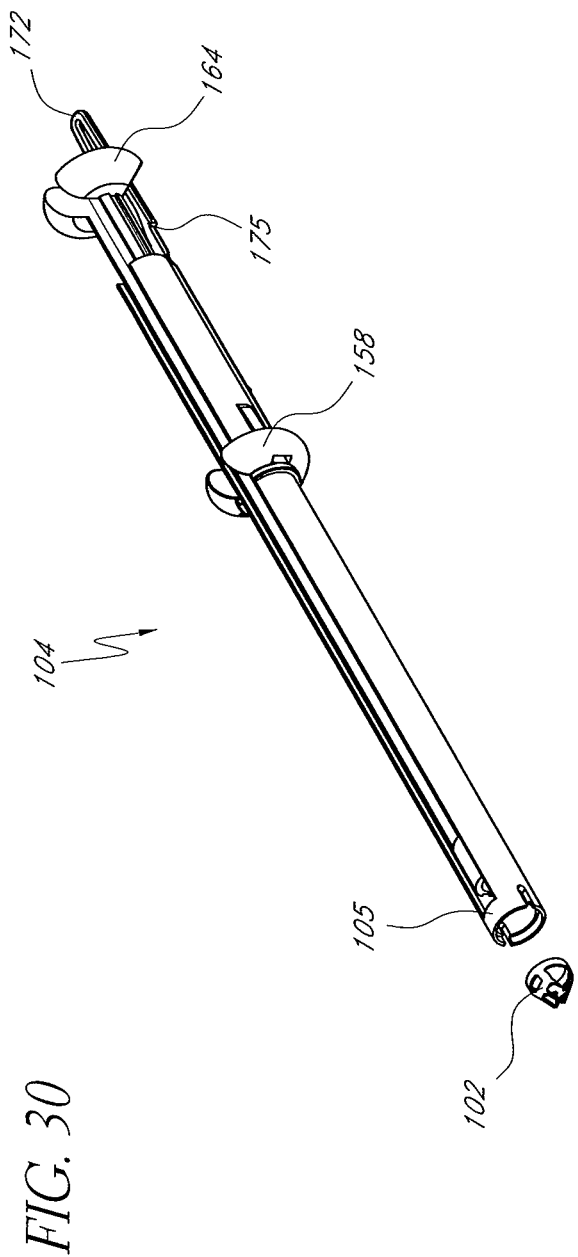
FIG. 30 is a perspective view of the deployment instrument of FIG. 7 in a fully deployed configuration.

With reference to FIGS. 30-31, the medical professional then continues to withdraw inner tube 154 until the clip 102 is forced off of or advanced past the distal end 105 of the deployment instrument 104. The opposed fingers 122, 124 of the clip 102 fold inwardly, drawing together sides of the vessel tissue from an outside surface of the vessel to close the arteriotomy 114 as shown in FIG. 31. Closing the arteriotomy can, but does not necessarily, result in complete mechanical closure of the opening. Instead, the term "close" in this context can refer to any facilitation of hemostasis. Thus, in certain embodiments, sides of the vessel tissue may not necessarily touch. Generally, the sides of the vessel tissue are brought closer to together to reduce the size of the opening 114 in the vessel 118 and thereby facilitate hemostasis.

Figure 32:
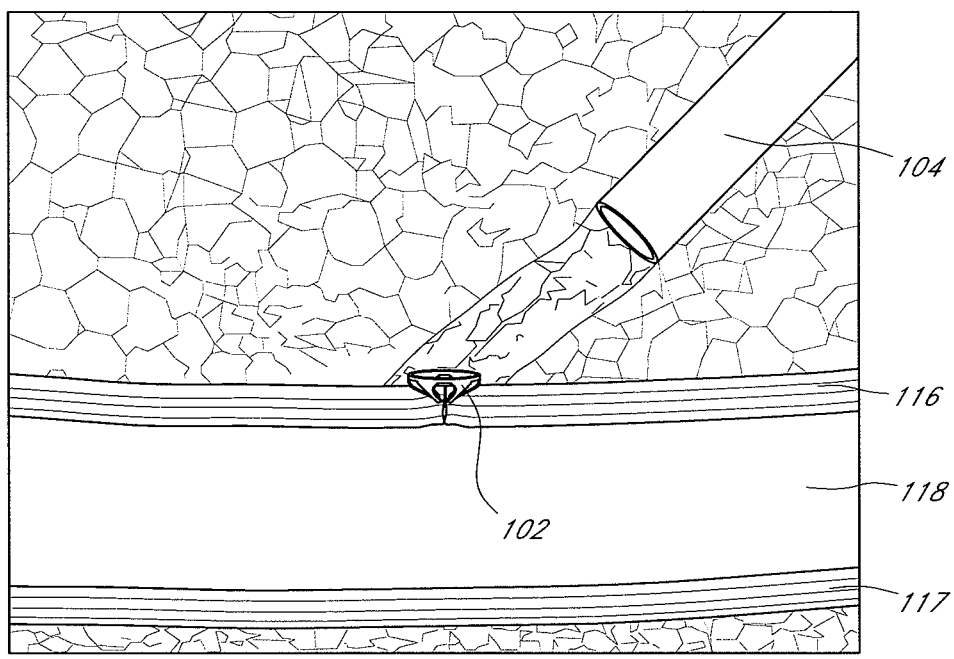
FIG. 32 is a side view of the deployment instrument of FIG. 7 showing the deployment instrument being removed from the patient's body following deployment.

FIG. 32 shows the deployment instrument 104 being withdrawn following successful deployment of the clip 102. Clip 102 can be biocompatible and configured for permanent implantation. Accordingly, in certain embodiments a patient may be discharged following confirmation of successful clip deployment and hemostasis.

In some embodiments, vascular closure system 100 can be completely or substantially extravascular in that the deployment instrument or closure device is not required to penetrate into the interior region of blood vessel 118. This reduces or eliminates the amount of foreign material introduced into contact with the patient's blood stream, thus reducing the risk of infection, blockage, or other complications. For example, in certain embodiments a posterior support is not required during deployment of the clip. In some systems, the use of posterior support may disadvantageously require that a portion of the deployment tool or closure device be positioned in the blood vessel during or following deployment. The use of a posterior support element within the vessel may require complicated mechanisms to facilitate its removal following deployment. The safe deployment of the clip without requiring posterior support can be facilitated through use of a partial deployment technique as described above and by the application of a controlled amount of external pressure via a pressure element or other pressure sensing means. In addition, the use of a clip with appropriately-sized tines to prevent overinsertion can also facilitate deployment without posterior support.

The system 100 described above can also be compatible with standard commercially available introducers already used in standard vascular interventional or diagnostic procedures. This can eliminate the need to purchase and use specialized and costly additional or different equipment or to change the way that the interventional or diagnostic procedures are performed, thus reducing the accompanying risks.

Figure 33:
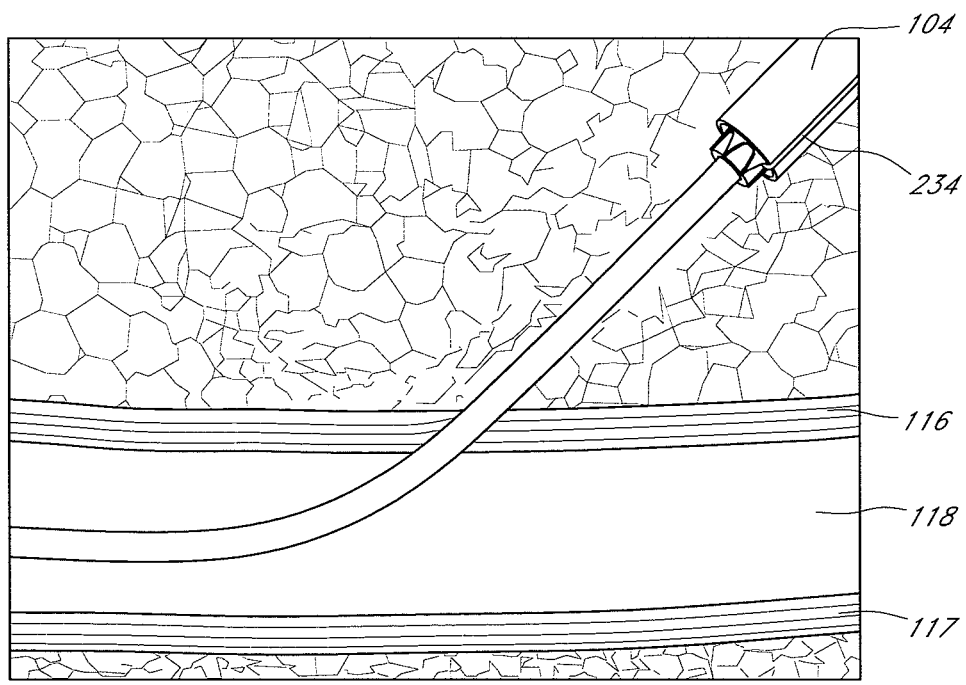
FIG. 33 is a side view of a vascular closure procedure utilizing a removable clip, showing the deployment instrument being advanced over the vascular introducer.
Figure 34:
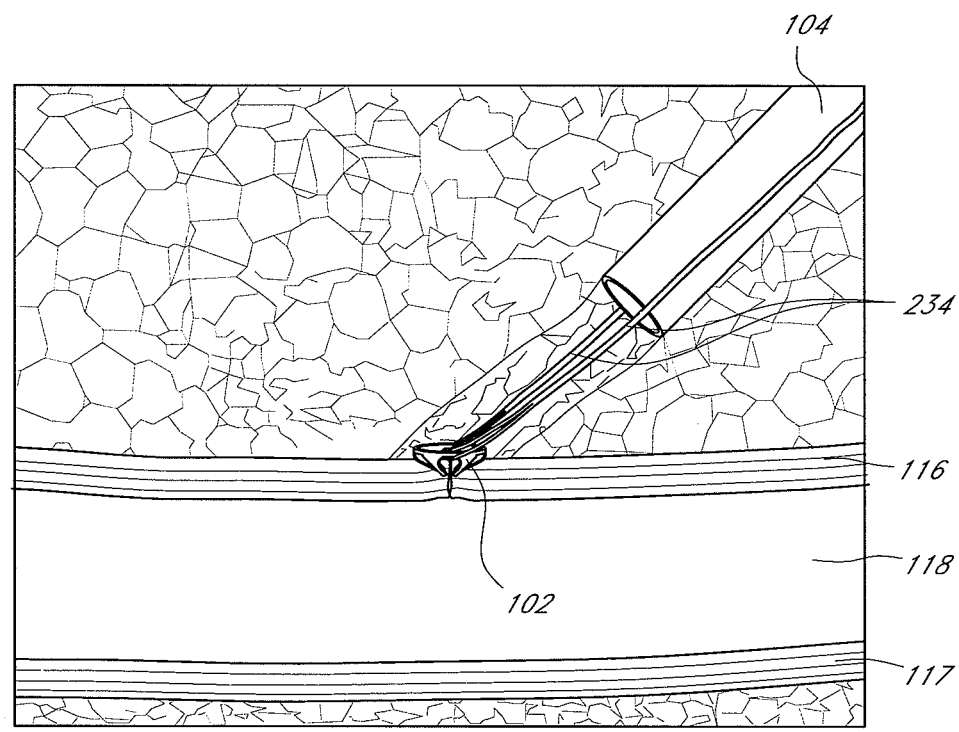
FIG. 34 is a side view of the procedure of FIG. 33 showing the deployment instrument being removed after deploying the clip.
Figure 35:
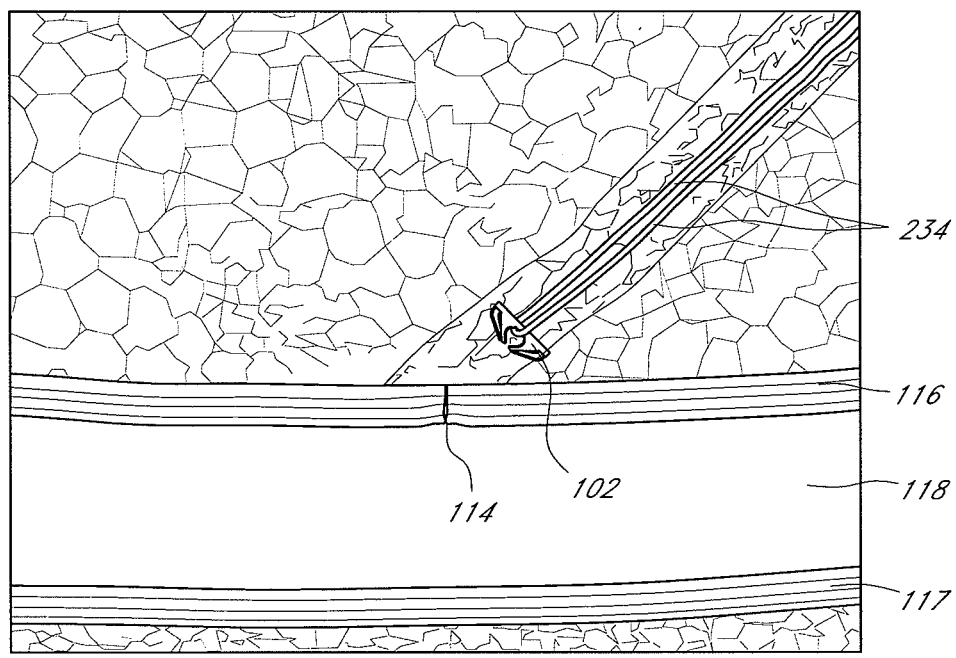
FIG. 35 is a side view of the vascular closure procedure of FIG. 33 showing the vascular closure clip being removed from the patient's body following hemostasis.
Figure 36:
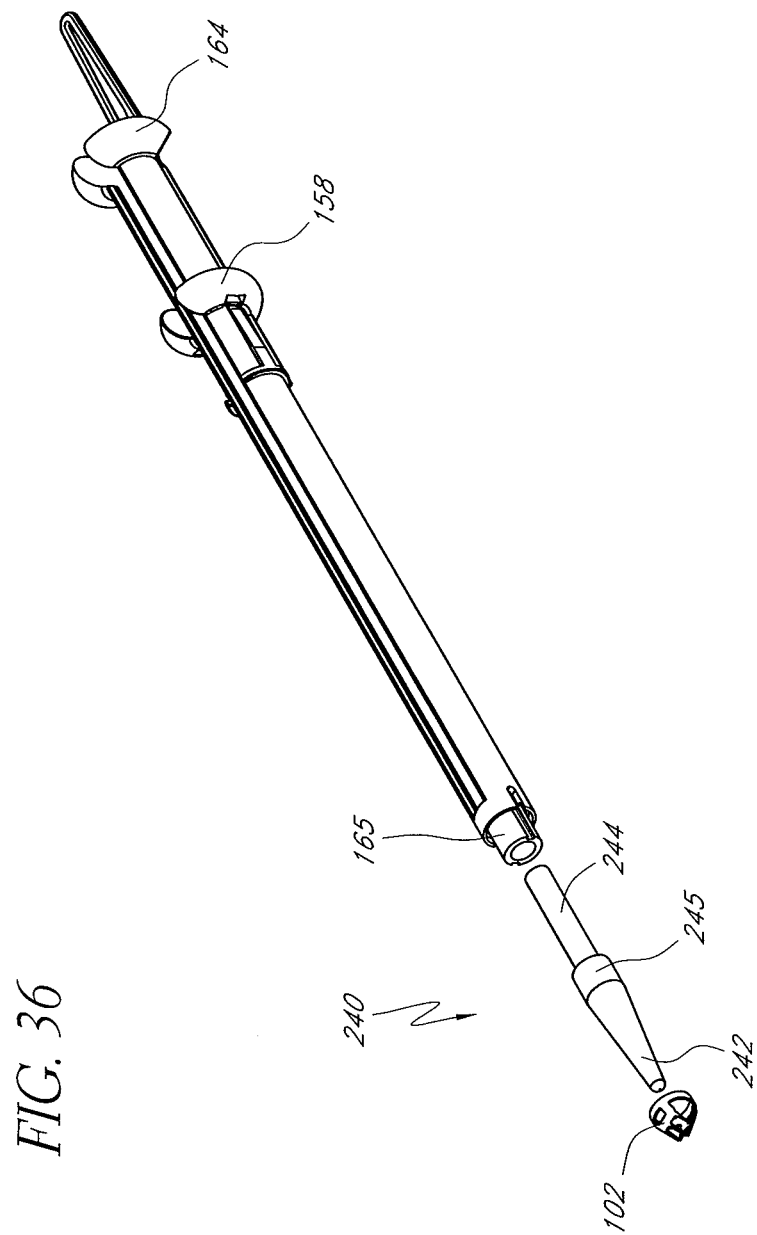
FIG. 36 is a perspective view of a clip loading mechanism.

FIGS. 33-35 illustrate an example of a method of temporarily implanting a clip 102. In certain embodiments, a vessel closure clip 102 can be removable and configured for temporary implantation as illustrated in FIG. 33. In embodiments utilizing temporary closure, one or more suture lines 234 or other suitable tethering means can be secured to the clip 102 and positioned along the outer surface of the outer tube 156 prior to insertion. The suture lines 234 can be tied to the clip 102 or looped through window portions 125 or other openings provided on the clip 102 for this purpose or attached in some other way. In certain embodiments, the clip 102 and deployment instrument 104 may be provided to the medical professional with suture lines 234 attached. In other embodiments, suture lines 234 may be attached by the medical professional prior to use. Slots 176 on the distal end 173 of outer tube 156 (see FIG. 8) can facilitate access to the clip 102 for the purposes of securing the suture lines 234 to the clip 102 after it is loaded onto the deployment instrument 104. The distal ends of axial grooves 160 on inner tube 154 can allow the suture lines to be passed under base portion 120. In certain embodiments, the suture lines 234 can be tied or secured to the clip before it is loaded on the deployment instrument 104. The suture lines 234 can run along the outer surface of outer tube 156 as shown in FIG. 33. In other embodiments, the suture lines 234 can run along an interior of the deployment instrument 104. In certain embodiments, the deployment instrument 104 can include channels specifically adapted to accommodate suture lines 234.

The removable clip 102 can be temporarily implanted utilizing the procedure outlined above. The proximal ends of the suture lines 234 can be left extending outside of the patient's body while the clip 102 remains implanted. After a period of time sufficient to achieve hemostasis, the medical professional can pull on the suture lines 234 to remove the clip as seen in FIG. 35. The closure force of the clip can be configured so that force applied to the suture lines 234 causes the fingers 122, 124 to temporarily open, allowing the clip 102 to be safely removed without reopening the arteriotomy 114 or damaging the vessel wall 116. In certain embodiments, the clip 102 can include another or alternative release mechanism that can be triggered via the suture lines 234. The release mechanism can cause the fingers 122, 124 to open to facilitate removal of the clip 102. In embodiments using a shape memory clip, the clip can be cooled until it transforms to its martensite phase, making it more easily deformed and lowering the amount of force required to open the clip's fingers and withdraw it. The clip 102 can be cooled via insertion of a cold probe or via application of an externally-applied cold source such as an ice pack. In addition or in the alternative, an infusing syringe can be used to deliver a cooled liquid such as chilled saline to the clip. In certain embodiments, the clip 102 can exhibit a two-way shape memory effect and cooling the clip 102 can return it to its second memorized configuration which can be, for example, an open configuration. The clip's composition and treatment can be selected to achieve desired phase transition temperatures to facilitate such an approach.

The time required to achieve hemostasis can vary from patient to patient depending on a variety of factors including the patient's age, sex, medical condition, medications, and the presence of anti-clotting agents that can have been used during the medical procedure. Under certain conditions, clip 102 can be removed after about 10 minutes, after about 20 minutes, or about 40 minutes.

In some embodiments, it can be desirable to use suture lines 234 even in clips intended for permanent implantation in order to enable emergency removal. In this arrangement, the medical professional can deploy the clip utilizing the procedure described above. Once it is determined that the clip has been successfully deployed, the medical professional can cut the suture lines 234 and completely withdraw them from around the clip.

The deployment instrument 104 can be partially or completely made from one or more of the following materials: polymers, including Nylon, polyamide, polycarbonate (e.g., Makrolon®), polyester, polyethleneteraphthalate (PET), polyetherethereketone (PEEK), polyimide, superelastic/shape memory polymers, metals including spring steel and stainless steel, metal alloys including Nitinol, 17-7 PH, Elgiloy, and Inconel, or ABS. Other suitable materials can also be used. The deployment instrument 104 can be completely or partially fabricated using one or more of the following methods: casting, extrusion, laminating, machining, molding (injection or other), sintering, stereo lithography. Other suitable methods can also be used.

As illustrated, in certain embodiments, the deployment instrument 104 can be constructed using relatively few components, e.g., an inner tube, an outer tube, and a pressure element. Each of the components can be produced inexpensively via injection molding. In certain embodiments, the deployment instrument 104 can be disposable and designed for single use. Alternatively, the deployment instrument 104 can be designed for repeated use following sterilization.

Figure 37:
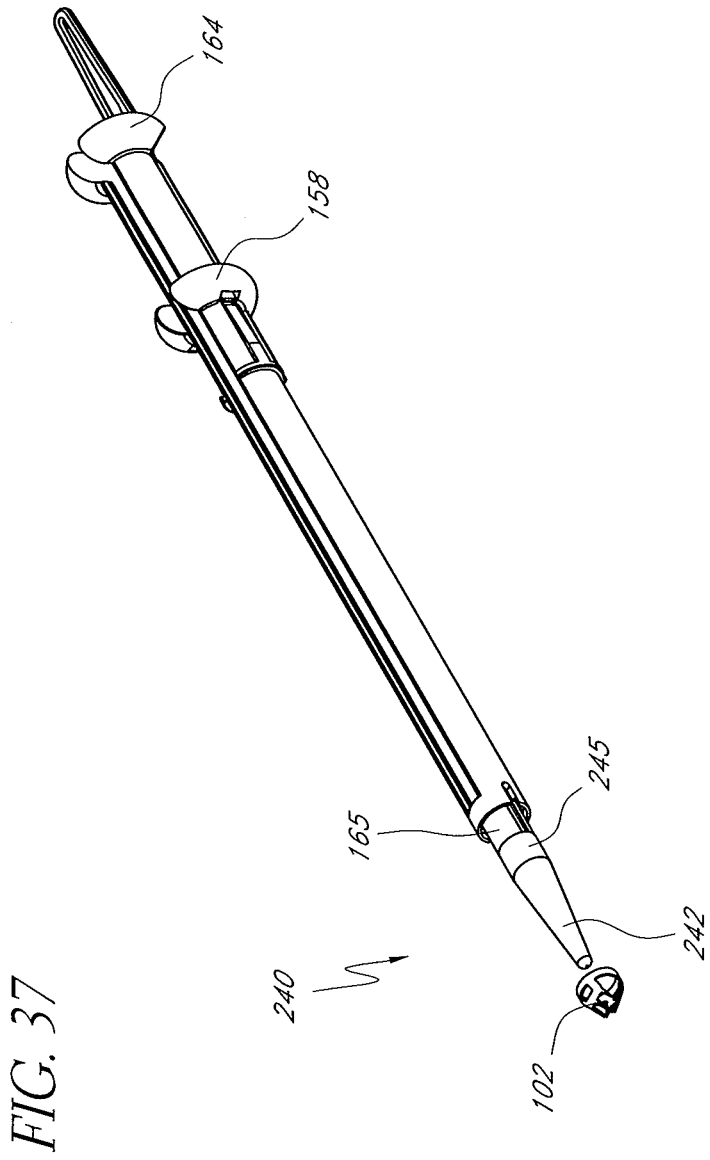
FIG. 37 is a perspective view of the clip loading mechanism of FIG. 36 fully inserted into the distal end of the deployment instrument.
Figure 38:
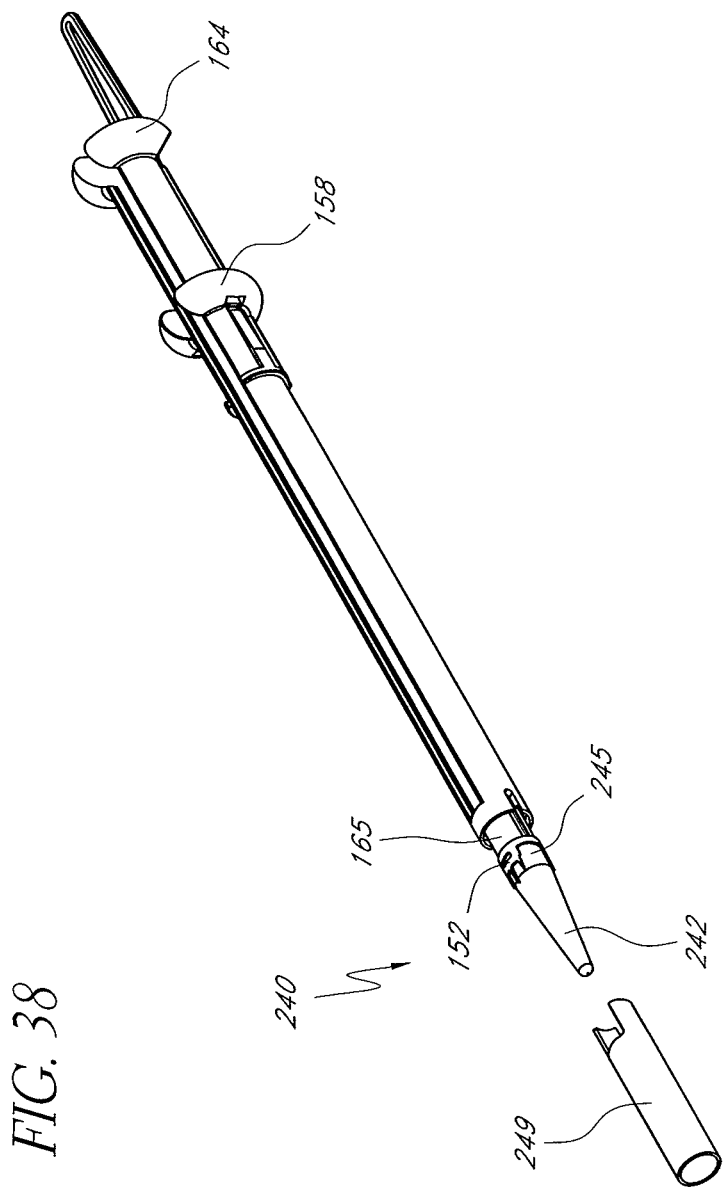
FIG. 38 is a perspective view of a pusher tool configured to mate with a vascular closure clip to fully advance the clip over the clip loading mechanism of FIG. 36 and onto the distal end of the deployment instrument.
Figure 39:
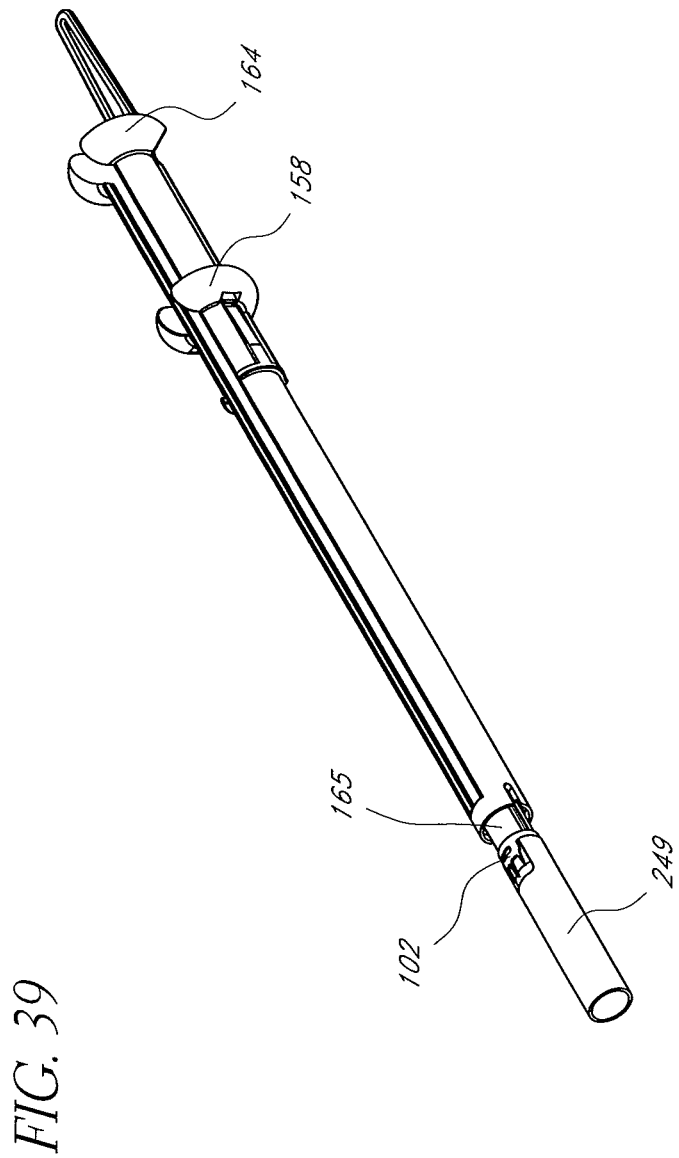
FIG. 39 is a perspective view of the pusher tool of FIG. 38 fully advancing the clip onto the distal end of the deployment instrument.

A method for loading the clip 102 onto the deployment instrument 104 will now be described with reference to FIGS. 36-39. A loading mechanism 240 can be used to facilitate loading the clip 102 onto the distal end 165 of inner tube 154. Loading mechanism 240 includes a proximal section 244 which mates with the inner tube's inner lumen as seen in FIG. 37. Clip 102 is then advanced over tapered distal section 242 of loading mechanism 240. Distal section 242 gradually forces apart the clip's fingers 122, 124 as shown in FIG. 38. The loading mechanism 240 can also include an intermediate section 245 with a substantially constant circumference which can be substantially equal to that of inner tube 154. A pusher mechanism 249 can be used to advance the clip over the loading mechanism 240 and onto the deployment instrument 104. Pusher mechanism 249 can include an end geometry configured to mate with the distal end of clip 102 as seen in FIG. 39. Once the clip 102 has been fully loaded onto the deployment instrument 104, the pusher mechanism 249 and loading mechanism 240 can be removed. In embodiments using a superelastic or shape memory clip, the clip 102 can be cooled until it undergoes a martensite phase transformation in order to facilitate the clip's deformation. During its martensite phase, the clip 102 is more easily deformed and thus the fingers 122, 124 can be more readily spread apart in order to load the clip 102 onto the deployment instrument 104. Such an approach can be used as an alternative to or in addition to the loading procedure described above.

Figure 40:
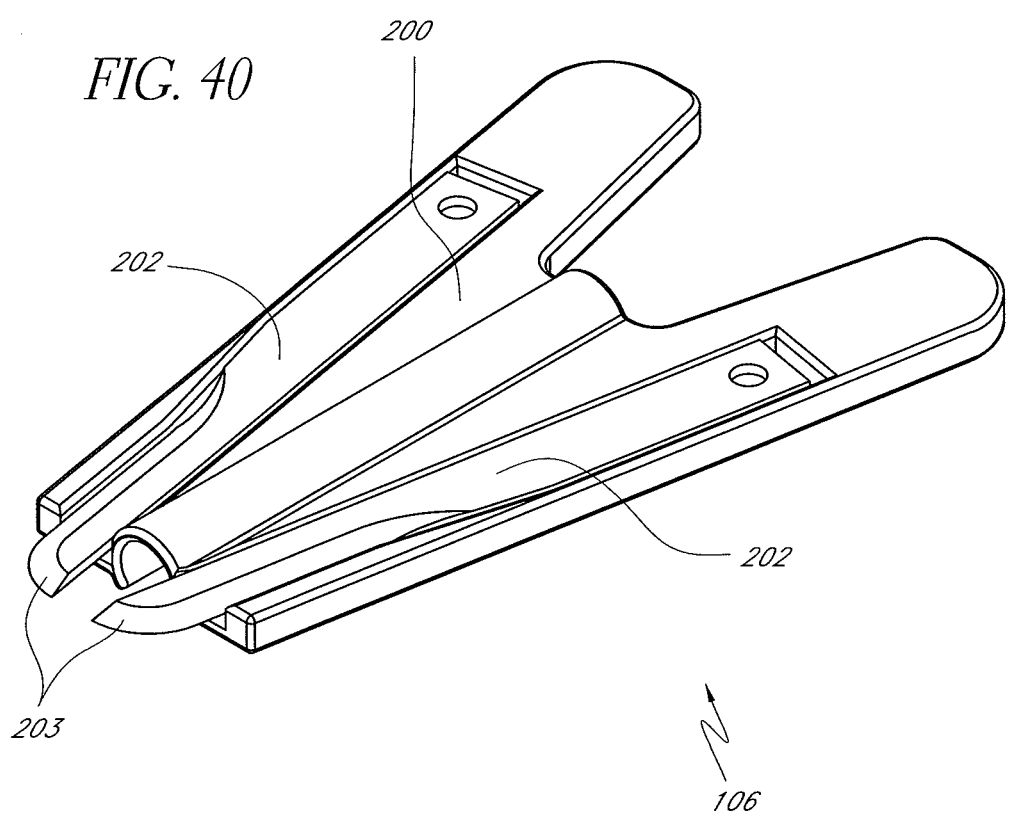
FIG. 40 is a bottom view of a slidable tissue cutter.
Figure 41:
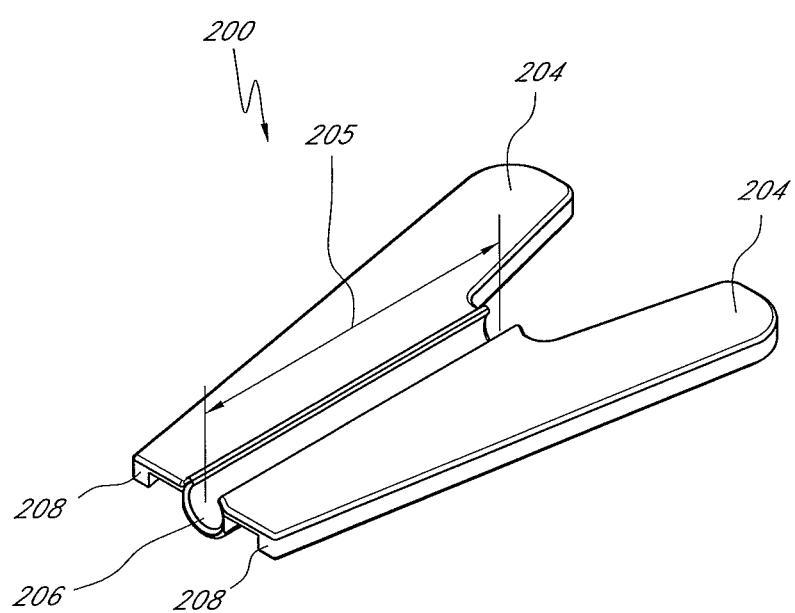
FIG. 41 is a perspective view of the slidable tissue cutter of FIG. 40.
Figure 42:
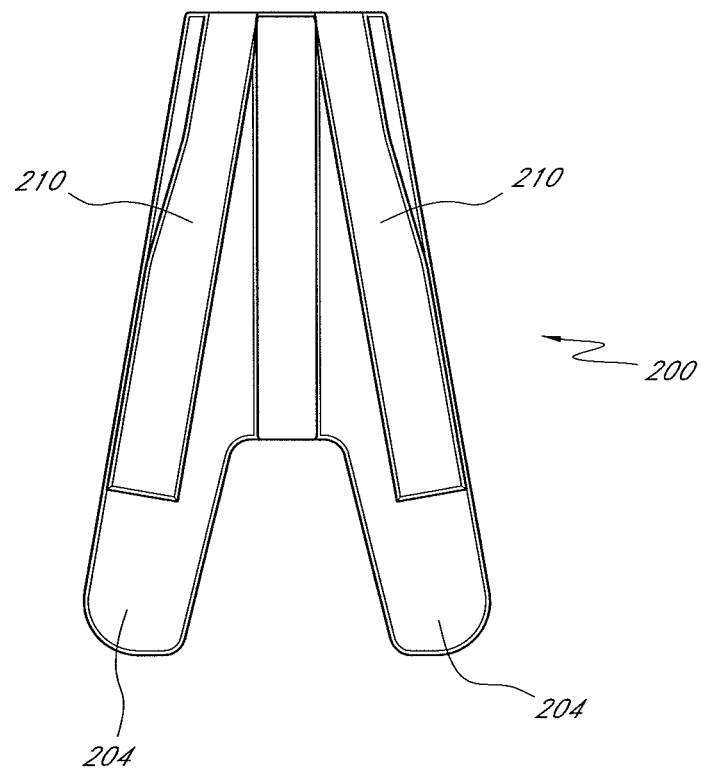
FIG. 42 is a bottom view of a frame which can constitute a first component of the slidable tissue cutter of FIG. 40.

FIGS. 40-42 illustrate an example of a tissue opening widener such as a guided slidable tissue cutter 106, which can be utilized in a vessel closure system 100 in certain embodiments. After completing the desired medical procedure, the medical professional can temporarily attach tissue cutter 106 by clipping it onto the tube section 110 of the vascular introducer 108 as shown in FIG. 1. The tissue cutter 106 can then be slidably advanced along the vascular introducer sheath 108. The cutter 106 can be configured to make an incision of a precise depth and width at the site of the percutaneous opening 112 using sharp distal edges 203 of blades 202. The cutter 106 generally positions the edges 203 of the blades 202 at a specific orientation and distance from the tube 110 to permit a consistently and modestly sized entry point for the deployment instrument 104. A ledge such as mechanical stops 208 can ensure that the incision is not any deeper than needed to facilitate entry of the deployment instrument 104. Utilizing the existing introducer sheath 108 as a guide for the slidable tissue cutter 106 also assists in ensuring proper placement of the incision. After making the incision, the slidable tissue cutter 106 can be removed from the side of the vascular introducer.

Figure 43:
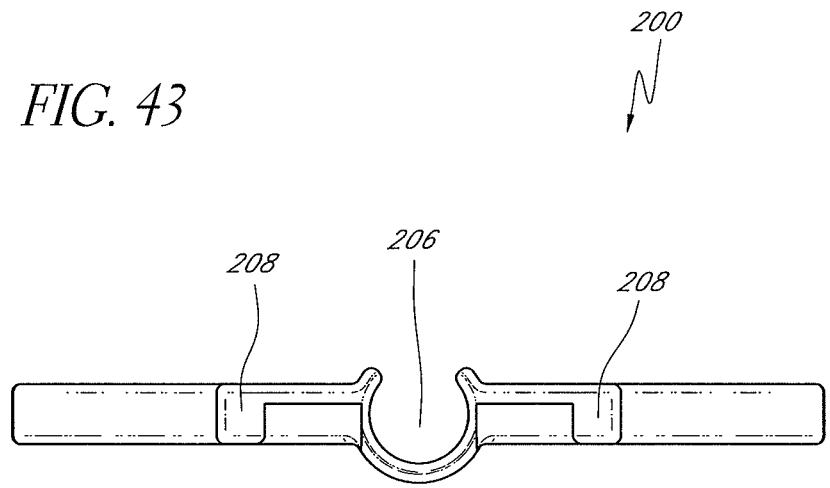
FIG. 43 is a distal end view of the frame of FIG. 42.

FIGS. 41-43 illustrate an example of a frame portion 200 which can form a component of a slidable tissue cutter 106. In certain embodiments, scalpel blades 202 can be secured to frame portion 200. In other embodiments, the cutter 106 can utilize specialized blades and/or be formed from a single piece. As illustrated, slidable cutter 106 includes two blades 202 positioned on lateral sides, such as in a diametrically opposite position from one another. In other embodiments, a single blade or three or more blades can be used. In certain embodiments, the cutting surfaces of each blade 202 can be static and configured to cut tissue without requiring interaction with a second cutting surface. In other embodiments, dynamic blades can be used.

Slidable cutter 106 can include a channel 206 with a partial circumferential cross-sectional geometry as shown in FIG. 43. This geometry enables a "snap-on" feature permitting the cutter 106 to be easily and temporarily attached to the tubular medical device and facilitating removal of the cutter 106 once the desired tissue has been cut. In other embodiments, a slidable cutter can utilize two mating pieces that clamp or snap together to facilitate temporary attachment and removal. In a preferred embodiment, channel 206 is sized so as to be compatible with any commercialized introducer sheath. The ends 208 of the frame portion 200 act as mechanical stops to control the depth of the incision. In some embodiments, handle portions 204 can extend beyond the end of channel 206 to facilitate handling by the medical professional at a distance from the sharp edges 203. Advantageously, such a configuration can facilitate the medical professional's control of the instrument without requiring an increase in the length 205 of channel 206. Most commercially available vascular introducers are between 11 and 13 cm long. Once inserted into a patient's vessel, the exposed portion of the introducer's tube section can be relatively small. Thus, it can be desirable to limit the amount of tube section that is taken up by the attached cutter and hence to reduce the length 205 of channel 206. The proximal ends of the handle portions 204 can be flared outwardly as illustrated to provide increased space between the cutter 106 and the tube 110 for improved manual access and manipulation, and to permit the deployment instrument 104 to be positioned as close axially as possible to the generally short exposed length of tube 110. The lateral edges of the cutter 106 can be tapered as illustrated.

Frame 200 can include recesses 210 sized to receive scalpel blades 202. The recesses 210 can be used to shield portions of the blades 202 not intended to be used to cut tissue. Scalpel blades 202 can be secured to frame 200 via one or more of a variety of known methods such as, for example, friction-fitting, mechanical interference fitting, sonic welding, adhesives, screws, clamps, and the like. As illustrated, scalpel blades 202 are configured to angle inward toward one another slightly. Such a configuration can help to ensure that the blades 202 cut tissue immediately adjacent to the percutaneous opening 112. In other embodiments, scalpel blades 202 can be oriented in a substantially parallel configuration. In some embodiments, the blades 202 can be adjustable, allowing a medical professional to adjust one or more of the incision's depth, width, and angle, and/or a collection of cutters 106 of different sizes can be provided for different applications. In certain embodiments, slidable tissue cutter 106 is configured to cut substantially only the patient's skin. Fatty tissue located beneath the skin will generally move out of the way of the deployment instrument 104 with minimal resistance. Accordingly, a deeper incision may not be necessary in some embodiments.

The cutter 106 can be made from one or more of the following materials: polymers, including nylon, polyamide, polycarbonate (including Makrolon®), polyester, polyethyleneteraphthalate (PET), polyetheretherketone (PEEK), polyimide, superelastic/shape memory polymers, metals, including spring steel and stainless steel, and/or metal alloys including Nitinol, 17-7 PH, Elgiloy, Inconel, or ABS. Other appropriate materials can also be used. In embodiments utilizing a "snap-on" feature the frame 200 can be sufficiently flexible to allow the walls of the channel to bend outwardly to accommodate the tubular medical device 108. The slidable cutter 106 can be completely or partially fabricated using one or more of the following methods: casting, laminating, machining, molding (injection or other), sintering, stereo lithography. Other suitable methods can also be used. Advantageously, the slidable tissue cutter 106 can be inexpensive to produce and designed for one-time use. In other embodiments, the tissue cutter 106 can be designed for repeated use following sterilization. An additional advantage of slidable tissue cutter 106 is that it allows for greater precision and ease of use than a hand-held scalpel and is less dependent upon the medical professional's skill and care.

Figure 44:
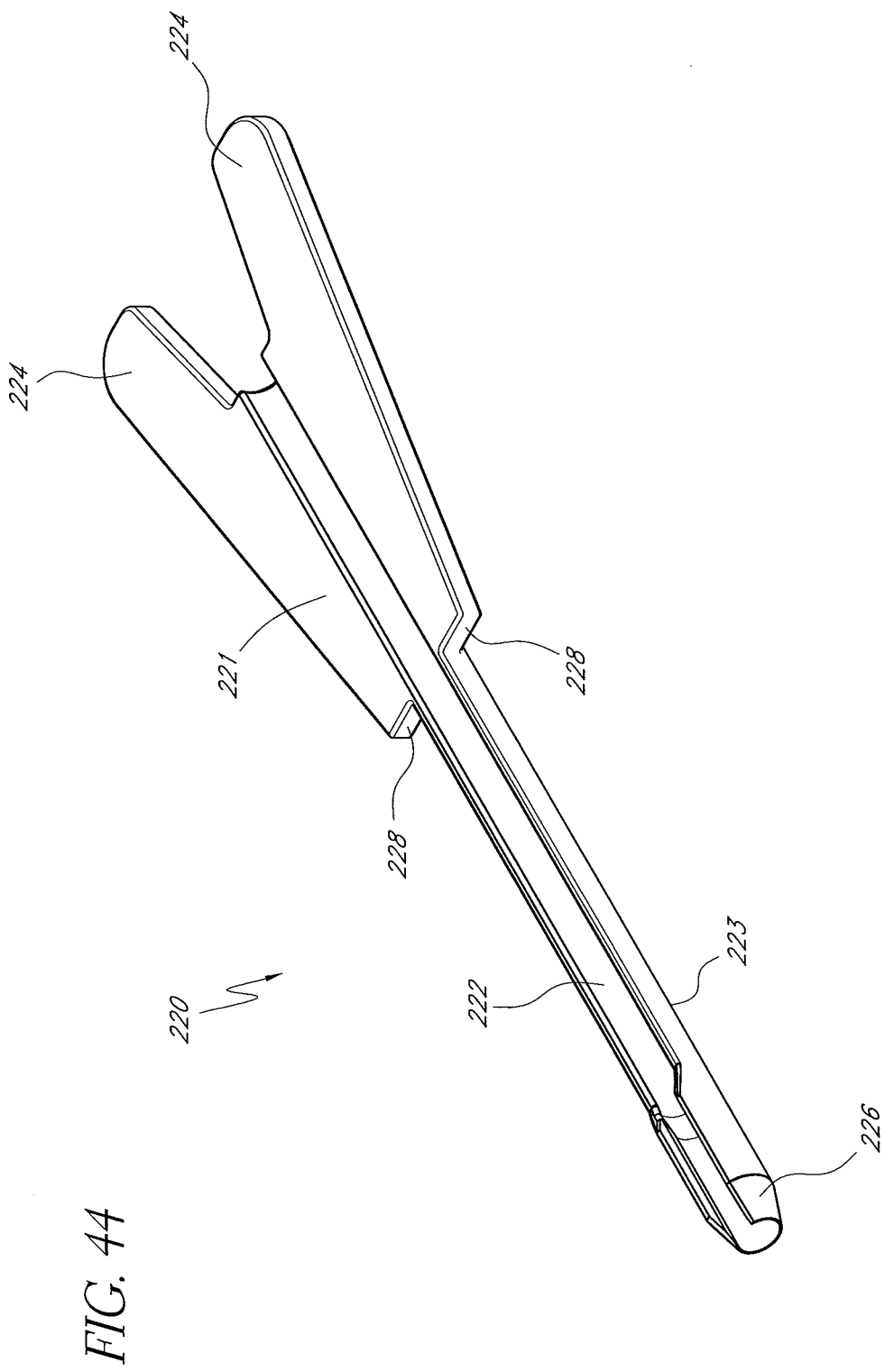
FIG. 44 is a perspective view of a slidable tissue dilator.
Figure 45:
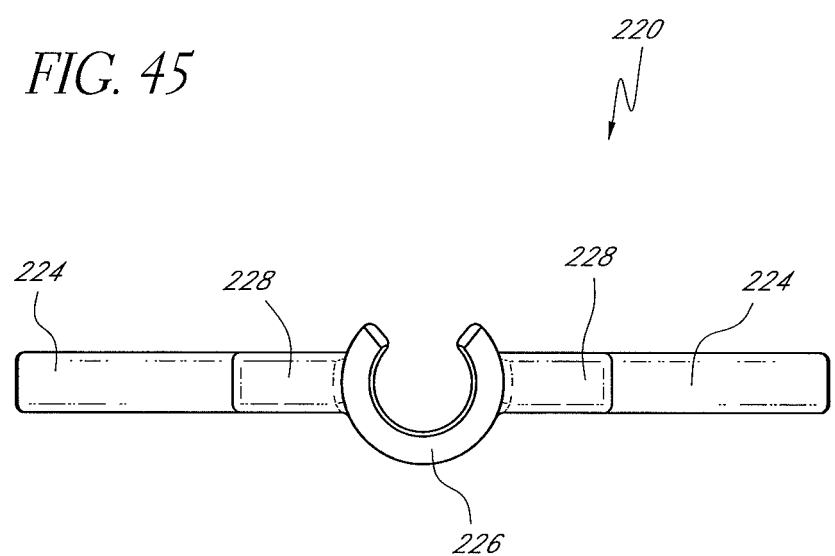
FIG. 45 is a distal end view of the slidable tissue dilator of FIG. 44.
Figure 46:
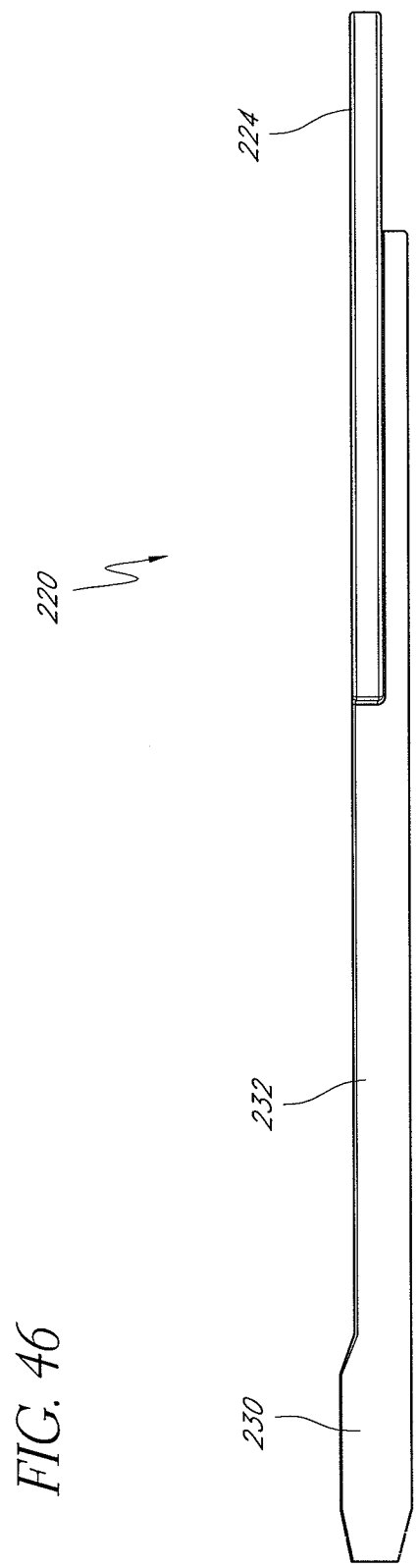
FIG. 46 is a side view of the slidable tissue dilator of FIG. 44.

FIGS. 44-46 illustrate an example of a guided slidable tissue dilator 220 which can be utilized in a vessel closure system 100 in certain embodiments. Tissue dilator 220 can be configured to dilate the tissue tract before the deployment instrument 104 and can be moved through the opening in the skin. Tissue dilator 220 can be generally tube-shaped and configured to snap onto and off of the existing introducer sheath. Dilating the tissue before the advancement of deployment instrument 104 creates a temporary pathway through the tissue, making it easier to advance the deployment instrument 104 forward to the vessel wall 116. After dilating the tissue tract, the tissue dilator 220 is then slid backwards and removed from around the introducer sheath.

Tissue dilator 220 can include an elongate tubular portion 223 with a channel 222. Tubular portion 223 can include a tapered distal end 226 to facilitate insertion of tissue dilator 220 through the percutaneous opening 112. Tissue dilator 220 can include a base 221 with handle portions 224 extending beyond the end of channel 222. As illustrated, surfaces of handles 224 can be positioned in a plane generally parallel to a longitudinal axis of tubular portion 223. In other embodiments, handles 224 can be positioned at an appropriate angle, such as, for example, an angle of at least approximately 90 degree angle. Angled handles can advantageously provide a surface to push on that is perpendicular to the direction of applied force. As with the cutter 106, ends 228 of base 221 can act as mechanical stops to limit the depth of insertion. The medical professional can advance tissue dilator 220 until its distal end 226 encounters the resistance of the vessel wall 116. As with the cutter 106, channel 222 can have a partial circumferential cross-sectional geometry enabling it to "snap on" to an introducer sheath or other medical device. In other embodiments, a tissue dilator can utilize two mating pieces that clamp or snap together to facilitate temporary attachment and removal. In the illustrated embodiment, tubular section 221 includes a distal section 230 and a proximal section 232. Distal section 230 has a greater partial-circumferential cross-section than proximal section 232. In other embodiments, tubular section 221 can be substantially uniform along its length. Tissue dilator 220 can be made from materials and methods similar to those described above with reference to tissue cutter 106.

Figure 47A:
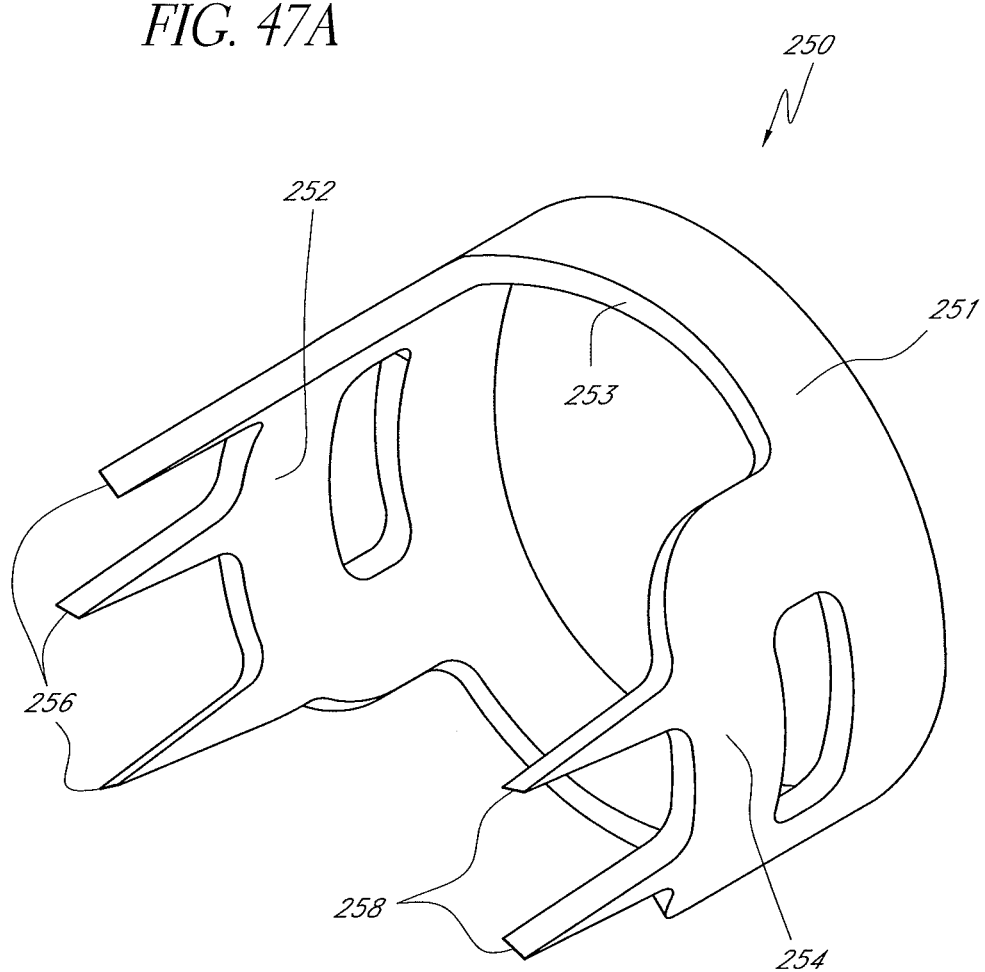
FIG. 47A is a perspective view of another embodiment of a vascular closure clip in an open configuration.
Figure 47B:
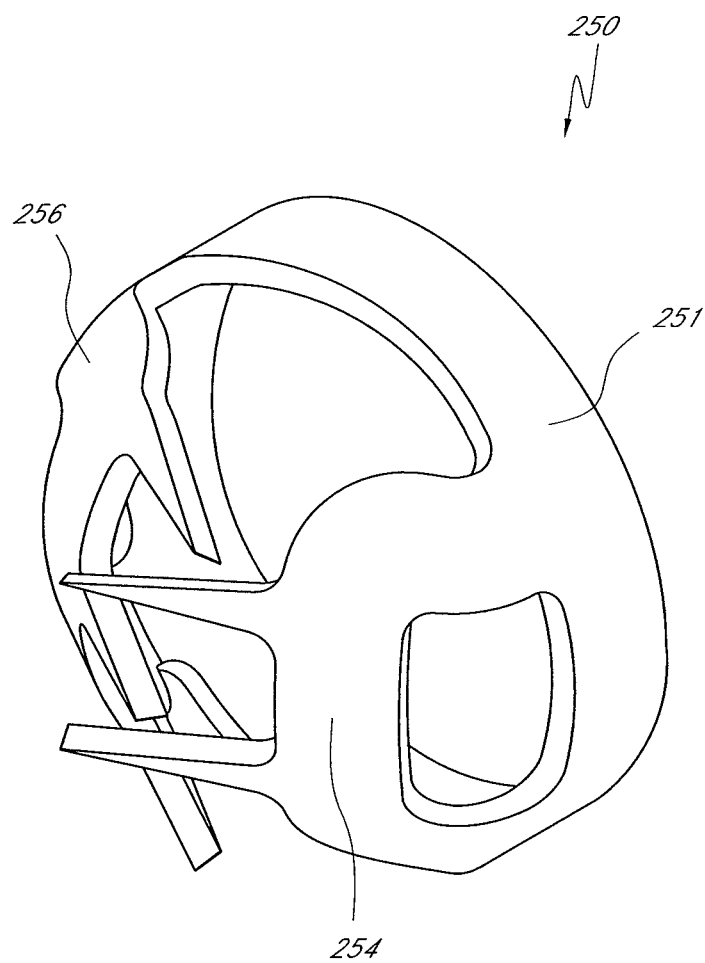
FIG. 47B is a perspective view of the vascular closure clip of 47A in a closed configuration.
Figure 47C:
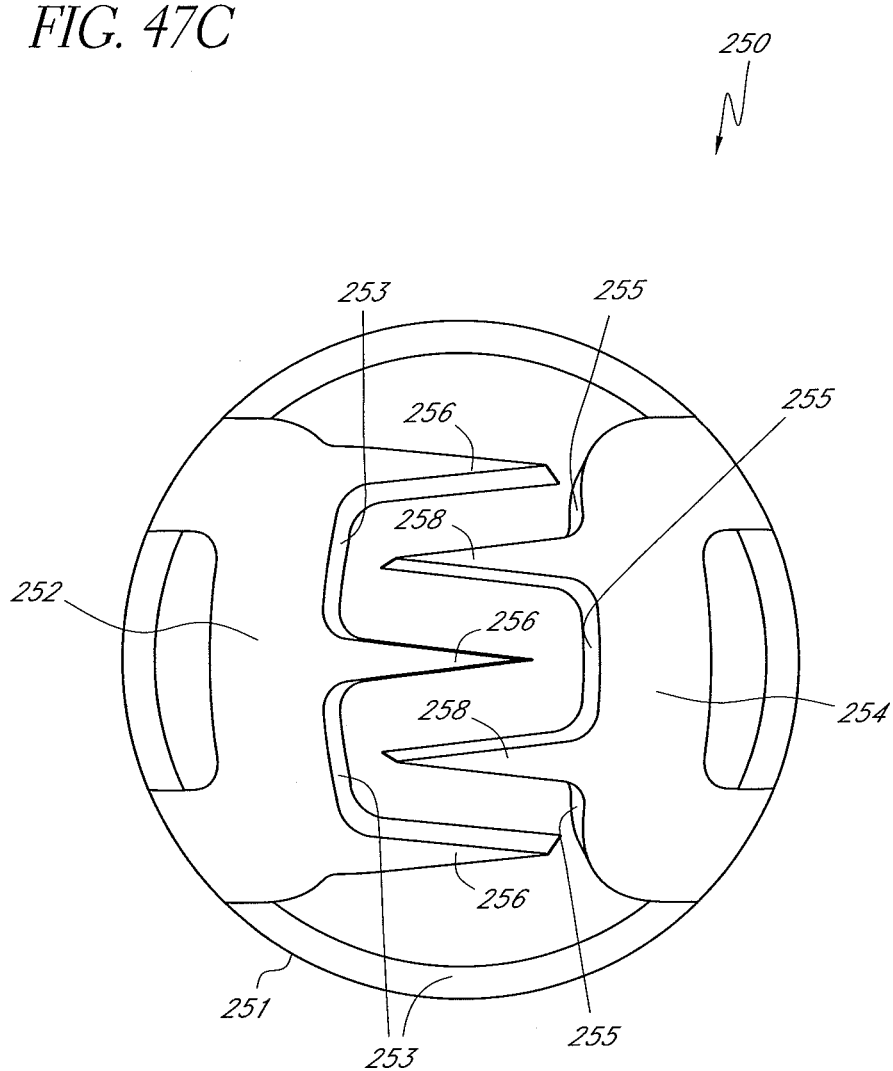
FIG. 47C is a bottom view of the vascular closure clip of 47A in a closed configuration.
Figure 47D:
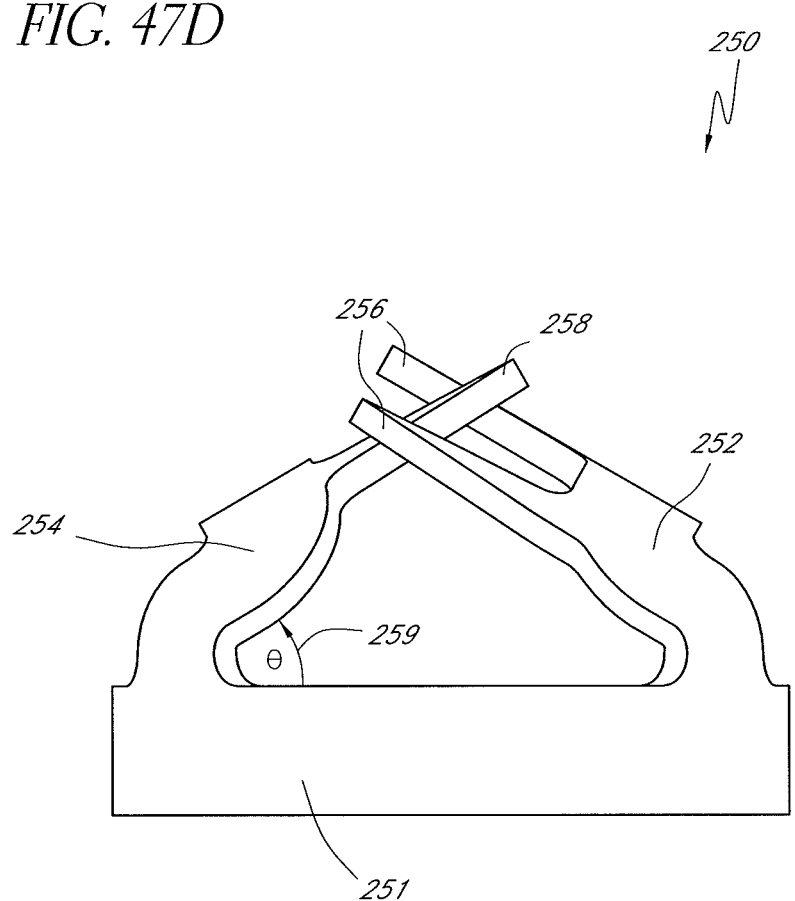
FIG. 47D is a side view of the vascular closure clip of 47A in a closed configuration.

FIGS. 47A-D illustrate another embodiment of a vascular closure clip 250. Clip 250 as illustrated can be similar in many respects to clip 102 except as described below. A primary difference between clip 250 and clip 102 is that the arrangement of fingers 252, 254 on clip 250 is asymmetric: the number of tines 256, 258 on each side is not equal. For example, as illustrated, a first finger 252 can include three tines 256. A second finger 254 can include two tines 258. Tines 256 and tines 258 can be offset from one another and configured to interlace when clip 250 is in a closed configuration as seen in FIG. 47B-D. This interlacing configuration can provide certain advantages over the configuration of clip 102. For example, fingers 252 and 254 can be configured to apply greater compression to tissue and to more completely close the arteriotomy 114, by attempting to draw generally opposing sides of tissue past one another. In addition, the interlaced configuration can in some embodiments, permit a smaller angle θ 259 to be formed between a central axial line or an edge in fingers 252, 254 and a peripheral surface or an edge 253 of a base portion 251 for a given length of fingers 252, 254. In some embodiments, angle θ 259 can be greater than or equal to about 10° and/or less than or equal to about 50°. In a particular example, angle θ 259 can be about 30°. In the illustrated example of FIG. 47C, fingers 252 and 254 do not contact one another when clip 250 is in its closed or deployed configuration. In other embodiments, fingers 252 and 254 can be configured to contact one another in the deployed configuration. For example, tines 258 can be configured to rest on forward surfaces 253 of finger 252. Tines 256 can be configured to rest on forward surfaces 255 of finger 254.

Figure 48A:
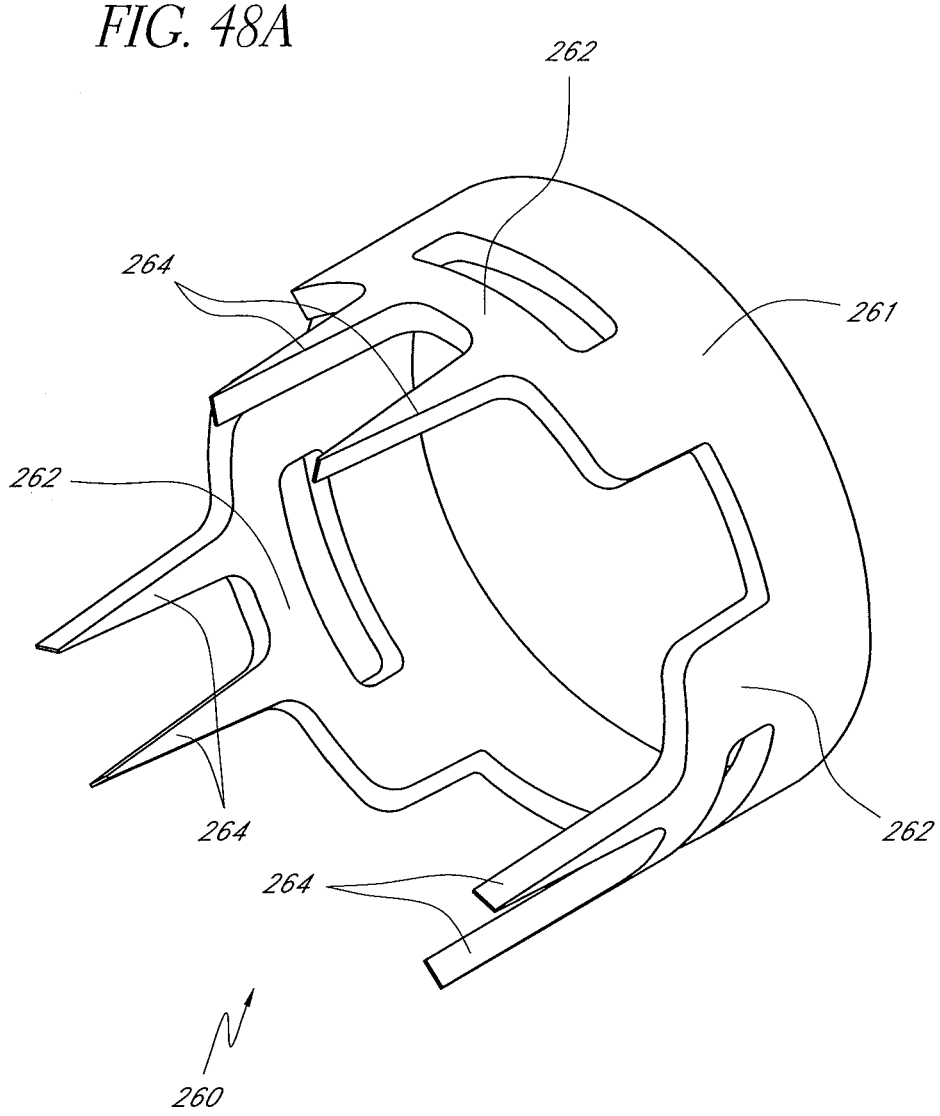
FIG. 48A is a perspective view of another embodiment of a vascular closure clip in a closed configuration.
Figure 48B:
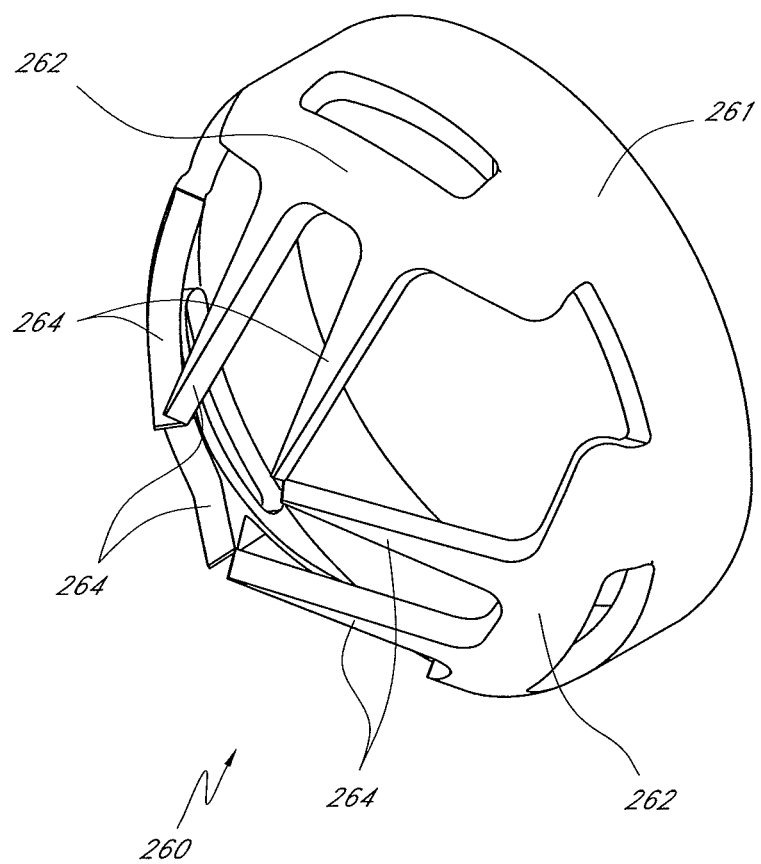
FIG. 48B is a perspective view of the vascular closure clip of FIG. 48A in an open configuration.

FIGS. 48A-B illustrate another embodiment of a vascular closure clip 260. Clip 260 can be similar to other clips disclosed herein, except as described below. Clip 260 includes three symmetrical fingers 262 extending from annular base 261. As illustrated, fingers 262 can be uniformly spaced around the circumference of base 261. Each finger 262 can include two tines 264. Distal ends of tines 264 are configured to meet when clip 260 is in its closed configuration as illustrated in FIG. 48B.

Figure 49A:
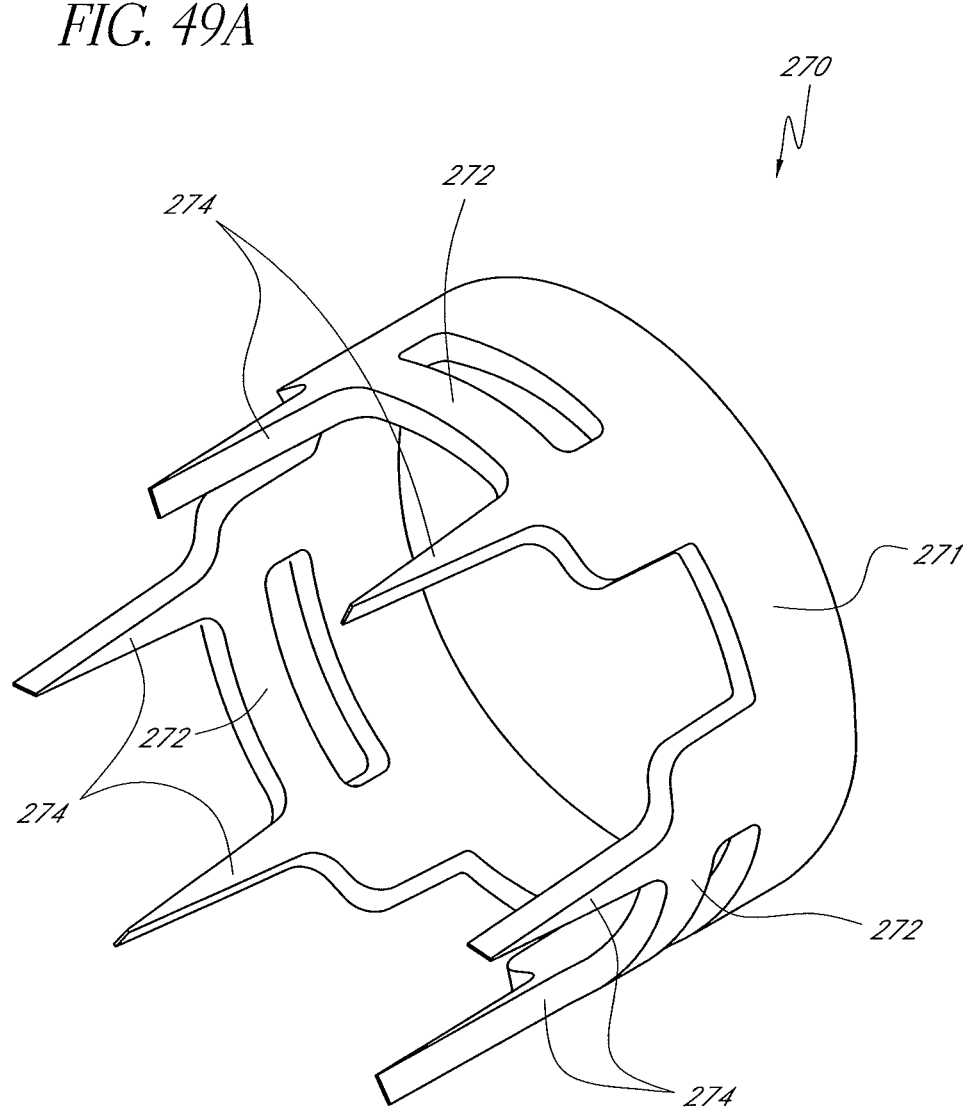
FIG. 49A is a perspective view of another embodiment of a vascular closure clip in an open configuration.
Figure 49B:
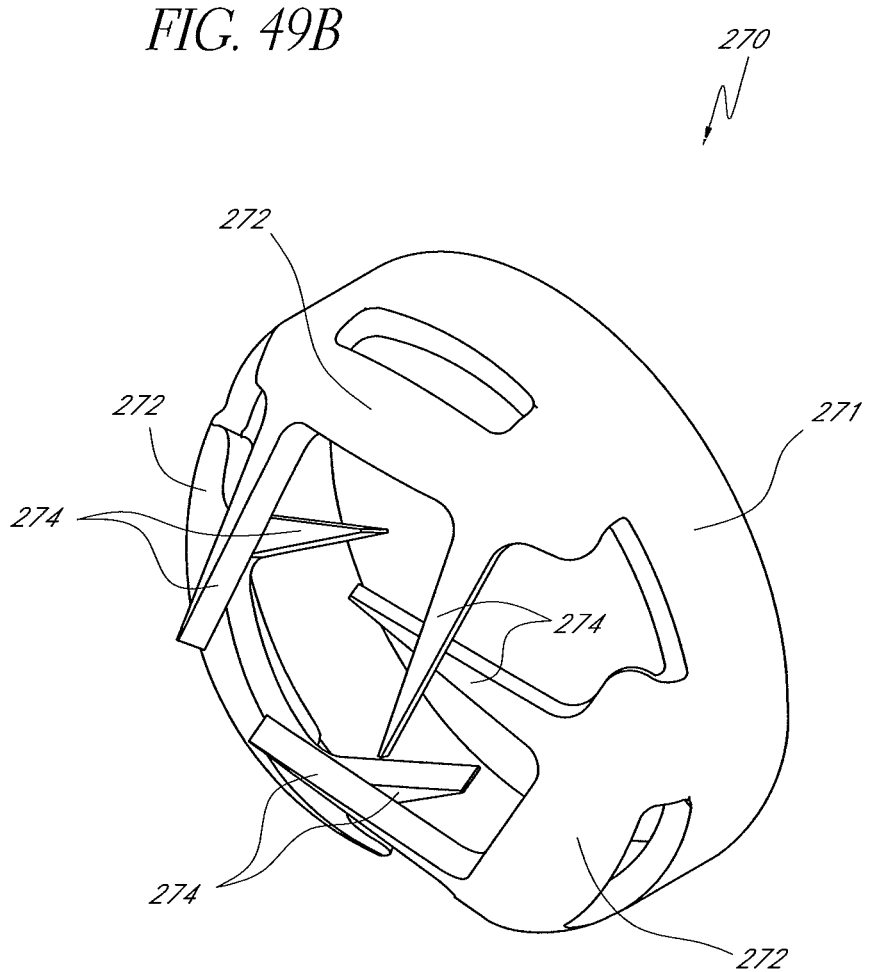
FIG. 49B is a perspective view of the vascular closure clip of FIG. 49A in a closed configuration.

FIGS. 49A-B illustrate another embodiment of a vascular closure clip 270. Clip 270 can be similar in many respects to clip 260 except as described below. Clip 270 can include three symmetrical fingers 272 which can be uniformly spaced around the circumference of annular base 271. A primary difference between clip 270 and clip 260 is that the tines 274 of clip 270 are configured to overlap tines 274 of adjacent fingers when clip 270 is in a closed configuration.

Figure 50A:
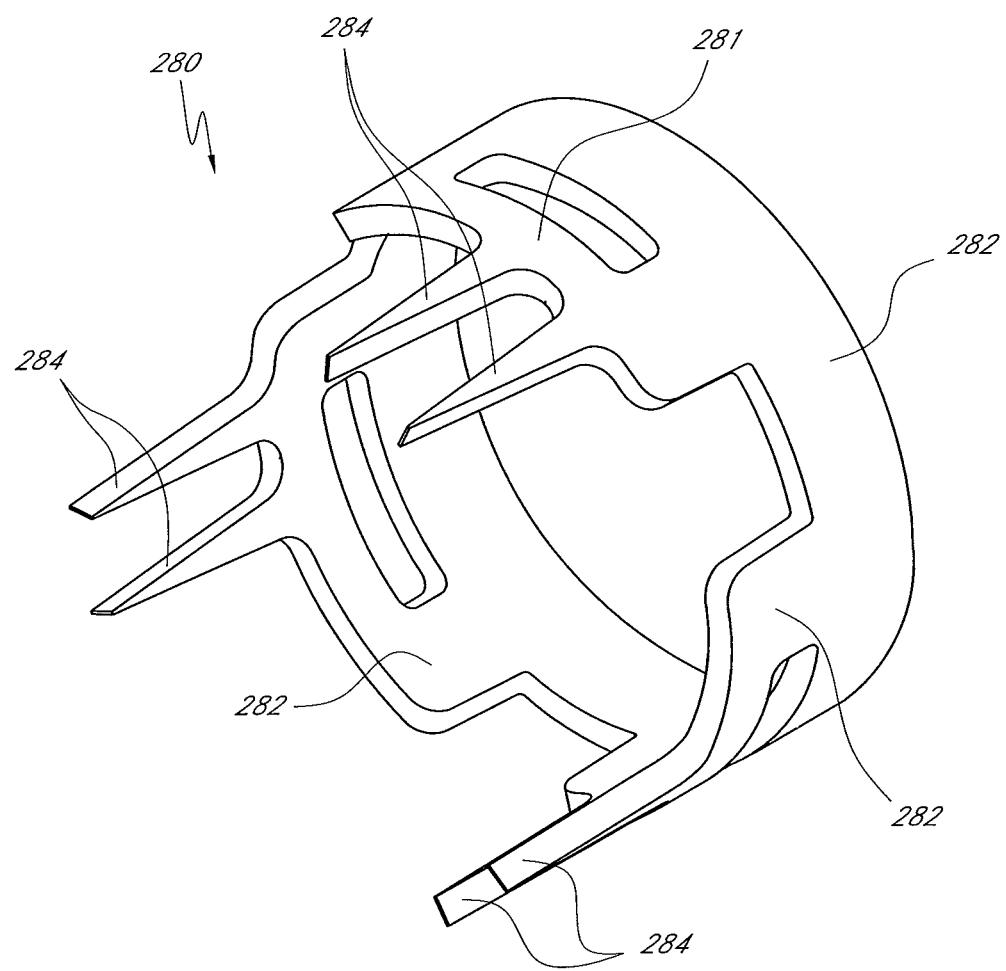
FIG. 50A is a perspective view of another embodiment of a vascular closure clip in an open configuration.
Figure 50B:
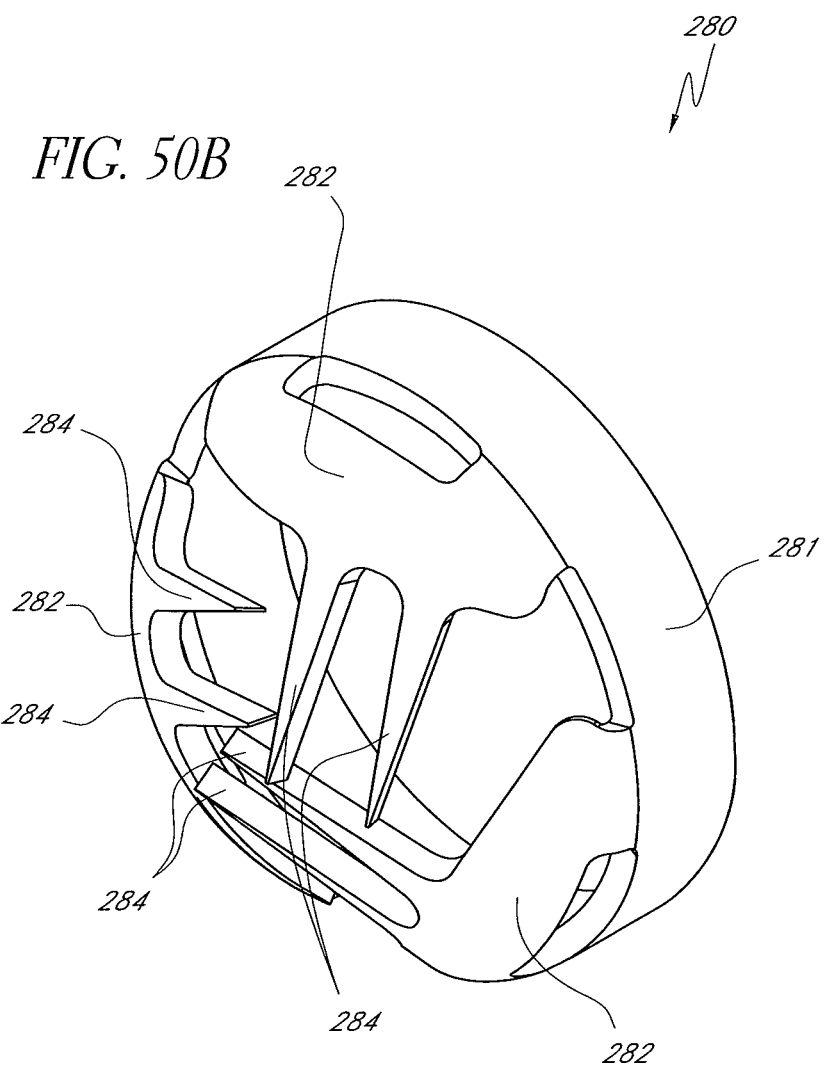
FIG. 50B is a perspective view of the vascular closure clip of FIG. 50A in a closed configuration.
Figure 51A:
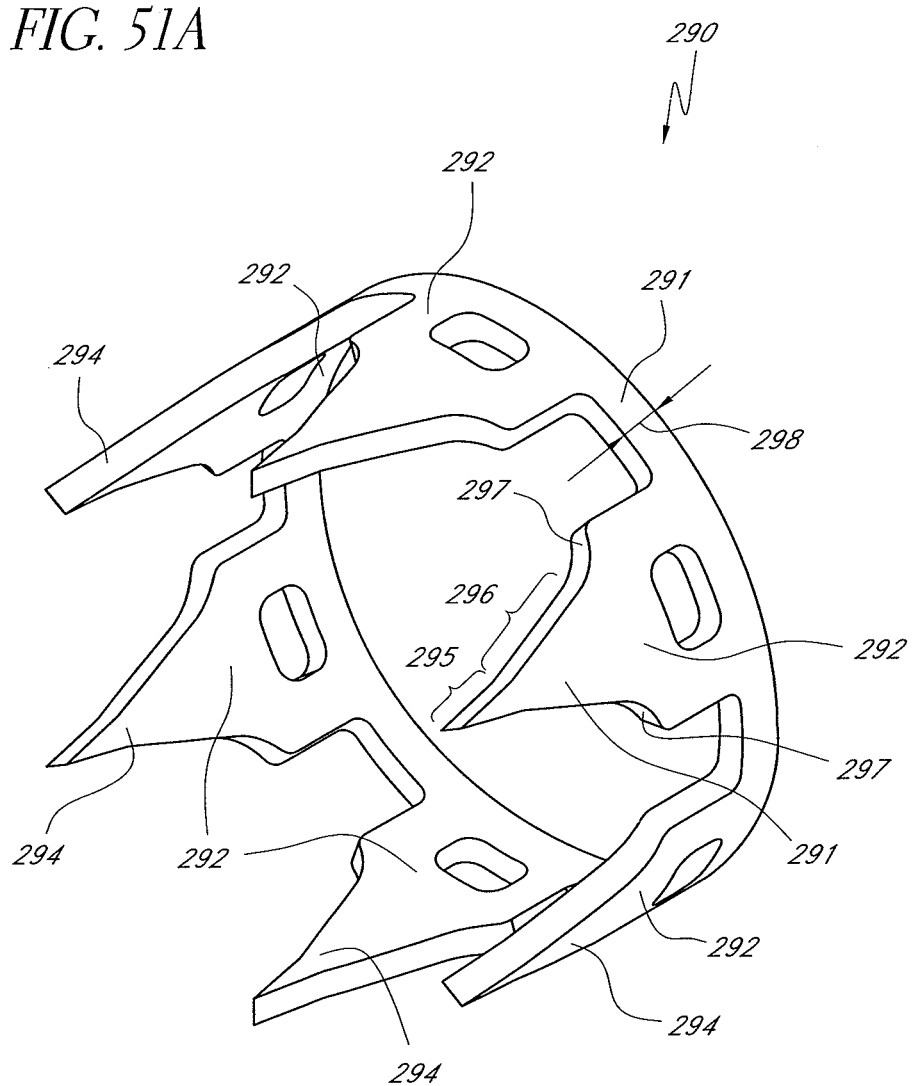
FIG. 51A is a perspective view of another embodiment of a vascular closure clip in an open configuration.
Figure 51B:
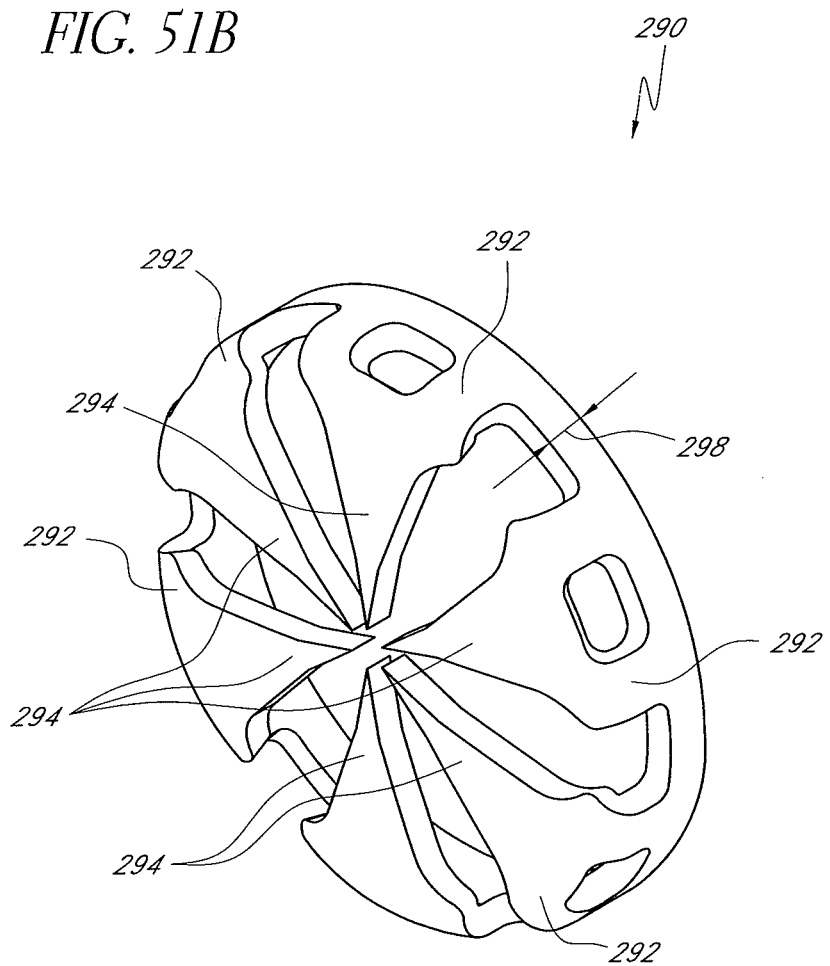
FIG. 51B is a perspective view of the vascular closure clip of FIG. 51A in a closed configuration.
Figure 51C:
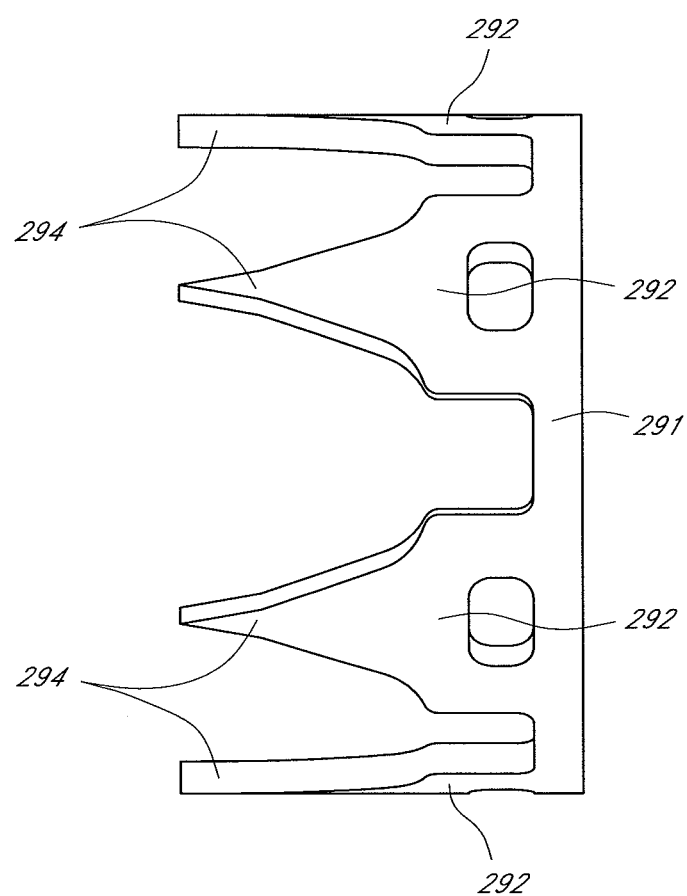
FIG. 51C is a side view of the vascular closure clip of FIG. 51A in an open configuration.
Figure 51D:
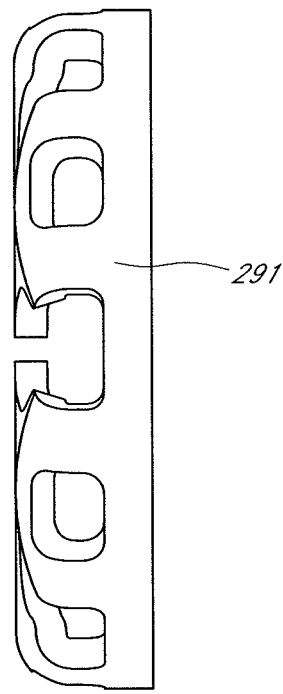
FIG. 51D is a side view of the vascular closure clip of FIG. 51A in a closed configuration.
Figure 51E:
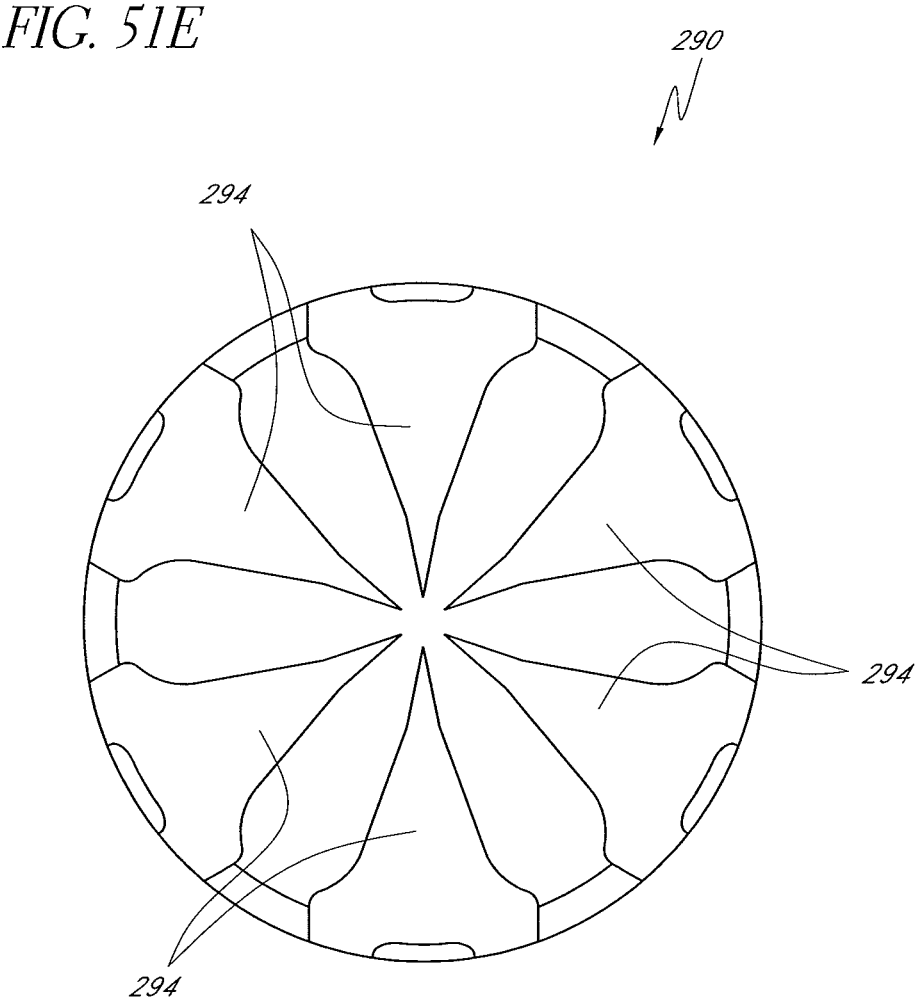
FIG. 51E is a top view of the vascular closure clip of FIG. 51A in a closed configuration.

FIGS. 50A-B illustrate another embodiment of a vascular closure clip 280. Clip 280 can be similar to other clips disclosed herein, except as described below. Clip 280 can include three fingers 284, which can be substantially uniformly spaced around the circumference of annular base 281. Each finger 282 includes two tines 284 which are offset to one side from a central portion of the finger 282. This configuration can permit fingers to bend to a greater degree in the closed configuration without overlapping FIGS. 51A-E illustrate another embodiment of a vascular closure clip 290. Clip 290 can be similar to other clips disclosed herein, except as described below. Clip 290 includes six fingers 292 substantially uniformly spaced around a circumference of base portion 291. In some embodiments, each finger 292 includes only a single tine 294. Tines 294 are configured to fold to a substantially flat configuration, best seen in FIG. 49D. Such a configuration permits clip 299 to have a relatively low interior profile. Tines 294 are not configured to contact one another when clip 290 is in a closed configuration. In other embodiments, tines 294 can be configured to meet at a central point. Tines 294 include a distal-most portion 295 and a second more-proximal portion 296. Portion 295 defines a first interior angle which can be smaller than an interior angle defined by portion 296. Such a configuration gives tines 294 a relatively "sharp" tip and can facilitate the tines' initial penetration of vessel wall 116. Base portion has a height 298. As illustrated height 298 can be relatively small and can be, for example, approximately equal to or less than one fifth of a radius defined by annular base portion 291. A relatively small height 298 permits the clip 290 to have a relatively low external profile when implanted.

Clip 290 can provide more complete circumferential closure by being configured to engage tissue on substantially all sides of arteriotomy. In certain embodiments, it can be more desirable to use such clips 290 for permanent implantation and other clips for temporary implantation. For example, the use of only two opposed fingers can facilitate removal. The use of only two opposed fingers can create a "pinching"-type closing action which can be advantageously simple and predictable.

Figure 52:
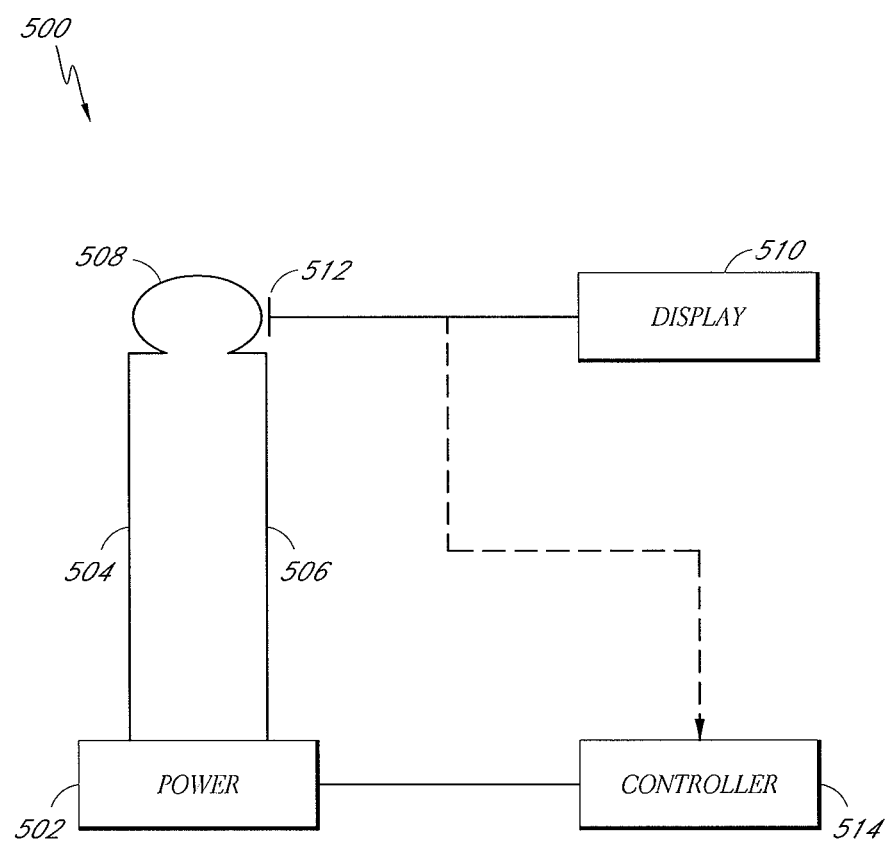
FIG. 52 illustrates a circuit diagram of a circuit utilizing direct resistive element heating to heat tissue surrounding the arteriotomy.

In certain embodiments, heat can be used to facilitate the closure of arteriotomy 114. FIG. 52 illustrates a circuit 500 utilizing direct resistive element heating to heat tissue surrounding the arteriotomy 114. In certain embodiments, selected tissue surrounding the arteriotomy can be heated to a temperature which can be equal to about 40° C., between about 40° C. and 45° C., or greater than about 45° C. At these temperatures, tissue being compressed together by a vascular closure clip may undergo cellular changes tending to fuse tissue together to close the arteriotomy.

Heat can be used with any of the vascular closure clips described above, such as, for example clip 102. A power source 502 such as an RF power source is provided. Other suitable power sources such as a DC power source can also be used. Power source 502 is connected to a resistive element 508 via conductors 504 and 506. Clip 102 can function as the circuit's resistive element 508. In certain embodiments, only a portion of clip 102 will function as the resistive element. Clip 102 can be treated to increase its resistance value by, for example, being covered with a resistive coating. An increased resistance can reduce the power level necessary to effectuate a given amount of heating. In certain embodiments, portions of the clip 102 are covered with a thermally and/or electrically insulative coating. The remaining, uncovered portions of clip 102 can be configured to transfer thermal energy to the tissue being heated. In certain embodiments, only the tines or a distal portion of the tines are configured to transfer the thermal energy to the tissue. Conductors 504 and 506 can include wires made from a suitable electrically-conductive material such as copper-clad steel. In certain embodiments, conductors 504 and 506 can also function as tethering elements to allow removal of clip 102. Conductors 504 and 506 can be covered with an insulating cover or coating. A thermocouple 512 can be mounted to the clip to monitor the temperature of the clip and/or the surrounding tissue. The recorded temperature can be provided to a user display 510 and/or controller 514. Controller 514 permits the medical professional to adjust the amount of power delivered to the resistive element 508. In certain embodiments, the power delivered can be less than about 2 W, between about 2 and about 50 W, or greater than 50 W. The medical professional can maintain the tissue at the desired temperature for a certain length of time. In some embodiments, heat can be applied to the tissue for a period less than or equal to about 30 seconds, or greater than 30 seconds.

Following the application of heat, the conductors 504, 506 can be disconnected from clip 102 in many ways. For example, a twisting, cutting, or other manipulative action can be used to remove the conductors. In embodiments utilizing temporary or removable clips, conductors 504, 506 can be used as a primary or backup tethering element to remove the clip 102 following hemostasis. In certain embodiments, conductors 504, 506 can be connected to the clip 102 via spot welding, mechanical fit, soldering, combination, or other suitable method. Conductors 504, 506 can be fabricated from many different materials, such as copper, platinum, stainless steel, or a composite of materials (e.g. copper clad steel or platinum and silver combined by a drawn filled tubing process). In certain embodiments, conductors 504, 506 can include composite signal wires using silver as the inner core to better transmit, for example, radiofrequency or direct current energy. Conductors 504, 506 can be fabricated with a circular, elliptical, rectangular (flat), or other geometry which may depend on the space available on the clip 102. Conductors 504, 506 can be covered or jacketed with an insulative material such as polyimide, polyamide, polyurethane, polyester, nylon, or other suitable material.

In certain embodiments, a special tip can be placed over a standard electrosurgical tool such as, for example, a Bovie, to insert through the skin and make contact with the closure device and/or tissue. In certain embodiments, alternative heating means can be provided to heat the clip and/or the adjacent tissues including, for example, ultrasound energy, microwave energy, etc.

Figure 53:
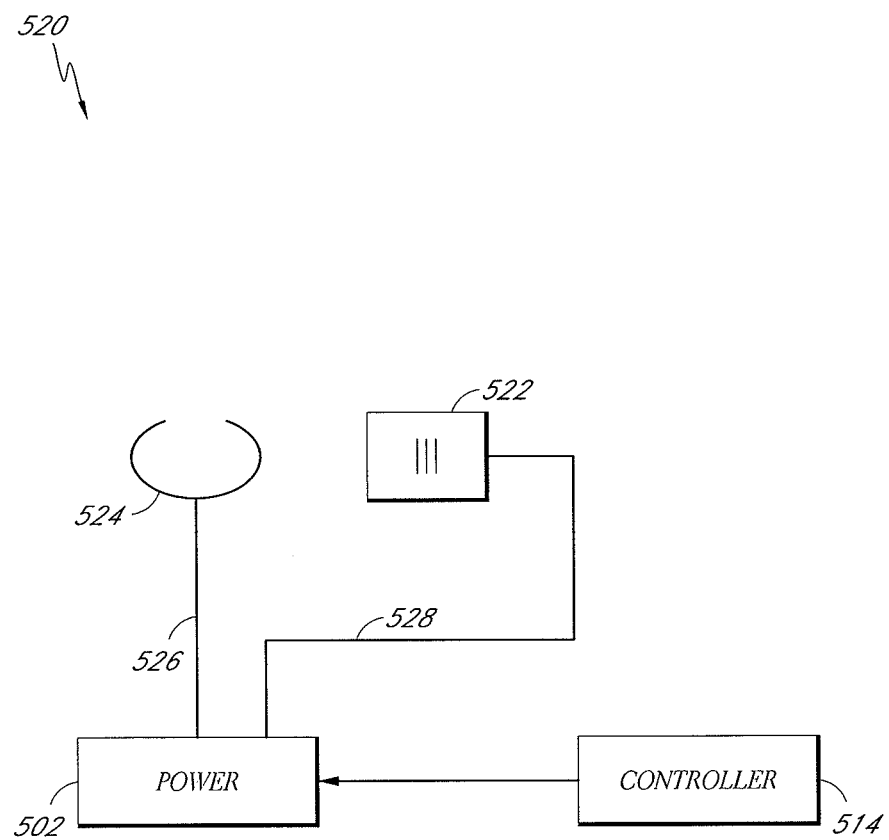
FIG. 53 illustrates a circuit diagram of a circuit utilizing ohmic tissue heating to heat tissue surrounding the arteriotomy.

FIG. 53 illustrates a circuit utilizing ohmic tissue heating to heat tissue. A power source 502 such as an RF or DC power source is provided. Power source 502 is connected to an active electrode 524 via conductor 526. Clip 102 can function as the active electrode 524. Alternatively, only a portion of clip 102 can function as the active electrode 524. For example, in certain embodiments, one or more of the clip's tines or only a portion of the clip's tines such as the distal-most portion can function as the active electrode 524. In certain embodiments, remaining portions of the clip 524 are covered with an electrically insulating cover or coating. A second conductor 528 connects power source 502 to an indifferent electrode 522. Indifferent electrode 522 can be, for example, an electrode plate or large surface area indifferent ground pad applied to the patient's skin. Indifferent electrode 522 can be placed on the patient's back, thigh or other location. Indifferent electrode 522 can be applied to a portion of the patient's skin generally opposite the percutaneous opening. The power supply 502 applies a voltage differential across the active and indifferent electrodes 524, 522 causing current to flow through the intervening tissue thus heating the tissue. The heat is generally concentrated at tissue adjacent to the active electrode 524. Controller 514 can permit the medical professional to adjust the amount of power delivered.

In another embodiment (not shown), a first portion of the clip can act as a first electrode and a second portion of the clip can act as a second electrode. The first and second portions of the clip can be electrically insulated from one another. For example, a first finger or a portion of the first finger such as one or more tines can act as the first electrode and a second finger or a portion of the second finger can act as the second electrode. A power source applies a voltage differential across the first and second electrodes causing current to flow between them and heat intervening tissue.

An electrode-enabled closure device can also be used to confirm contact between the closure device and the tissue surface, such as by comparing the impedance between an electrode element and a return path (indifferent electrode or second electrode). When an electrode surface contacts only or primarily blood, the measured impedance can be substantially higher than when a small or substantial portion of the electrode surface contacts tissue.

Figure 54:
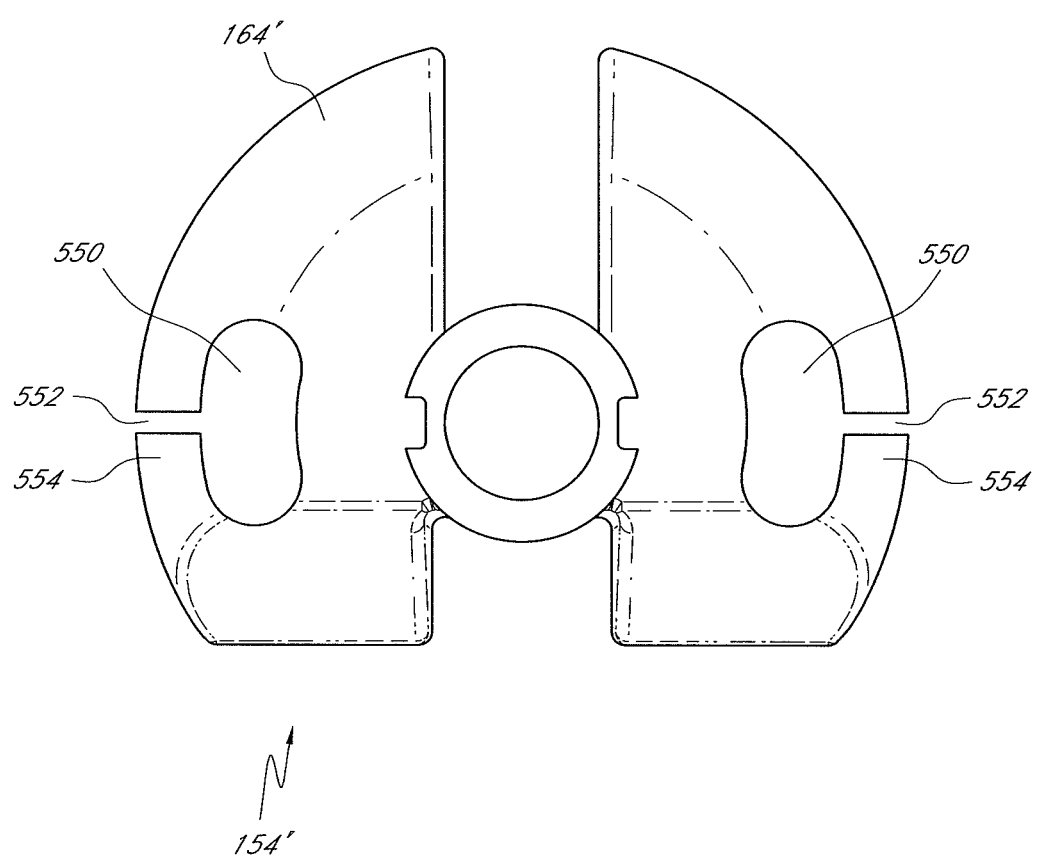
FIG. 54 is a distal end view of another embodiment of an inner tube that can form one component of a deployment instrument.
Figure 55:
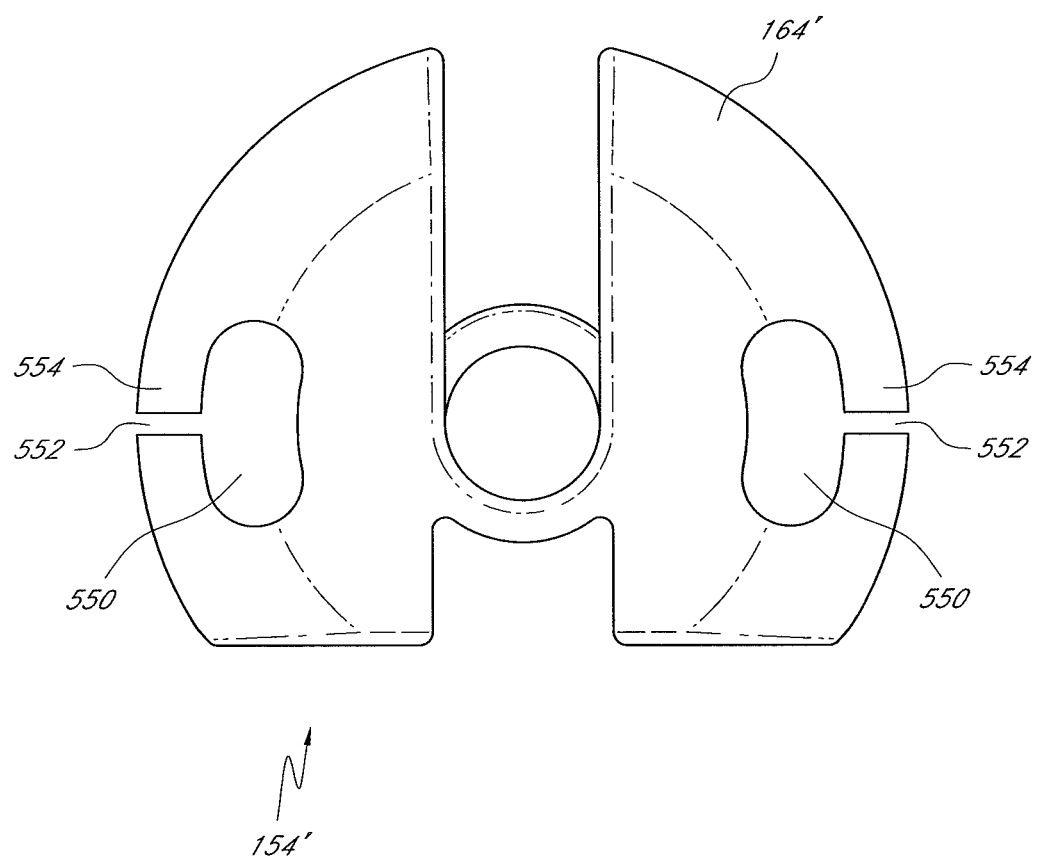
FIG. 55 is a proximal end view of the inner tube of FIG. 54.

FIG. 54-55 show another embodiment of an inner tube 154' which can form one component of a deployment instrument.

Inner tube 154' can be similar to inner tube 154 described above. A primary difference between inner tube 154' and inner tube 154 is the inclusion of recessed portions 550 on handle 164'. Connecting channels 552 can be relatively thin and can permit access from an exterior surface of handle 164 to an interior of recessed portions 550. Recessed portions 550 can receive the proximal ends of suture lines 234. For example, the proximal ends of suture lines 234 can be tied to or looped around portions 554 of handle 164'. A removable clip can be implanted using the procedure described above. Prior to removal of the deployment instrument, the suture lines 234 can be removed from portions 554 of handle 164'. Following hemostasis, the proximal ends of the suture lines 234 can be grasped to withdraw the clip from the vessel and out of the patient.

Other clip variations are also possible. The tissue compression can be modified by adjusting one or more of several tissue engagement element design attributes, such as the length, width, thickness, angle, number and location of the elements, etc. The proximal edge of the clip can have a straight, sinusoidal, notched, keyed, combination or other suitable design. The proximal edge geometry can mate with a contacting surface of the advancement and deployment instrument. Clips can be made from one or more of a tubing, sheet, wire, strip, band, rod, combination or other suitable material.

In certain embodiments, the clip can be configured to be in its malleable martensite phase at room temperature. The clip can be loaded onto a deployment instrument in an open configuration. The clip can be configured to transition to an austenite phase by the application of heat during or after deployment. The application of heat can cause the clip to revert to its memorized, closed configuration. In certain embodiments, the clip can be configured to revert to its closed configuration upon being heated to a temperature near the temperature of the human body. In such embodiments, the clip can be delivered to the arteriotomy and partially deployed or held in place on the exterior of the vessel wall 116 for a period of time sufficient to heat the clip to its austenite transition temperature. In other embodiments, heat may be applied via insertion of a heated probe or remotely via application of focused electromagnetic energy.

The clip can include at least one (single element) hinge feature to assist with deployment, tissue engagement, compression and or removal from the tissue. The clip can be partially or completely made from one or more of the following materials: metals including, spring steel and stainless steel, metal alloys including nitinol, 17-7 PH, Elgiloy, and Inconel. Other appropriate materials can also be used. In a preferred embodiment, the clip can be partially or completely made from a superelastic and/or shape memory material such as nitinol. A discussion of certain properties of superelastic and/or shape memory materials can be found in U.S. Pat. No. 7,182,771, the entirety of which is hereby incorporated by reference herein and made a part of the present specification. In certain embodiments, such as those utilizing nitinol or other superelastic and/or shape memory materials, it can be desirable for the clip to have a relatively tight bend in a memorized configuration. In some circumstances, it can be advantageous to use a bend sufficiently tight that it would normally exceed the elastic limit of the material and thus permanently deform it. To prevent permanent deformation, a bend can be produced in the device followed by an annealing process to relieve bending stresses within the device. Following this first bend, the device can be bent further to produce an even sharper bend, and then re-annealed to alleviate the stress from this additional bending. This process can be repeated to attain a desired substantial bend, or reduced radii, or reduced angle that would otherwise permanently deform the device if the bend were attempted in a single bending event. In certain embodiments, any surface of the clip that comes in contact with blood and/or tissue can be electropolished, especially metal or metal alloy surfaces, such as a superelastic/shape memory alloy. Electropolishing may be used to produce smooth surfaces. Electropolishing can also beneficially remove or reduces flash and other artifacts from the fabrication of the device.

The clip can have a completely contiguous cross section, or partial, incomplete contiguous cross section. A discontiguous cross-section can permit certain embodiments of the clips to be loaded from the side of the vascular introducer and/or deployment instrument. In certain embodiments, the deployment instrument can include a slot or opening permitting the deployment instrument to be secured to the tubular medical device from the side. Tissue engagement elements (e.g., tines, fingers, protrusions, etc.) can be parallel, overlapping, crossing, spiral, combination or other. The clip can include tissue engagement elements with the same, different or combination lengths. The clip can compress tissue on a horizontal plane, vertical plane or a combination of both. The tissue engagement elements can be straight, curved or a combination of both. The tissue attachment motion/direction can be straight, twisted, rotated, combination or other suitable and desirable motion or motions.

Figure 56A:
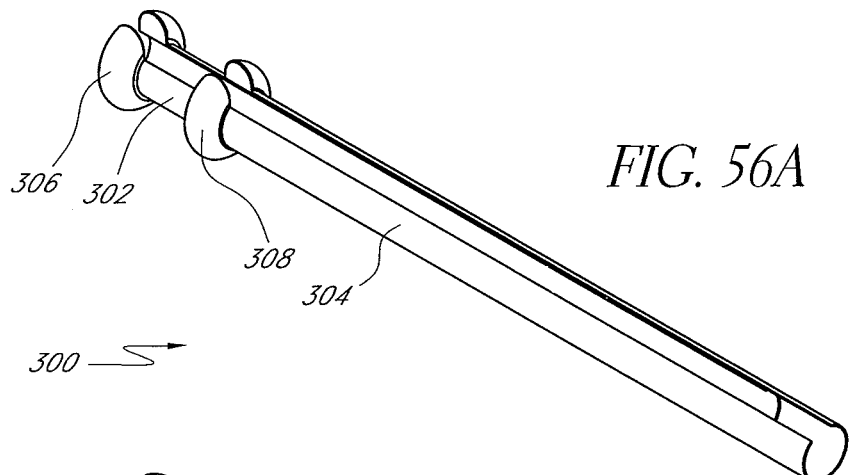
FIG. 56A is a perspective view another embodiment of a deployment instrument which can be used with a vascular closure plug.
Figure 56B:
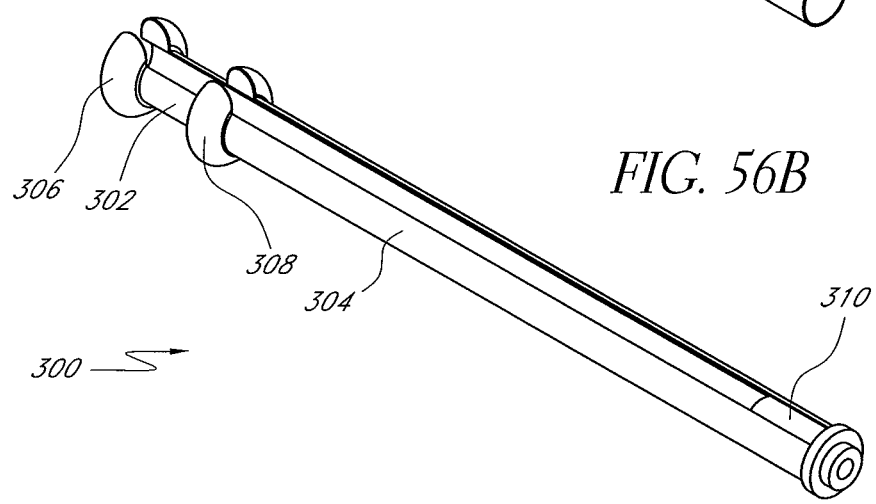
FIG. 56B is a perspective view of the deployment instrument of FIG. 56A preloaded with a vascular closure plug.
Figure 56C:
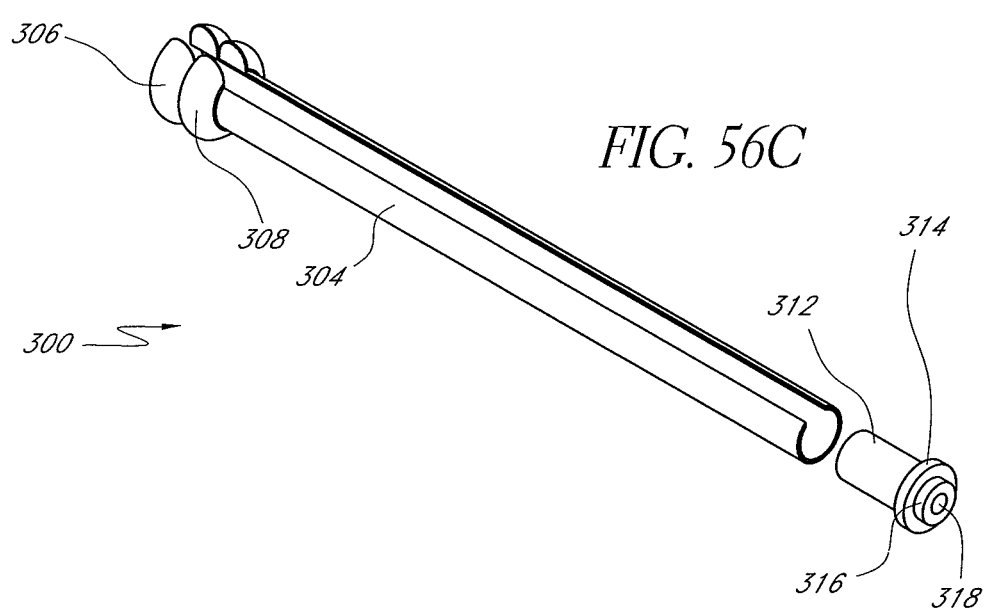
FIG. 56C is a perspective view of the deployment instrument of FIG. 56A after deploying the vascular closure plug.

FIGS. 56A-C illustrate an additional embodiment of a vessel closure system. A swellable plug 310 which can be bioabsorbable is loaded onto the distal end of a plug deployment instrument 300. Plug deployment instrument 300 can include an inner tube 302 with handle 306 and an outer tube 304 with handle 308. The proximal end 312 of plug 310 can be received by the distal end of outer tube 304. Intermediate stop portion 314 of plug 310 can have a larger outer diameter than either proximal end 312 or distal end 316 and is received against the distal end of the outer tube 304. As illustrated, stop portion 314 can have a generally circular geometry. However, other suitable shapes or geometries can be used. For example, in certain embodiments stop portion 314 can have a flared or tapered shape, a general 'X' shape, an inverted general 'T' shape, a combination or any other suitable shape or geometry. In certain embodiments, stop portion 314 can be slotted or ribbed to facilitate flexing during advancement. Proximal end 312 can be relatively long to facilitate plug kinking as will be described below. In certain embodiments, proximal end 312 can have a length that is greater than or equal to about twice the length of distal end 316, and/or greater than or equal to about five times the length of distal end 316. Plug 310 can include a longitudinal channel 318 allowing the deployment instrument 300 and plug 310 to be advanced over a tubular medical device in a similar fashion to that described above with respect to deployment instrument 104. Inner tube 306 can be advanced distally by applying pressure to handle 306 and/or by pulling handle 308 in a proximal direction. A stop means such as a removable element affixed to the outer tube 302 between handles 306 and 308 can maintain separation of handles 306 and 308 until the medical professional is ready to begin deployment. Once the medical professional has confirmed proper placement of the distal end of the deployment instrument 300, the stop means can be overcome by for example removing the removable element in order to begin deployment. The distal end of inner tube 306 pushes plug 310 free of the outer tube 304 to effect deployment. The deployment instrument 300 can be configured such that the plug 310 will be fully deployed when the handles 306 and 308 have been brought together.

Swellable plug 310 can be partially or completely fabricated from materials that swell, or expand when they are exposed to a fluid, such as blood or subcutaneous fluid, or another fluid, for example, that can be added by the physician to cause the material to swell. These materials include hydrophilic gels (hydro gels), regenerated cellulose, polyethylene vinyl acetate (PEVA), as well as composites and combinations thereof and combinations of other biocompatible swellable or expandable materials. Thus, upon deployment, swellable plug 310 can swell causing longitudinal channel 318 to be occluded and sealing the arteriotomy. In certain embodiments, plug 310 can be partially or completely fabricated from a lyophilized hydrogel, such as, for example polyethylene gycol (PEG) or other polymer carrier. The polymer used in the carrier can include hydrolytically degradable chemical groups, thereby permitting in vivo degradation. Hydrophilic polymeric materials suitable for use in forming hydrogels include poly(hydroxyalkyl methacrylate), poly(electrolyte complexes), poly(vinylacetate) cross-linked with hydrolysable bonds, water-swellable N-vinyl lactams polyscaccharides, natural gum, agar, agarose, sodium alginate, carrageenan, fucoidan, furcellaran, laminaran, hypnea, eucheuma, gum Arabic, gum ghatti, gum karaya, gum tragacanth, locust beam gum, arabinogalactan, pectin, amylopectin, gelatin, hydrophilic colloids such as carboxymethyl cellulose gum or alginate gum crosslinked with a polyol such as propylene glycol, and the like. Several formulations of previously known hydrogels are described in U.S. Pat. No. 3,640,741 to Etes, U.S. Pat. No. 3,865,108 to Hartop, U.S. Pat. No. 3,992,562 to Denzinger et al., U.S. Pat. No. 4,002,172 to Manning et al., U.S. Pat. No. 4,014,335 to Arnold, U.S. Pat. No. 4,207,893 to Michaels, and in Handbook of Common Polymers, (Scott and Roff, Eds.) Chemical Rubber Company, Cleveland, Ohio, all of which disclosures in the foregoing patents and publication regarding hydrogels are incorporated herein by reference.

Figure 57:
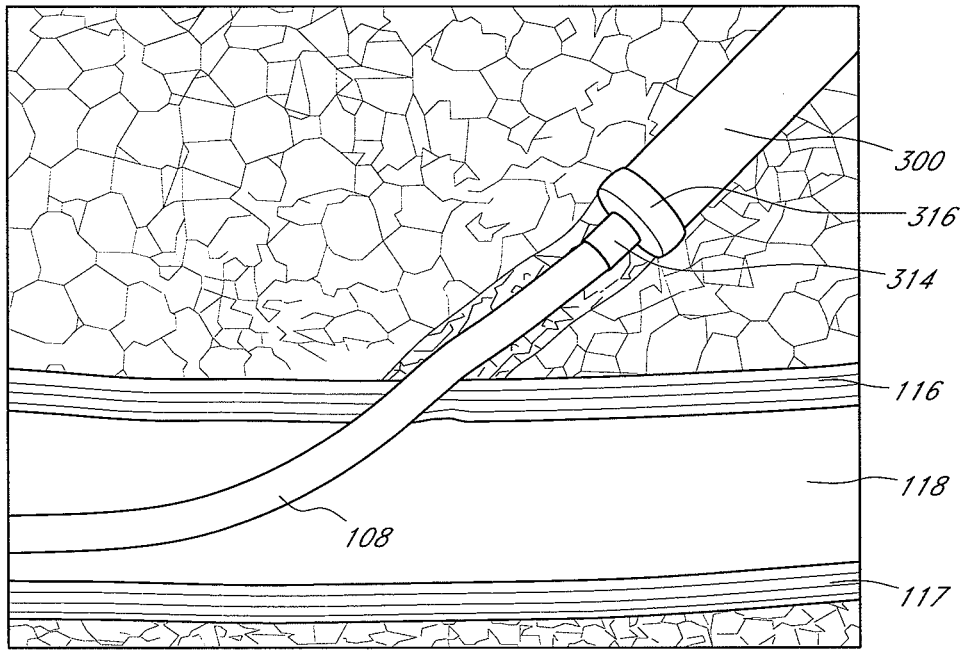
FIG. 57 is a side view of the deployment instrument of FIG. 56B being advanced over a vascular introducer that has been inserted into a patient's blood vessel.
Figure 58:
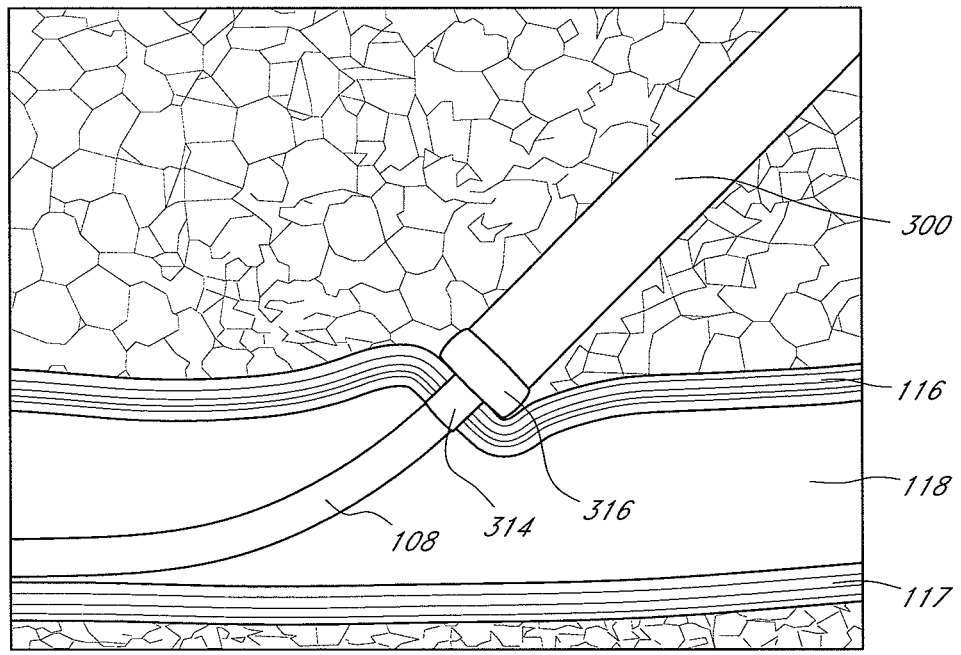
FIG. 58 is a side view of the deployment instrument of FIG. 57 positioning the distal end of the vascular closure plug against the arteriotomy.
Figure 59:
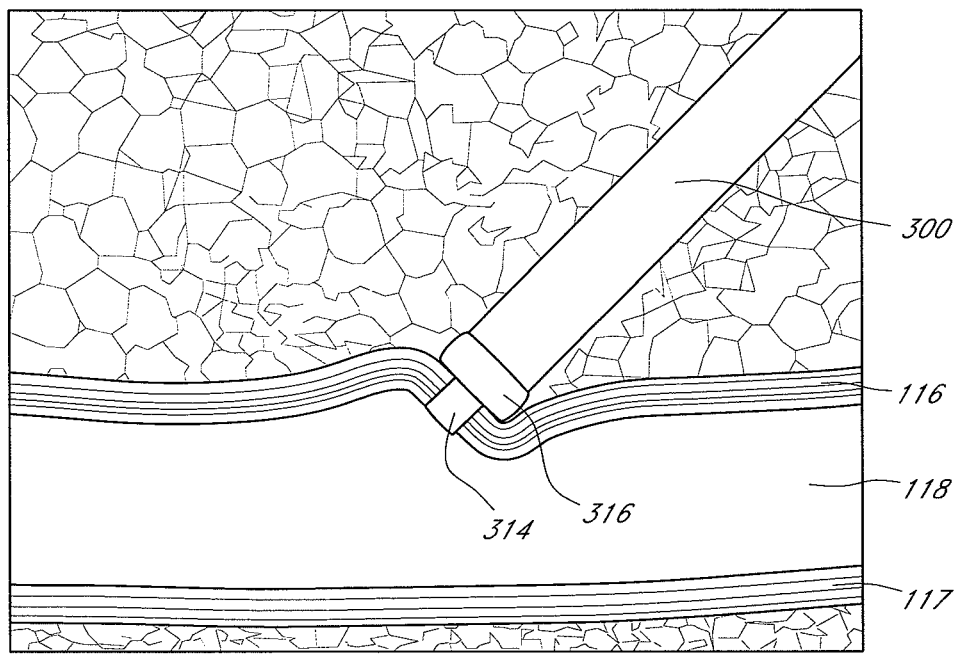
FIG. 59 is a side view of the deployment instrument of FIG. 57 holding the plug against the arteriotomy after removing the vascular introducer.

An example of a method for using plug deployment instrument 300 and plug 310 will now be described with reference to FIGS. 57-63. The deployment instrument 300 loaded with plug 310 can be advanced over a previously installed tubular medical device 108 as shown in FIG. 57 until the distal end 316 encounters vessel wall 116. In certain embodiments, as illustrated, distal end 316 can be received within the arteriotomy 114. In other embodiments, distal end 316 can be received against an outer surface of vessel wall 316. Intermediate portion 314 can be configured to act as a stop to prevent overinsertion of plug 310 into the vessel. The introducer sheath can then be removed from the vessel as shown in FIG. 59.

Figure 60:
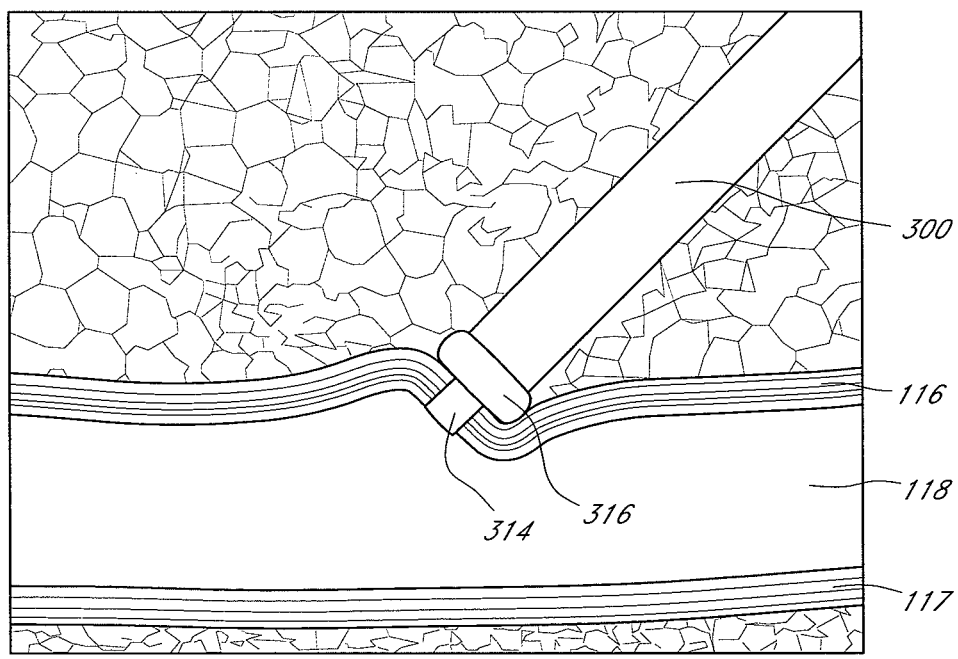
FIG. 60 is a side view of the deployment instrument of FIG. 57 showing the exposed portions of the plug beginning to swell.
Figure 61:
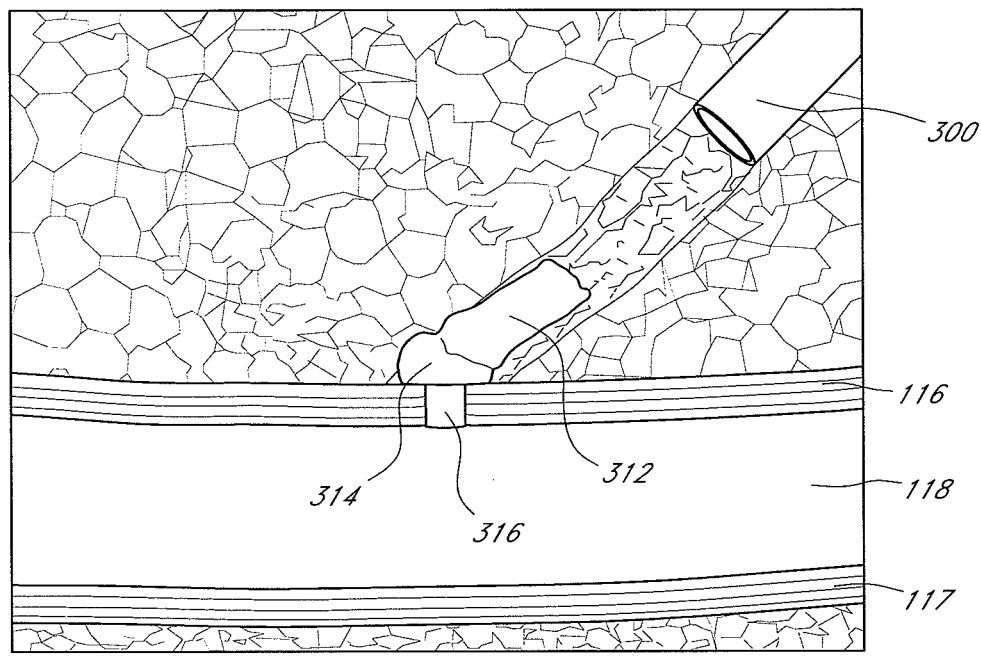
FIG. 61 is a side view of a deployed plug as the deployment instrument of FIG. 57 is removed.
Figure 62:
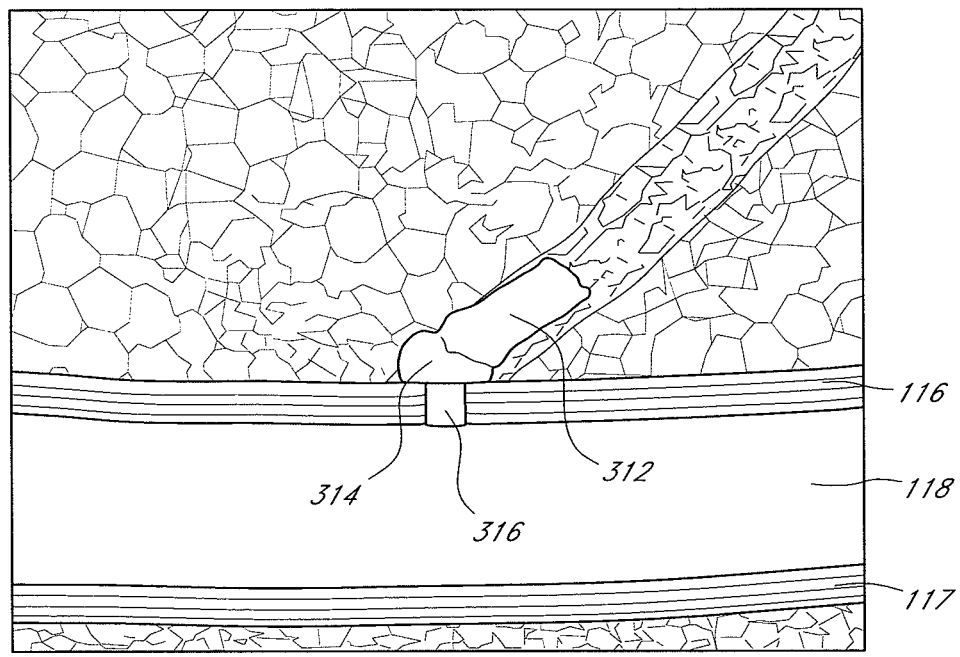
FIG. 62 is a side view of the deployed plug of FIG. 61 which is continuing to swell.
Figure 63:
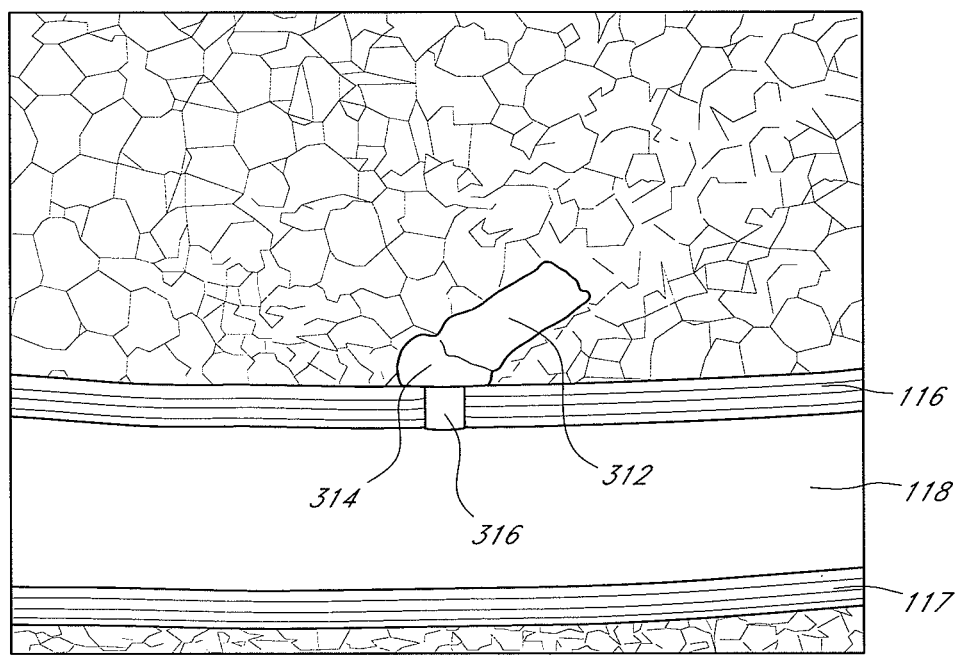
FIG. 63 is a side view of the deployed plug of FIG. 61 which has begun to be absorbed by the patient's body.

As shown in FIG. 60, the deployment instrument 300 can be held in place against the vessel wall 316 while the exposed portions of plug 310 begin to swell. The swelling can be initiated or accelerated by various events, such as coming into contact with blood and/or subcutaneous fluid. In certain embodiments, the enlargement of distal end 316 can help to secure the plug 310 in place within the arteriotomy 114. The swelling of plug 310 can occlude longitudinal channel 318, tending to seal or otherwise partially or entirely fill the arteriotomy 114. Alternatively or additionally, the channel 318 can be occluded via kinking of proximal portion 312. Once the plug 310 is secured to the vessel wall 116, deployment instrument 300 can be removed as shown in FIG. 61. Fatty tissue that was previously displaced by the deployment instrument 300 may begin to fill in the tissue tract. This tissue can thus apply pressure to proximal portion 312 tending to kink or occlude it. Patient movement and/or externally or internally applied pressure can also be used to cause the proximal portion 312 to kink. Deployment of plug 310 at an acute angle to the vessel wall, as illustrated, can also increase the tendency of proximal portion 312 to kink. In certain embodiments, the inner surface of the longitudinal channel 318 can be configured to stick to itself when one region of it contacts another region. For example, in certain embodiments inner surfaces of longitudinal channel 318 can be coated with an adhesive or other appropriate coating to assist in occluding the longitudinal channel 318. In certain embodiments, the adhesive or coating can be configured to avoid or to diminish adherence to the deployment instrument 300. FIG. 62 shows an embodiment of the deployed plug 310 in a fully swollen state. Plug 310 can be completely or partially bioabsorbable. In certain embodiments, plug 310 can be configured to be completely absorbed by the patient's body after about 4 weeks. FIG. 63 shows the plug 310 in a partially-dissolved state.

Swellable plug 310 can be shielded from unintended contact with fluid (blood, saline, etc.), before insertion into the body, by a removable wrapper or dissolvable coating. Swellable plug 310 can include a relatively rigid outer coating that begins to dissolve upon exposure to fluids such as blood, thus providing time for the medical professional to position the plug 310 within the arteriotomy. In some embodiments, a plug can be configured to be advanced directly over the tubular medical device 108 and deployment instrument 310 can be replaced with a pusher instrument. In certain embodiments, a plug can include a longitudinal slit or spiral allowing the plug to be attached to the tubular medical device or deployment instrument from the side. In certain embodiments, the deployment instrument can also include a slot allowing attachment from the side.

The vascular closure device can incorporate one or more coatings, materials, compounds, substances, drugs, therapeutic agents, etc. that positively affect healing at the site, at and or near where the device is deployed, either incorporated into the structure forming the device, incorporated into a coating, or both. Thromboresistance materials, antiproliferative materials, or other coatings intended to prevent thrombosis (acute and or chronic), hyperplasia, platelet aggregation, or other negative response, at or near the attachment of the device within the body. The coatings, materials, compounds, substances, drugs, therapeutic agents, etc. can be used by themselves, and/or contained in a carrier such as a polymeric matrix, starch, or other suitable material or method. The coatings can be liquid, gel, film, uncured, partially cured, cured, combination or other suitable form.

Many different types of delivery features, such as coatings on the vascular closure device, can be used to deliver therapeutic agents, including (but are not limited to) one or more of the following: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) II.sub.b/III.sub.a inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6.alpha.-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof, cell cycle inhibitors, mTOR inhibitors, and/or growth factor signal transduction kinase inhibitors. Alternatively, a clot promoter can be used, such as protamine sulphate or calcium hydroxide. Endothelial cells can also be added to the vascular closure device.

One or more of the therapeutic agents can be included in the device in many ways, such as by blending them into the device base materials during fabrication, applying them just prior to deployment, or applying them after the device has been deployed. One or more therapeutic agents can be used on a single device. The delivery feature can be designed to provide benefits rapidly or over an extended period of time. The delivery feature can be stable or eluting. The coatings, materials, compounds, substances, therapeutic agents, etc. can elute from a coated (or embedded) device (or component) over time and enter the surrounding tissue. In certain embodiments, the delivery feature can be effective during a period of at least about three days in some applications, between about seven and about thirty days in other application, and/or up to approximately six months in some applications.

Post device fabrication coating methods can include, but are not limited to, spin coating, RF-plasma polymerization, dipping, spraying, brushing, submerging the devices into a beaker containing a therapeutic solution while inside a vacuum chamber to permeate the device material, etc.

Alternatively, or in combination with the above therapeutic substances, one or more materials such as platinum, gold, tantalum, tin, tin-indium, zirconium, zirconium alloy, zirconium oxide, zirconium nitrate, phosphatidyl-choline, pyrolytic carbon, combination or other material, can be deposited onto the closure device surface using electroplating, sputtering vacuum evaporation, ion assisted beam deposition, vapor deposition, silver doping, boronation techniques, or other coating process.

Radiopaque material such as barium sulfate, bismuth trioxide, tantalum, platinum/iridium or other suitable materials can be added to any of the closure devices for enhanced visualization under a fluoroscope or other visualization means commonly used in a catheterization lab or surgical suite. Additionally, such materials can be added to the closure device by sputter coating, ion deposition, vapor deposition, combination, or other suitable processes.

In certain embodiments, the distal end of inner tube can have at least one section with a larger circumferential diameter or flare to cause clip tines to deflect outward (during forward movement during deployment), capturing more tissue (than without the increased diameter section) as the clip is advanced forward, for greater tissue compression and sealing. The distal end of the inner tube can also have a non circumferential enlargement such as at least one bump or raised surface arranged around the circumference. This design can be used to cause only some of the clip tines to be opened or deflected outward during advancement and deployment, or some to deflect more than others.

In certain embodiments, the deployment instrument can be configured so that the clip is deployed by advancing the outer tube distally relative to the inner tube instead of by proximally withdrawing the inner tube. The pressure element or other pressure sensing means can be secured to the inner tube, such as for example at a proximal end of the inner tube.

In certain embodiments, suction can be used to temporarily attach the deployment instrument to the vessel wall, and/or to confirm contact with the desired tissue. The deployment instrument can be configured to enable local and/or remote suction. In certain embodiments, an elongate suction tube or lumen can be secured to and/or located within the deployment instrument. The suction tube can include an opening on or near the distal end of the deployment instrument, and a valve or fitting (such as, for example, a Luer fitting) on the side or proximal end of the tool, to which a syringe, bulb, or other suction device could be attached and/or integrally formed. In certain embodiments, local suction can be accomplished without attachment to an external vacuum source. Local suction can be accomplished, for example, using a syringe or other physician manipulated device to pull a vacuum, creating the desired suction. A Luer-lock or stopcock then can be used to close the suction tube or lumen containing the vacuum to maintain a suction condition. In certain embodiments, a remote vacuum suction system can be attached to a vacuum line. The vacuum system can include a means for limiting the amount of vacuum/suction which can be created in order to prevent trauma to the tissue adjacent to the distal suction port.

The slidable tissue cutter can be adapted to use heat to cut skin and or other tissue by making the leading edge an electrode and attaching at least one electrical conductor to the electrode. Direct resistive element heating or ohmic tissue heating can be utilized. Biocompatible materials (e.g., gold, platinum, platinum/iridium, stainless steel, nitinol and other suitable materials) can be used for the electrode and connected to a suitable (e.g., electrical and biocompatible) conductor. For ohmic tissue heating, one conductor can be connected to an RF power source. Another conductor is connected to a ground pad placed on the patient's body, and also connected to the power source. For direct resistive element heating, both conductors from the power source are connected to an electrode.

In certain embodiments, the cutting elements of slidable tissue cutter can be designed to cut tissue or to both cut and remove tissue. In some cut-and-remove embodiments, the cutting element can be circular, diagonal, angled, or other blade. The slidable tissue cutter can be designed and utilized to cut any body tissue including, but not limited to, skin, fat ligaments, cartilage, bone, or vessels. The cutting element can be of any desirable type, including thermal (laser, RF, etc.), chemical, ultrasonic, combination, or other.

This disclosure has provided certain examples of closure devices including clips and plugs. However, other types of closure devices can be utilized. In certain embodiments, a closure device can be smaller in an initial configuration or in a deployed configuration. In certain embodiments, the closure device can close a tissue opening by bringing closer together sides of the tissue opening and/or by partially or completely occluding the opening. The closure device can be partially or completely made from one or more of a polymer, rubber, silicone, metal, metal alloy, or other suitable material or materials.

The closure device may be partially or completely fabricated from a biodegradable/bioabsorbable material, including but not limited to one or more of modified cellulose, collagen, fibrin, fibrinogen, fibronectin, elastin, vitronectin, laminin, thrombin, albumin and gelatin or other connective proteins or natural materials, polymers or copolymers such as polyvinyl pyrrolidone, polylactide [poly-L-lactide (PLLA), poly-D-lactide (PDLA)], polyglycolide, polydioxanone, polycaprolactone, polygluconate, polylactic acid (PLA), polylactic acid-polyethylene oxide copolymers, poly(hydroxybutyrate), polyanhydride, polyphosphoester, poly (amino acids), poly(alpha-hydroxy acid) poly d,l-lactic acid (PLA) and copolymers of lactic acid and glycolic acid (PLGA), or related copolymers of these materials as well as composites and combinations thereof and combinations of other biodegradable/bioabsorbable materials. The closure device can be partially or completely fabricated from a biocompatible material, such as expanded polytetrafluoroethylene (ePTFE), polyester, polyurethane, silicone, rubber, Dacron, and/or urethane.

The closure device can include one or more coatings and/or be partially or completely formed from one or more of the following: swellable materials, bioabsorbable materials, and biocompatible materials.

The closure device also can have a biocompatible contact surface such as an adhesive, bonding compounds, or other solutions located on any surface of the closure device. The contact surface can be applied or integrated into the device in many ways, such as during the manufacturing process, just prior to deployment, or after the device has been deployed. The bonding materials can be in the form of a liquid, semi solid, or solid. Suitable bonding materials can include gels, foams and microporous mesh. Suitable adhesives can include acrylates, cyanoacrylates, epoxies, fibrin-based adhesives, other biological based adhesives, UV light and/or heat activated or other specialized adhesives. The contact surface can bond on initial contact, or after a longer period of time to allow repositioning of the closure device if desired. Such a contact surface can include a crystalline polymer that changes from a non-tacky crystalline state to an adhesive gel state, such as when the temperature is raised from room temperature to body temperature. An example of such material is available under the trade name Intillemer™ adhesive, available from Landec Corp. as well as composites and combinations thereof and combinations of other materials. Suppliers of biocompatible adhesives include, but are not limited to, Plasto (Dijon, France), Haemacure (Montreal, Canada), Cohesion (Palo Alto, Calif.), Cryolife (Kennesaw, Ga.), TissueLink (Dover, N.H.), and others. To increase the work time of the contact surface and/or to allow repositioning of the closure device after it has been deployed, the contact surface can be blended with a material such as a starch or other material, that retards or delays bonding to allow repositioning of the coupler after it has been deployed. A degradable coating can be placed over the contact surface so that it degrades and exposes the adhesive. Other contact surfaces can include composites-based adherents and combinations of the above materials and other suitable materials as are known in the art.

Although the inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. Thus, it is intended that the scope of the present inventions herein disclosed should not be limited by the particular disclosed embodiments described above, but should be determined only by a fair reading of the claims that follow.

The invention claimed is:

1. A method of deploying a vascular closure device, comprising the steps of:
providing a deployment device having an inner tube and an outer tube, with a plug in a non-swelled state mounted on a distal end of the inner tube, wherein at least a portion of the plug is within the outer tube, the plug comprising a swellable material that swells when exposed to fluid, the plug further comprising a first portion having a first cross-sectional area and a second portion having a second cross-sectional area, the second cross-sectional area being larger than the first cross-sectional area, the plug having a longitudinal channel passing through the first and second portions;
advancing a distal end of the deployment device over an elongate medical device to an opening in a blood vessel such that said second portion of the plug is received against an outer wall of the vessel opening and said plug is exposed to a bodily fluid, wherein the plug remains mounted on the distal end of the inner tube and the portion of the plug within the outer tube remains therewithin when the second portion of the plug is received against the outer wall of the vessel opening; and
producing generally longitudinal movement between the inner tube and the outer tube of the deployment device to release the plug from the deployment device, wherein the inner tube pushes the plug free of the outer tube;
wherein the plug swells upon said exposure to the bodily fluid to substantially occlude the longitudinal channel, thereby sealing the vessel opening.

2. The method of claim 1 wherein the first portion of the plug is within the outer wall of the vessel when the second portion is received against the outer wall of the vessel.

3. The method of claim 1 wherein the longitudinal channel is coated with an adhesive or other coating configured to assist in occluding the longitudinal channel.

4. The method of claim 1 wherein the elongate medical device is within the longitudinal channel while advancing the distal end of the deployment device over the elongate medical device.

5. The method of claim 1 further comprising withdrawing the elongate medical device from the blood vessel prior to releasing the plug from the deployment device.

6. The method of claim 1 wherein the bodily fluid is blood, saline, or subcutaneous fluid.

7. The method of claim 1 wherein the plug is at least partially bioabsorbable.

8. The method of claim 7 wherein the plug is configured to be absorbed by the patient's body after about 4 weeks.

9. The method of claim 1 wherein the plug includes a rigid outer coating that begins to dissolve upon exposure to the bodily fluid.

10. The method of claim 1 wherein the elongate medical device is one or more of the following: introducer, sheath, dilator, trocar, endoscope, catheter, guide wire, needle, or tube.

11. The method of claim 1 wherein the inner tube has a handle and is moved longitudinally by applying pressure to the handle in a distal direction or by pulling the handle in a proximal direction.

12. The method of claim 1 wherein the inner tube has a handle and the outer tube has a handle, and a stop is provided that maintains separation between the inner tube handle and the outer tube handle.

13. The method of claim 12 further comprising removing the stop, thereby permitting the inner tube to move relative to the outer tube.

14. The method of claim 13 wherein the stop is a removable element affixed to the outer tube between the inner tube handle and the outer tube handle.

15. The method of claim 13 wherein the plug is fully deployed when the inner tube handle and the outer tube handle are brought together.

16. The method of claim 1 wherein the plug is partially or completely fabricated from polyethylene glycol (PEG).

17. The method of claim 1 wherein the plug comprises a contact surface with an adhesive or bonding compounds.

18. The method of claim 1 wherein the plug includes a therapeutic agent.

19. The method of claim 1, wherein the inner tube has an inner lumen configured to receive the elongate medical device.

20. The method of claim 19, wherein inner tube has an elongate slot allowing a proximal portion of the elongate medical device to be tilted away from and axially separated from the inner tube without detaching the deployment device from the elongate medical device when received by the inner lumen of the inner tube.

21. The method of claim 20, wherein the outer tube has an elongate slot aligned with the elongate slot of the inner tube.

22. The method of claim 1, wherein the plug includes a longitudinal slit or spiral allowing the plug to be attached to the elongate medical device or the deployment device from a side of the elongate medical device or the deployment device.

23. A method of deploying a vascular closure device, comprising the steps of:
providing a deployment device having an inner tube and an outer tube, with a plug in a non-swelled state mounted on a distal end of the inner tube, wherein a portion of the plug is within a distal end of the outer tube of the deployment device and a portion of the plug extends out of the distal end of the deployment device, the plug comprising a swellable material that swells when exposed to fluid, the plug further comprising a first portion having a first cross-sectional area and a second portion having a second cross-sectional area, the second cross-sectional area being larger than the first cross-sectional area, the plug having a longitudinal channel passing through the first and second portions;
advancing the distal end of the deployment device over an elongate medical device to an opening in a blood vessel such that said second portion of the plug is received against an outer wall of the vessel opening and said plug is exposed to a bodily fluid, wherein the plug remains mounted on the distal end of the inner tube and the portion of the plug within the distal end of the deployment device remains therewithin when the second portion of the plug is received against the outer wall of the vessel opening; and
producing generally longitudinal movement between the inner tube and the outer tube of the deployment device to release the plug from the deployment device;
wherein the plug swells upon said exposure to the bodily fluid to substantially occlude the longitudinal channel, thereby sealing the vessel opening.

24. The method of claim 23 wherein the portion of the plug that extends out of the distal end of the deployment device has the second cross-sectional area and the portion of the plug that is within the outer tube of the distal end of the deployment device has a smaller cross-sectional area than the second cross-sectional area.

25. The method of claim 23 wherein the first portion of the plug is within the outer wall of the vessel when the second portion is received against the outer wall of the vessel.

26. The method of claim 23 wherein the longitudinal channel is coated with an adhesive or other coating configured to assist in occluding the longitudinal channel.

27. The method of claim 23 wherein the elongate medical device is within the longitudinal channel while advancing the distal end of the deployment device over the elongate medical device.

28. The method of claim 23 further comprising withdrawing the elongate medical device from the blood vessel prior to releasing the plug from the deployment device.

29. The method of claim 23 wherein the bodily fluid is blood, saline, or subcutaneous fluid.

30. The method of claim 23 wherein the plug is at least partially bioabsorbable.

31. The method of claim 23 wherein the plug is configured to be absorbed by the patient's body after about 4 weeks.

32. The method of claim 23 wherein the plug includes a rigid outer coating that begins to dissolve upon exposure to the bodily fluid.

33. The method of claim 23 wherein the elongate medical device is one or more of the following: introducer, sheath, dilator, trocar, endoscope, catheter, guide wire, needle, or tube.

34. The method of claim 23 wherein the distal end of the inner tube pushes the plug free of the outer tube.

35. The method of claim 34 wherein the inner tube has a handle and is moved longitudinally by applying pressure to the handle in a distal direction or by pulling the handle in a proximal direction.

36. The method of claim 34 wherein the inner tube has a handle and the outer tube has a handle, and a stop is provided that maintains separation between the inner tube handle and the outer tube handle.

37. The method of claim 36 further comprising removing the stop, thereby permitting the inner tube to move relative to the outer tube.

38. The method of claim 37 wherein the stop is a removable element affixed to the outer tube between the inner tube handle and the outer tube handle.

39. The method of claim 37 wherein the plug is fully deployed when the inner tube handle and the outer tube handle are brought together.

40. The method of claim 23 wherein the plug is partially or completely fabricated from polyethylene glycol (PEG).

41. The method of claim 23 wherein the plug comprises a contact surface with an adhesive or bonding compounds.

42. The method of claim 23 wherein the plug includes a therapeutic agent.

43. The method of claim 23, wherein the inner tube has an inner lumen configured to receive the elongate medical device.

44. The method of claim 43, wherein inner tube has an elongate slot allowing a proximal portion of the elongate medical device to be tilted away from and axially separated from the inner tube without detaching the deployment device from the elongate medical device when received by the inner lumen of the inner tube.

45. The method of claim 44, wherein the outer tube has an elongate slot aligned with the elongate slot of the inner tube.

46. The method of claim 23, wherein the plug includes a longitudinal slit or spiral allowing the plug to be attached to the elongate medical device or the deployment device from a side of the elongate medical device or the deployment device.

\* \* \* \* \*